(12) United States Patent
Lane et al.

(10) Patent No.: US 9,241,790 B2
(45) Date of Patent: *Jan. 26, 2016

(54) TRANSCATHETER MITRAL VALVE PROSTHESIS

(71) Applicant: Neovasc Tiara Inc., Richmond (CA)

(72) Inventors: Randy Matthew Lane, Langley (CA); Colin A. Nyuli, Vancouver (CA)

(73) Assignee: Neovasc Tiara Inc., Vancouver, B.C.

( * ) Notice: Subject to any disclaimer, the term of this patent is extended or adjusted under 35 U.S.C. 154(b) by 0 days.

This patent is subject to a terminal disclaimer.

(21) Appl. No.: 14/685,418

(22) Filed: Apr. 13, 2015

(65) Prior Publication Data

US 2015/0216655 A1 Aug. 6, 2015

Related U.S. Application Data

(60) Continuation of application No. 14/046,606, filed on Oct. 4, 2013, which is a division of application No. 13/096,572, filed on Apr. 28, 2011, now Pat. No. 8,579,964.

(Continued)

(51) Int. Cl.
*A61F 2/24* (2006.01)
*A61F 2/95* (2013.01)

(52) U.S. Cl.
CPC ............. *A61F 2/2412* (2013.01); *A61F 2/2409* (2013.01); *A61F 2/2418* (2013.01);
(Continued)

(58) Field of Classification Search
CPC ....... A61F 2/2409; A61F 2/24; A61F 2/2418; A61F 2/2436; A61F 2002/9505; A61F 2002/9517; A61F 2220/0008; A61F 2220/0016; A61F 2230/005; A61F 2230/0054
USPC .............................. 623/2.11, 2.14–2.19, 2.38
See application file for complete search history.

(56) References Cited

U.S. PATENT DOCUMENTS

| 3,739,402 A | 6/1973 | Kahn et al. |
| 4,079,468 A | 3/1978 | Liotta et al. |

(Continued)

FOREIGN PATENT DOCUMENTS

| CN | 101262833 A | 9/2008 |
| DE | 102006052564 B3 | 12/2007 |

(Continued)

OTHER PUBLICATIONS

Al-Attar. Next generation surgical aortic biological prostheses: sutureless valves. European Society of Cardiology. Dec. 21, 2011; 10(14):1-3.

(Continued)

*Primary Examiner* — Jonathan W Miles
*Assistant Examiner* — George J Ulsh
(74) *Attorney, Agent, or Firm* — Wilson Sonsini Goodrich & Rosati

(57) ABSTRACT

A prosthetic cardiac valve comprises an anchor having an atrial skirt, an annular region, and a ventricular skirt. The prosthetic valve also has a plurality of prosthetic valve leaflets each having a first end and a free end. The first end is coupled with the anchor and the free end is opposite the first end. The prosthetic cardiac valve has an open configuration in which the free ends of the prosthetic valve leaflets are disposed away from one another to allow antegrade blood flow therepast, and a closed configuration in which the free ends of the prosthetic valve leaflets engage one another and substantially prevent retrograde blood flow therepast. The anchor has a collapsed configuration for delivery to the heart and an expanded configuration for anchoring the prosthetic cardiac valve to a patient's heart.

28 Claims, 43 Drawing Sheets

Related U.S. Application Data

(60) Provisional application No. 61/414,879, filed on Nov. 17, 2010, provisional application No. 61/393,860, filed on Oct. 15, 2010, provisional application No. 61/331,799, filed on May 5, 2010.

(52) U.S. Cl.
CPC ............ *A61F2/2427* (2013.01); *A61F 2/2436* (2013.01); *A61F 2002/9505* (2013.01); *A61F 2002/9517* (2013.01); *A61F 2220/0008* (2013.01); *A61F 2220/0016* (2013.01); *A61F 2230/005* (2013.01); *A61F 2230/0034* (2013.01); *A61F 2230/0054* (2013.01); *A61F 2250/0067* (2013.01); *A61F 2250/0098* (2013.01)

(56) References Cited

U.S. PATENT DOCUMENTS

| | | |
|---|---|---|
| 4,204,283 A | 5/1980 | Bellhouse et al. |
| 4,339,831 A | 7/1982 | Johnson |
| 4,340,977 A | 7/1982 | Brownlee et al. |
| 4,470,157 A | 9/1984 | Love |
| 4,490,859 A | 1/1985 | Black et al. |
| 4,865,600 A | 9/1989 | Carpentier et al. |
| 5,415,667 A | 5/1995 | Frater |
| 5,669,919 A | 9/1997 | Sanders et al. |
| 5,868,782 A | 2/1999 | Frantzen |
| 5,928,281 A | 7/1999 | Huynh et al. |
| 6,042,606 A | 3/2000 | Frantzen |
| 6,074,417 A | 6/2000 | Peredo |
| 6,086,612 A | 7/2000 | Jansen |
| 6,113,631 A | 9/2000 | Jansen |
| 6,312,465 B1 | 11/2001 | Griffin et al. |
| 6,358,277 B1 | 3/2002 | Duran |
| 6,458,153 B1 | 10/2002 | Bailey et al. |
| 6,610,088 B1 | 8/2003 | Gabbay |
| 6,629,534 B1 | 10/2003 | St. Goar et al. |
| 6,652,578 B2 | 11/2003 | Bailey et al. |
| 6,702,843 B1 | 3/2004 | Brown et al. |
| 6,764,505 B1 | 7/2004 | Hossainy et al. |
| 6,875,231 B2 | 4/2005 | Anduiza et al. |
| 6,929,660 B1 | 8/2005 | Ainsworth et al. |
| 7,018,406 B2 | 3/2006 | Seguin et al. |
| 7,186,265 B2 | 3/2007 | Sharkawy et al. |
| 7,329,278 B2 | 2/2008 | Seguin et al. |
| 7,338,520 B2 | 3/2008 | Bailey et al. |
| 7,435,257 B2 | 10/2008 | Lashinski et al. |
| 7,442,204 B2 | 10/2008 | Schwammenthal et al. |
| 7,455,689 B2 | 11/2008 | Johnson |
| 7,524,330 B2 | 4/2009 | Berreklouw |
| 7,637,945 B2 | 12/2009 | Solem et al. |
| 7,637,946 B2 | 12/2009 | Solem et al. |
| 7,799,072 B2 | 9/2010 | Greenberg |
| 7,914,569 B2 | 3/2011 | Nguyen et al. |
| 7,914,575 B2 | 3/2011 | Guyenot et al. |
| 7,972,377 B2 | 7/2011 | Lane |
| 8,092,520 B2 | 1/2012 | Quadri |
| 8,226,710 B2 | 7/2012 | Nguyen et al. |
| 8,337,541 B2 | 12/2012 | Quadri et al. |
| 8,398,708 B2 | 3/2013 | Meiri et al. |
| 8,403,983 B2 | 3/2013 | Quadri et al. |
| 8,408,214 B2 | 4/2013 | Spenser |
| 8,414,644 B2 | 4/2013 | Quadri et al. |
| 8,449,599 B2 | 5/2013 | Chau et al. |
| 8,579,964 B2 | 11/2013 | Lane et al. |
| 8,652,203 B2 | 2/2014 | Quadri et al. |
| 8,795,356 B2 | 8/2014 | Quadri et al. |
| 2001/0007956 A1 | 7/2001 | Letac et al. |
| 2002/0032481 A1 | 3/2002 | Gabbay |
| 2003/0105517 A1 | 6/2003 | White et al. |
| 2003/0114913 A1 | 6/2003 | Spenser et al. |
| 2003/0176914 A1 | 9/2003 | Rabkin et al. |
| 2004/0093060 A1 | 5/2004 | Seguin et al. |
| 2004/0102842 A1 | 5/2004 | Jansen |
| 2004/0117009 A1 | 6/2004 | Cali et al. |
| 2004/0181238 A1 | 9/2004 | Zarbatany et al. |
| 2004/0193261 A1 | 9/2004 | Berreklouw |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2004/0243230 A1 | 12/2004 | Navia et al. |
| 2005/0075727 A1 | 4/2005 | Wheatley |
| 2005/0107872 A1 | 5/2005 | Mensah et al. |
| 2005/0137686 A1 | 6/2005 | Salahieh et al. |
| 2005/0137690 A1 | 6/2005 | Salahieh et al. |
| 2005/0159811 A1 | 7/2005 | Lane |
| 2005/0182486 A1 | 8/2005 | Gabbay |
| 2006/0020247 A1 | 1/2006 | Kagan et al. |
| 2006/0020327 A1 | 1/2006 | Lashinski et al. |
| 2006/0020334 A1 | 1/2006 | Lashinski et al. |
| 2006/0058872 A1 | 3/2006 | Salahieh et al. |
| 2006/0095115 A1 | 5/2006 | Bladillah et al. |
| 2006/0149360 A1 | 7/2006 | Schwammenthal et al. |
| 2006/0195183 A1 | 8/2006 | Navia et al. |
| 2006/0241745 A1 | 10/2006 | Solem |
| 2006/0259135 A1 | 11/2006 | Navia et al. |
| 2006/0259136 A1 | 11/2006 | Nguyen et al. |
| 2006/0293698 A1 | 12/2006 | Douk |
| 2006/0293745 A1 | 12/2006 | Carpentier et al. |
| 2007/0016286 A1 | 1/2007 | Herrmann et al. |
| 2007/0043435 A1 | 2/2007 | Seguin et al. |
| 2007/0050020 A1 | 3/2007 | Spence |
| 2007/0050021 A1 | 3/2007 | Johnson |
| 2007/0142906 A1 | 6/2007 | Figulla et al. |
| 2007/0255394 A1 | 11/2007 | Ryan |
| 2007/0293940 A1 | 12/2007 | Schaeffer et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0082164 A1 | 4/2008 | Friedman |
| 2008/0097571 A1 | 4/2008 | Denison et al. |
| 2008/0140175 A1 | 6/2008 | Boucher et al. |
| 2008/0147179 A1 | 6/2008 | Cai et al. |
| 2008/0177381 A1 | 7/2008 | Navia et al. |
| 2008/0183273 A1 | 7/2008 | Mesana et al. |
| 2008/0221672 A1 | 9/2008 | Lamphere et al. |
| 2008/0228201 A1 | 9/2008 | Zarbatany et al. |
| 2008/0228254 A1 | 9/2008 | Ryan |
| 2008/0243245 A1 | 10/2008 | Thambar et al. |
| 2008/0255660 A1 | 10/2008 | Guyenot et al. |
| 2009/0005863 A1 | 1/2009 | Goetz et al. |
| 2009/0012602 A1 | 1/2009 | Quadri |
| 2009/0062908 A1 | 3/2009 | Bonhoeffer et al. |
| 2009/0082844 A1 | 3/2009 | Zacharias et al. |
| 2009/0138079 A1 | 5/2009 | Tuval et al. |
| 2009/0171447 A1 | 7/2009 | Von Segesser et al. |
| 2009/0171456 A1 | 7/2009 | Kveen et al. |
| 2009/0188964 A1 | 7/2009 | Orlov |
| 2009/0216314 A1 | 8/2009 | Quadri |
| 2009/0259306 A1 | 10/2009 | Rowe |
| 2009/0276040 A1 | 11/2009 | Rowe et al. |
| 2009/0281618 A1 | 11/2009 | Hill et al. |
| 2009/0287296 A1 | 11/2009 | Manasse |
| 2009/0287299 A1 | 11/2009 | Tabor et al. |
| 2009/0292350 A1 | 11/2009 | Eberhardt et al. |
| 2009/0306768 A1 | 12/2009 | Quadri |
| 2009/0318871 A1 | 12/2009 | Zarbatany et al. |
| 2010/0036479 A1 | 2/2010 | Hill et al. |
| 2010/0082094 A1 | 4/2010 | Quadri et al. |
| 2010/0094411 A1 | 4/2010 | Tuval et al. |
| 2010/0131054 A1 | 5/2010 | Tuval et al. |
| 2010/0168839 A1 | 7/2010 | Braido et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0268332 A1 | 10/2010 | Tuval et al. |
| 2010/0298931 A1 | 11/2010 | Quadri et al. |
| 2010/0305685 A1 | 12/2010 | Millwee et al. |
| 2011/0004296 A1 | 1/2011 | Lutter et al. |
| 2011/0015731 A1 | 1/2011 | Carpentier et al. |
| 2011/0022157 A1 | 1/2011 | Essinger et al. |
| 2011/0137397 A1 | 6/2011 | Chau et al. |

(56) References Cited

U.S. PATENT DOCUMENTS

| | | |
|---|---|---|
| 2011/0178597 A9 | 7/2011 | Navia et al. |
| 2011/0202128 A1 | 8/2011 | Duffy |
| 2011/0208290 A1 | 8/2011 | Straubinger et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0264196 A1 | 10/2011 | Savage et al. |
| 2011/0313515 A1 | 12/2011 | Quadri et al. |
| 2011/0319989 A1 | 12/2011 | Lane et al. |
| 2012/0041550 A1 | 2/2012 | Salahieh et al. |
| 2012/0053681 A1 | 3/2012 | Alkhatib et al. |
| 2012/0078353 A1 | 3/2012 | Quadri et al. |
| 2012/0101571 A1 | 4/2012 | Thambar et al. |
| 2012/0101572 A1 | 4/2012 | Kovalsky et al. |
| 2012/0179239 A1 | 7/2012 | Quadri |
| 2012/0215303 A1 | 8/2012 | Quadri et al. |
| 2012/0271398 A1 | 10/2012 | Essinger et al. |
| 2012/0303116 A1 | 11/2012 | Gorman, III et al. |
| 2013/0053950 A1 | 2/2013 | Rowe et al. |
| 2013/0110227 A1 | 5/2013 | Quadri et al. |
| 2013/0131788 A1 | 5/2013 | Quadri et al. |
| 2013/0131793 A1 | 5/2013 | Quadri et al. |
| 2013/0138203 A1 | 5/2013 | Quadri |
| 2013/0138207 A1 | 5/2013 | Quadri et al. |
| 2013/0144378 A1 | 6/2013 | Quadri et al. |
| 2013/0144380 A1 | 6/2013 | Quadri et al. |
| 2013/0144381 A1 | 6/2013 | Quadri et al. |
| 2013/0184813 A1 | 7/2013 | Quadri et al. |
| 2013/0304200 A1 | 11/2013 | McLean et al. |
| 2013/0310928 A1 | 11/2013 | Morriss et al. |
| 2014/0039611 A1 | 2/2014 | Lane et al. |
| 2014/0172085 A1 | 6/2014 | Quadri et al. |
| 2014/0172086 A1 | 6/2014 | Quadri et al. |
| 2014/0222136 A1 | 8/2014 | Geist et al. |
| 2014/0277390 A1 | 9/2014 | Ratz et al. |
| 2014/0277422 A1 | 9/2014 | Ratz et al. |
| 2014/0277427 A1 | 9/2014 | Ratz et al. |
| 2015/0257878 A1 | 9/2015 | Lane et al. |

FOREIGN PATENT DOCUMENTS

| | | |
|---|---|---|
| EP | 2566416 A1 | 3/2013 |
| GB | 1264471 A | 2/1972 |
| GB | 1315844 A | 5/1973 |
| WO | WO-0236048 A1 | 5/2002 |
| WO | WO-0238084 A2 | 5/2002 |
| WO | WO-2006097931 A2 | 9/2006 |
| WO | WO-2006113906 A1 | 10/2006 |
| WO | WO-2007058857 A2 | 5/2007 |
| WO | WO-2006097931 A3 | 7/2007 |
| WO | WO-2007097983 A2 | 8/2007 |
| WO | WO-2007122459 A2 | 11/2007 |
| WO | WO-2007122459 A3 | 1/2008 |
| WO | WO-2008005535 A2 | 1/2008 |
| WO | WO-2008013915 A2 | 1/2008 |
| WO | WO-2007097983 A3 | 3/2008 |
| WO | WO-2008013915 A3 | 7/2008 |
| WO | WO-2008103722 A2 | 8/2008 |
| WO | WO-2008103722 A3 | 10/2008 |
| WO | WO-2009033469 A1 | 3/2009 |
| WO | WO-2009053497 A1 | 4/2009 |
| WO | WO-2009108615 A1 | 9/2009 |
| WO | WO-2009134701 A2 | 11/2009 |
| WO | WO-2010004546 A1 | 1/2010 |
| WO | WO-2009134701 A3 | 2/2010 |
| WO | WO-2010037141 A1 | 4/2010 |
| WO | WO-2010057262 A1 | 5/2010 |
| WO | WO-2011072084 A2 | 6/2011 |
| WO | WO-2011137531 A1 | 11/2011 |
| WO | WO-2012035279 A1 | 3/2012 |

OTHER PUBLICATIONS

Banai, et al. Tiara: a novel catheter-based mitrel valve bioprosthesis: initial experiments and short-term pre-clinical results J Am Coll Cardiol Oct. 9, 2012;60(15):1430-1. doi: 10.1016/j.jacc.2012.05.047. Epub Sep. 12, 2012.

Berreklouw, et al. Sutureless mitrel valve replacement with bioprostheses and Nitinol attachment rings: feasibility in acute pig experiments. J Thorac Cardiovasc Surg. Aug. 2011;142(2):390-5.e1. doi: 10.1016/j.jtcvs.2010.12.018. Epub Feb. 4, 2011.

Boudjemline, et al. Steps toward the percutaneous replacement of atrioventricular valves an experimental study. J Am Coll Cardiol. Jul. 19, 2005;46(2):360-5.

Brinkman, et al. Transcatheter cardiac valve interventions. Surg Clin North Am. Aug. 2009;89(4):951-66, x. doi: 10.1016/j.suc.2009.06.004.

CardiAQ Valve Technologies to pursue first-in-man studies of its transcatheter mitral valve system. Cardiac Interventions Today. Jan. 12, 2010.

Chiam, et al. Percutaneous transcatheter aortic valve implantation: assessing results, judging outcomes, and planning trials: the interventionalist perspective. JACC Cardiovasc Interv. Aug. 2008;1(4):341-50. doi: 10.1016/j.jcin.2008.03.018.

Condado, et al. Percutaneous treatment of heart valves. Rev Esp Cardiol. Dec. 2006;59(12):1225-31.

CoreValve USA. An advanced TAVR design. Medtronic.com. Accessed Jan. 27, 2015.

De Backer, et al. Percutaneous transcatheter mitrel valve replacement: an overview of devices in preclinical and early clinical evalutation. Circ Cardiovasc Interv. Jun. 2014;7(3):400-9. doi: 10.1161/CIRCINTERVENTIONS.114.001607.

Edwards Lifesciences 2005 annual report. Accessed Jan. 27, 2015.

Fanning, et al. Transcatheter aortic valve implantation (TAVI): valve design and evolution. Int J Cardiol. Oct. 3, 2013;168(3):1822-31. doi: 10.1016/j.ijcard.2013.07.117. Epub Aug. 20, 2013.

Gillespie, et al. Sutureless mitral valve replacement: initial steps toward a percutaneous procedure. Ann Thorac Surg. Aug. 2013;96(2):670-4. doi: 10.1016/j.athoracsur.2013.02.065.

Grube, et al. Percutaneous implantation of the CoreValve self-expanding valve prothesis in high-risk patients with aortic valve disease: the Siegburg first-in-man study. Circulation. Oct. 10, 2006;114(15):1616-24. Epub Oct. 2, 2006.

Harmon, et al. Effect of acute myocardial infarction on the angle between the mitrak and aortic valve plane. Am J Cardiol. Aug. 1, 1999;84(3):342-4, A8.

Herrman. Trancatheter mitral valve implantation. Cardiac Interventions Today. Aug./Sep. 2009; 81-85.

Ionasec, et al. Personalized modeling and assessment of the aortic-mitral coupling from 4D TEE and CT. Med Image Comput Comput Assist Interv. 2009;12(Pt 2):767-75.

Karimi, et al. Percutaneous Valve Therapies. SIS 2007 Year book. Chapter 11. 11 pages.

Kumar, et al. Design considerations and quantitative assessment for the development of percutaneous mitral valve stent. Med Eng Phys. Jul. 2014;36(7):882-8. doi: 10.1016/j.medengphy.2014.03.010. Epub Apr. 16, 2014.

Lauten; et al., "Experimental evaluation of the JenaClip transcatheter aortic valve." Sep. 1, 2009, 74(3), 514-9.

Leon, et al. Transcatheter aortic valve replacement in patients with critical aortic stenosis: rationale, device descriptions, early clinical experiences, and perspectives. Semin Thorac Cardiovasc Surg. 2006 Summer;18(2):165-74.

Lozonschi, et al. Transapical mitral valved stent implantation. Ann Thorac Surg. Sep. 2008;86(3):745-8. doi: 10.1016/j.athoracsur.2008.05.039.

Lutter, et al. Off-pump transapical mitral valve replacement. Eur J Cardiothorac Surg. Jul. 2009;36(1):124-8; discussion 128. doi: 10.1016/j.ejcts.2009.02.037. Epub Apr. 25, 2009.

Lutter, et al. Transapical mitral valve implantation: the Lutter valve. Heart Lung Vessel. 2013;5(4):201-6.

Ma, et al. Double-crowned valved stents for off pump mitral vlave replacement. Eur J Cardiothorac Surg. Aug. 2005;28(2):194-8; discussion 198-9.

Maisano, et al. Mitral transcatheter technolofies. Rambam Maimonides Med. J. Jul. 25, 2013;4(3):e0015. doi: 10.5041/RMMJ.10115. Print Jul. 2013.

(56) References Cited

OTHER PUBLICATIONS

Navia, et al. Sutureless implantation a expandable mitral stent-valve prosthesis in acute animal model. TCT728. JACC. Nov. 8, 2011. vol. 58, No. 20 Suppl B. B194.
Orton. Mitralseal: hybrid trancatheter mitral valve replacement. Colorado State University. 2011; 311-312. https://www.acvs.org/files/proceedings/2011/data/papers/102.pdf.
Piazza, et al. Anatomy of the aortic valvar complex and its implications for transcatheter implantation of the aortic valve. Circ Cardiovasc Interv. Aug. 2008;1(1):74-81. doi: 10.1161/CIRCINTERVENTIONS.108.780858.
Pluth, et al. Aortic and mitral valve replacement with cloth-covered Braunwald-Cutter prosthesis. A three-year follow-up. Ann Thorac Surg. Sep. 1975;20(3):239-48.
Preston-Maher, et al. A Technical Review of Minimally Invasive Mitral Valve Replacements. Cardiovasc Eng Technol. 2015;6(2):174-184. Epub Nov. 25, 2014.
Quadri, et al. CVT is developing a non-surgical apporach to replacing mitral valves that may be the alternative to open-chest surgery. CardiAQ Valve Technologies. May 8, 2009.
Ribiero, et al. Balloon-expandable prostheses for transcatheter aortic valve replacement. Prog Cardiovasc Dis. May-Jun. 2014;56(6):583-95. doi: 10.1016/j.pcad.2014.02.001. Epub Mar. 1, 2014.
Seidel, et al. A mitral valve prosthesis and a study of thrombosis on heart valves in dogs. J Surg Res. May 1962;2:168-75.
Shuto, et al. Percutaneous transvenous Melody valve-in-ring procedure for mitral valve replacement. J Am Coll Cardiol. Dec. 6, 2011;58(24):2475-80. doi: 10.1016/j.jacc.2011.09.021.
Sondergaard, et al. First-in-human CardiAQ transcatheter mitral valve implantation via transapical approach. TCT-811. JACC Sep. 13, 2014. vol. 64, No. 11 Suppl B. B237.
Spencer, et al. Surgical treatment of valvular heart disease. Part V. Prosthetic replacement of the mitral valve. American Heart Journal. Oct. 1968; 76(4):576-580.
Spillner, et al. New sutureless 'atrial mitral-valve prosthesis' for minimally invasive mitral valve therapy. Textile Research Journal. 2010:1-7.
TAVR. Engager system. Precise Valve positioining. Accessed Jan. 28, 2015.
The JenaValve—the prosthesis. JenaValve Technology. Accessed Jan. 28, 2015.
Timek, et al. Aorto-mitral annular dynamics. Ann Thorac Surg. Dec. 2003;76(6):1944-50.
Tsang, et al. Changes in aortic-mitral coupling with severe aortic stenosis. JACC. Mar. 9, 2010; vol. 55. Issue 1A.
Veronesi, et al. A study of functional anatomy of aortic-mitral valve coupling using 3D matrix transesophageal echocardiography. Circ Cardiovasc Imaging. Jan. 2009;2(1):24-31. doi: 10.1161/CIRCIMAGING.108.785907. Epub Dec. 2, 2008.
Vu, et al. Novel sutureless mitral valve implantation method involving a bayonet insertion and release mechanism: a proof of concept study in pigs. J Thorac Cardiovasc Surg. Apr. 2012;143(4):985-8. doi: 10.1016/j.jtcvs.2012.01.037. Epub Feb. 11, 2012.
Walther, et al. Transapical approach for sutureless stent-fixed aortic valve implantation: experimental results. Eur J Cardiothorac Surg. May 2006;29(5):703-8. Epub Apr. 5, 2006.
Webb, et al. Transcatheter aortic valve implantation: the evolution of prostheses, delivery systems and approaches. Arch Cardiovasc Dis. Mar. 2012;105(3):153-9. doi: 10.1016/j.acvd.2012.02.001. Epub Mar. 16, 2012.
Bavaria. CardiAQ Valve Technologies (CVT) discloses successful results of acute in vivo study of its novel transcatheter mitral valve implantation (TMVI) system. Enhanced Online News. Sep. 28, 2009. Accessed: Mar. 8, 2012. http://eon.businesswire.com/news/eon/20090928005120/en/CardiAQ-Valve-Technologies/Heart/heart-failure.
Bavaria. CardiAQ Valve Technologies. TCT Company Overview. Transcatheter Cardiovascular Therapeutics Conference. San Francisco, CA. Sep. 21-25, 2009.

CardiAQ Valve Technologies. Percutaneous mitral valve replacement. Start-Up. Jun. 2009; 14(6):48-49.
*CardiAQ Valve Technologies v NeoVasc.* Case 1:14-cv-12405-NMG. Document 01-1. Filed Jun. 6, 2014.
*CardiAQ Valve Technologies v NeoVasc.* Case 1:14-cv-12405-NMG. Document 01-2. Filed Jun. 6, 2014.
*CardiAQ Valve Technologies v NeoVasc.* Case 1:14-cv-12405-NMG. Document 01-main. Filed Jun. 6, 2014.
*CardiAQ Valve Technologies v NeoVasc.* Case 1:14-cv-12405-NMG. Document 02-main. Filed Jun. 6, 2014.
*CardiAQ Valve Technologies v NeoVasc.* Case 1:14-cv-12405-NMG. Document 03-1. Filed Jun. 6, 2014.
*CardiAQ Valve Technologies v NeoVasc.* Case 1:14-cv-12405-NMG. Document 03-2. Filed Jun. 6, 2014.
*CardiAQ Valve Technologies v NeoVasc.* Case 1:14-cv-12405-NMG. Document 03-3-. Filed Jun. 6, 2014.
*CardiAQ Valve Technologies v NeoVasc.* Case 1:14-cv-12405-NMG. Document 03-4. Filed Jun. 6, 2014.
*CardiAQ Valve Technologies v NeoVasc.* Case 1:14-cv-12405-NMG. Document 03-5. Filed Jun. 6, 2014.
*CardiAQ Valve Technologies v NeoVasc.* Case 1:14-cv-12405-NMG. Document 03-main. Filed Jun. 6, 2014.
*CardiAQ Valve Technologies v NeoVasc.* Case 1:14-cv-12405-NMG. Document 05-main. Filed Jun. 6, 2014.
*CardiAQ Valve Technologies v NeoVasc.* Case 1:14-cv-12405-NMG. Document 06-main. Filed Jul. 21, 2014.
*CardiAQ Valve Technologies v NeoVasc.* Case 1:14-cv-12405-NMG. Document 07-main. Filed Jul. 21, 2014.
*CardiAQ Valve Technologies v NeoVasc.* Case 1:14-cv-12405-NMG. Document 08-1. Filed Jul. 25, 2014.
*CardiAQ Valve Technologies v NeoVasc.* Case 1:14-cv-12405-NMG. Document 08-main. Filed Jul. 25, 2014.
*CardiAQ Valve Technologies v NeoVasc.* Case 1:14-cv-12405-NMG. Document 09-1. Filed Jul. 25, 2014.
*CardiAQ Valve Technologies v NeoVasc.* Case 1:14-cv-12405-NMG. Document 09-main. Filed Jul. 25, 2014.
*CardiAQ Valve Technologies v NeoVasc.* Case 1:14-cv-12405-NMG. Document 11-1. Filed Jul. 28, 2014.
*CardiAQ Valve Technologies v NeoVasc.* Case 1:14-cv-12405-NMG. Document 11-main. Filed Jul. 28, 2014.
*CardiAQ Valve Technologies v NeoVasc.* Case 1:14-cv-12405-NMG. Document 13-1. Filed Jul. 29, 2014.
*CardiAQ Valve Technologies v NeoVasc.* Case 1:14-cv-12405-NMG. Document 13-2. Filed Jul. 29, 2014.
*CardiAQ Valve Technologies v NeoVasc.* Case 1:14-cv-12405-NMG. Document 13-main. Filed Jul. 29, 2014.
*CardiAQ Valve Technologies v NeoVasc.* Case 1:14-cv-12405-NMG. Document 14-1. Filed Jul. 29, 2014.
*CardiAQ Valve Technologies v NeoVasc.* Case 1:14-cv-12405-NMG. Document 14-2. Filed Jul. 29, 2014.
*CardiAQ Valve Technologies v NeoVasc.* Case 1:14-cv-12405-NMG. Document 14-main. Filed Jul. 29, 2014.
*CardiAQ Valve Technologies v NeoVasc.* Case 1:14-cv-12405-NMG. Document 15-1. Filed Jul. 29, 2014.
*CardiAQ Valve Technologies v NeoVasc.* Case 1:14-cv-12405-NMG. Document 15-2. Filed Jul. 29, 2014.
*CardiAQ Valve Technologies v NeoVasc.* Case 1:14-cv-12405-NMG. Document 15-main. Filed Jul. 29, 2014.
*CardiAQ Valve Technologies v NeoVasc.* Case 1:14-cv-12405-NMG. Document 16-1. Filed Jul. 29, 2014.
*CardiAQ Valve Technologies v NeoVasc.* Case 1:14-cv-12405-NMG. Document 16-2. Filed Jul. 29, 2014.
*CardiAQ Valve Technologies v NeoVasc.* Case 1:14-cv-12405-NMG. Document 16-main. Filed Jul. 29, 2014.
*CardiAQ Valve Technologies v NeoVasc.* Case 1:14-cv-12405-NMG. Document 17-1. Filed Jul. 29, 2014.
*CardiAQ Valve Technologies v NeoVasc.* Case 1:14-cv-12405-NMG. Document 17-main. Filed Jul. 29, 2014.
*CardiAQ Valve Technologies v NeoVasc.* Case 1:14-cv-12405-NMG. Document 18-main. Filed Jul. 29, 2014.
*CardiAQ Valve Technologies v NeoVasc.* Case 1:14-cv-12405-NMG. Document 19-1. Filed Jul. 29, 2014.

(56) References Cited

OTHER PUBLICATIONS

*CardiAQ Valve Technologies* v *NeoVasc.* Case 1:14-cv-12405-NMG. Document 19-main. Filed Jul. 29, 2014.
*CardiAQ Valve Technologies* v *NeoVasc.* Case 1:14-cv-12405-NMG. Document 20-main. Filed Jul. 29, 2014.
*CardiAQ Valve Technologies* v *NeoVasc.* Case 1:14-cv-12405-NMG. Document 21-main. Filed Jul. 29, 2014.
*CardiAQ Valve Technologies* v *NeoVasc.* Case 1:14-cv-12405-NMG. Document 22-1. Filed Jul. 29, 2014.
*CardiAQ Valve Technologies* v *NeoVasc.* Case 1:14-cv-12405-NMG. Document 22-main. Filed Jul. 29, 2014.
*CardiAQ Valve Technologies* v *NeoVasc.* Case 1:14-cv-12405-NMG. Document 24-1. Filed Aug. 12, 2014.
*CardiAQ Valve Technologies* v *NeoVasc.* Case 1:14-cv-12405-NMG. Document 24-2. Filed Aug. 12, 2014.
*CardiAQ Valve Technologies* v *NeoVasc.* Case 1:14-cv-12405-NMG. Document 24-3. Filed Aug. 12, 2014.
*CardiAQ Valve Technologies* v *NeoVasc.* Case 1:14-cv-12405-NMG. Document 24-4. Filed Aug. 12, 2014.
*CardiAQ Valve Technologies* v *NeoVasc.* Case 1:14-cv-12405-NMG. Document 24-5. Filed Aug. 12, 2014.
*CardiAQ Valve Technologies* v *NeoVasc.* Case 1:14-cv-12405-NMG. Document 24-main. Filed Aug. 12, 2014.
*CardiAQ Valve Technologies* v *NeoVasc.* Case 1:14-cv-12405-NMG. Document 25-main. Filed Aug. 12, 2014.
*CardiAQ Valve Technologies* v *NeoVasc.* Case 1:14-cv-12405-NMG. Document 26-main. Filed Aug. 12, 2014.
*CardiAQ Valve Technologies* v *NeoVasc.* Case 1:14-cv-12405-NMG. Document 27-1. Filed Aug. 12, 2014.
*CardiAQ Valve Technologies* v *NeoVasc.* Case 1:14-cv-12405-NMG. Document 27-2. Filed Aug. 12, 2014.
*CardiAQ Valve Technologies* v *NeoVasc.* Case 1:14-cv-12405-NMG. Document 27-3. Filed Aug. 12, 2014.
*CardiAQ Valve Technologies* v *NeoVasc.* Case 1:14-cv-12405-NMG. Document 27-main. Filed Aug. 12, 2014.
*CardiAQ Valve Technologies* v *NeoVasc.* Case 1:14-cv-12405-NMG. Document 28-main. Filed Aug. 12, 2014.
*CardiAQ Valve Technologies* v *NeoVasc.* Case 1:14-cv-12405-NMG. Document 29-main. Filed Aug. 13, 2014.
*CardiAQ Valve Technologies* v *NeoVasc.* Case 1:14-cv-12405-NMG. Document 30-main. Filed Aug. 19, 2014.
*CardiAQ Valve Technologies* v *NeoVasc.* Case 1:14-cv-12405-NMG. Document 31-1. Filed Aug. 19, 2014.
*CardiAQ Valve Technologies* v *NeoVasc.* Case 1:14-cv-12405-NMG. Document 31-2. Filed Aug. 19, 2014.
*CardiAQ Valve Technologies* v *NeoVasc.* Case 1:14-cv-12405-NMG. Document 31-Main. Filed Aug. 19, 2014.
*CardiAQ Valve Technologies* v *NeoVasc.* Case 1:14-cv-12405-NMG. Document 32-main. Filed Aug. 19, 2014.
*CardiAQ Valve Technologies* v *NeoVasc.* Case 1:14-cv-12405-NMG. Document 34-main. Filed Aug. 20, 2014.
*CardiAQ Valve Technologies* v *NeoVasc.* Case 1:14-cv-12405-NMG. Document 35-main. Filed Aug. 20, 2014.
*CardiAQ Valve Technologies* v *NeoVasc.* Case 1:14-cv-12405-NMG. Document 36-main. Filed Aug. 20, 2014.
*CardiAQ Valve Technologies* v *NeoVasc.* Case 1:14-cv-12405-NMG. Document 38-main. Filed Aug. 28, 2014.
*CardiAQ Valve Technologies* v *NeoVasc.* Case 1:14-cv-12405-NMG. Document 39-main. Filed Aug. 28, 2014.
*CardiAQ Valve Technologies* v *NeoVasc.* Case 1:14-cv-12405-NMG. Document 40-main. Filed Sep. 11, 2014.
*CardiAQ Valve Technologies* v *NeoVasc.* Case 1:14-cv-12405-NMG. Document 41-main. Filed Sep. 11, 2014.
*CardiAQ Valve Technologies* v *NeoVasc.* Case 1:14-cv-12405-NMG. Document 42-main. Filed Oct. 3, 2014.
*CardiAQ Valve Technologies* v *NeoVasc.* Case 1:14-cv-12405-NMG. Document 43-main. Filed Oct. 7, 2014.
Carpentier-Edwards. Why comprise in the mitral position? Edwards Lifesciences. 2004.
Co-pending U.S. Appl. No. 14/692,605, filed Apr. 21, 2015.
European search report and opinion dated Dec. 10, 2013 for EP Application No. 11777065.1.
Fitzgerald. Tomorrow's technology: percutaneous mitral valve replacement, chordal shortening and beyond. Transcatheter Valve Therapies (TVT) Conference. Seattle, WA. Jun. 7, 2010.
International search report and written opinion dated Sep. 27, 2011 for PCT/CA2011/000662.
Mack. Advantages and limitations of surgical mitral valve replacement; lessons for the transcatheter approach. Jun. 7, 2010. Texas Cardiovascular Innovative Ventures (TCIV) Conference. Dallas, TX. Dec. 8, 2010.
Medical Devices Today. CardiAQ Valve Technologies. Start-Up— Jul. 17, 2009. Accessed: Mar. 8, 2012. http:/www.medicaldevicestoday.com/2009/07/medical-device-start-up-cardiaq-valve-technologies-percutaneous-mitral-valve-replacement.html.
Notice of allowance dated Sep. 26, 2013 for U.S. Appl. No. 13/096,572.
Office action dated Jun. 4, 2013 for U.S. Appl. No. 13/096,572.
Ostrovsky. Transcatheter mitral valve implantation technology from CardiAQ. Posted Jan. 15, 2010. Accessed Jun. 27, 2012 from http://medgadget.com/2010/01/transcatheter_mitral_valve_implantation_technology_from_cardiaq.html.
Ratz. CardiAQ Valve Technologies. Innovations in heartvalve therapy. IN3 San Francisco. Jun. 18, 2008. PowerPoint presentation in 19 slides.
Ruiz. Overview of novel transcatheter valve technologies. Glimpse into the future. New transcatheter mitral valve treatment. Euro PCR. Paris, France. May 27, 2010.
Notice of allowance dated Nov. 5, 2015 for U.S. Appl. No. 14/692,605.
Office action dated Sep. 18, 2015 for U.S. Appl. No. 14/046,606.
Office action dated Aug. 14, 2015 for U.S. Appl. No. 14/692,605.

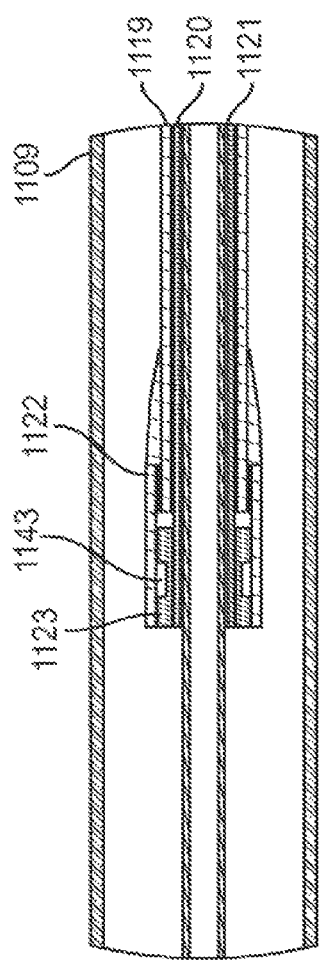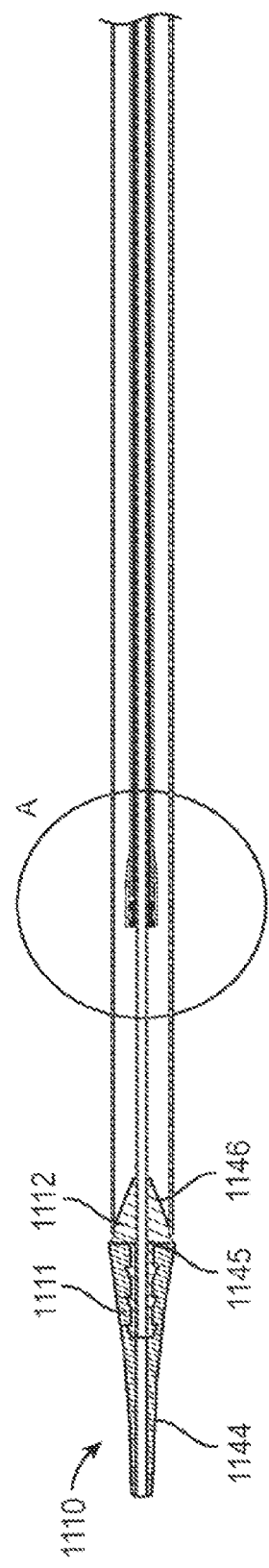
FIG. 15A

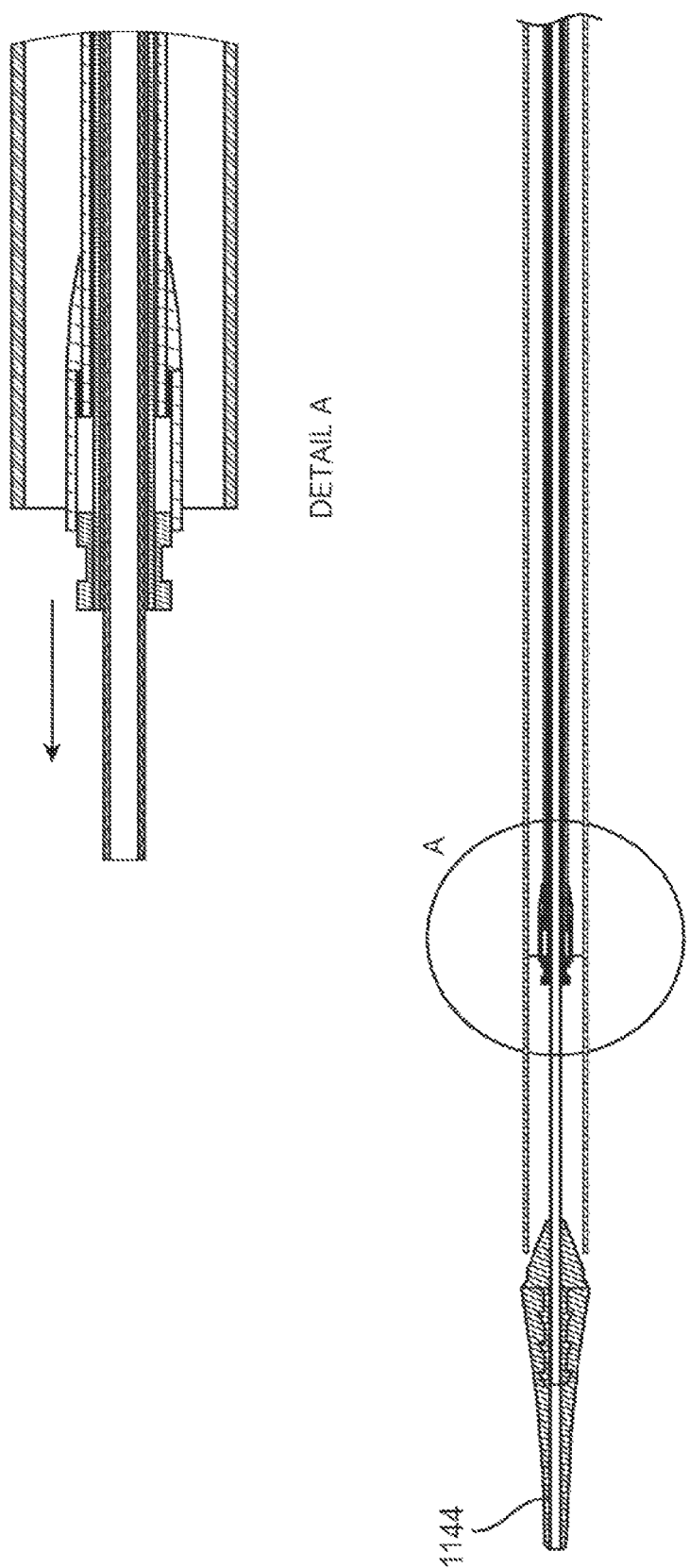

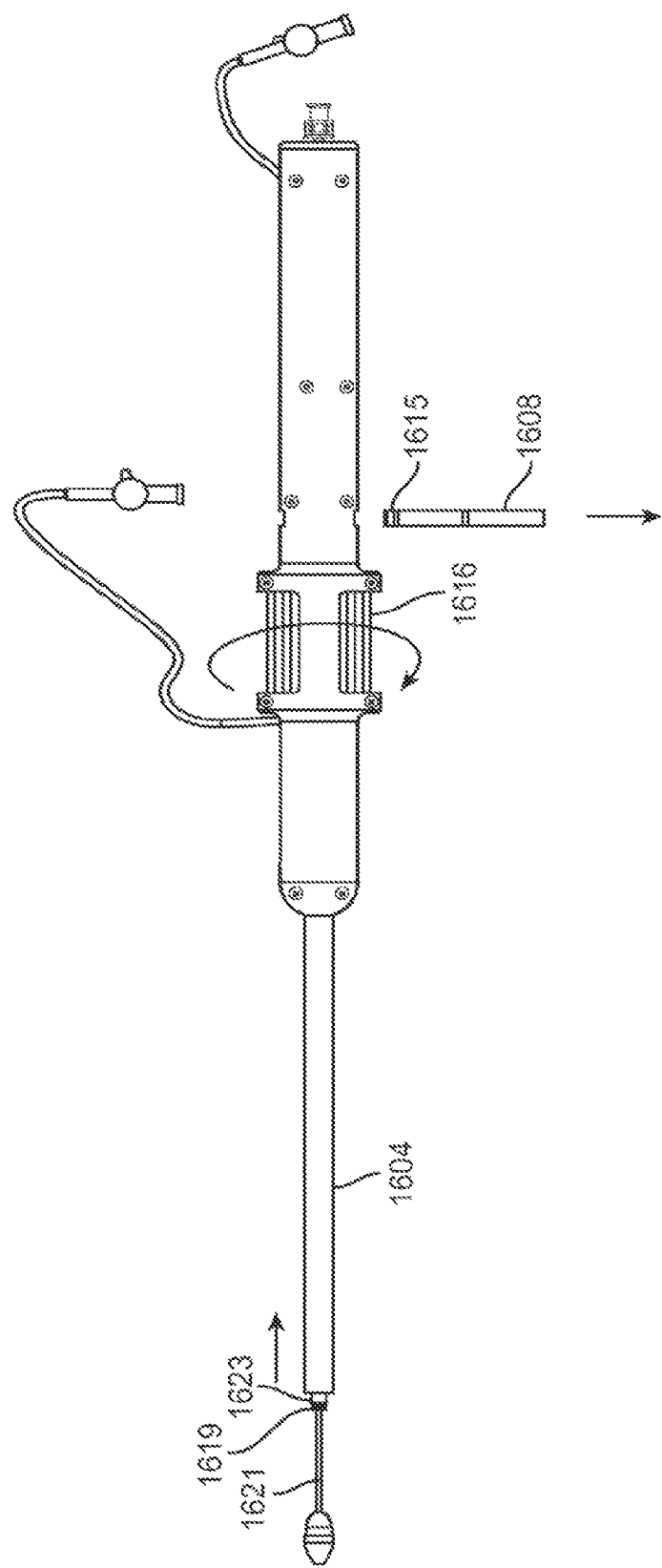

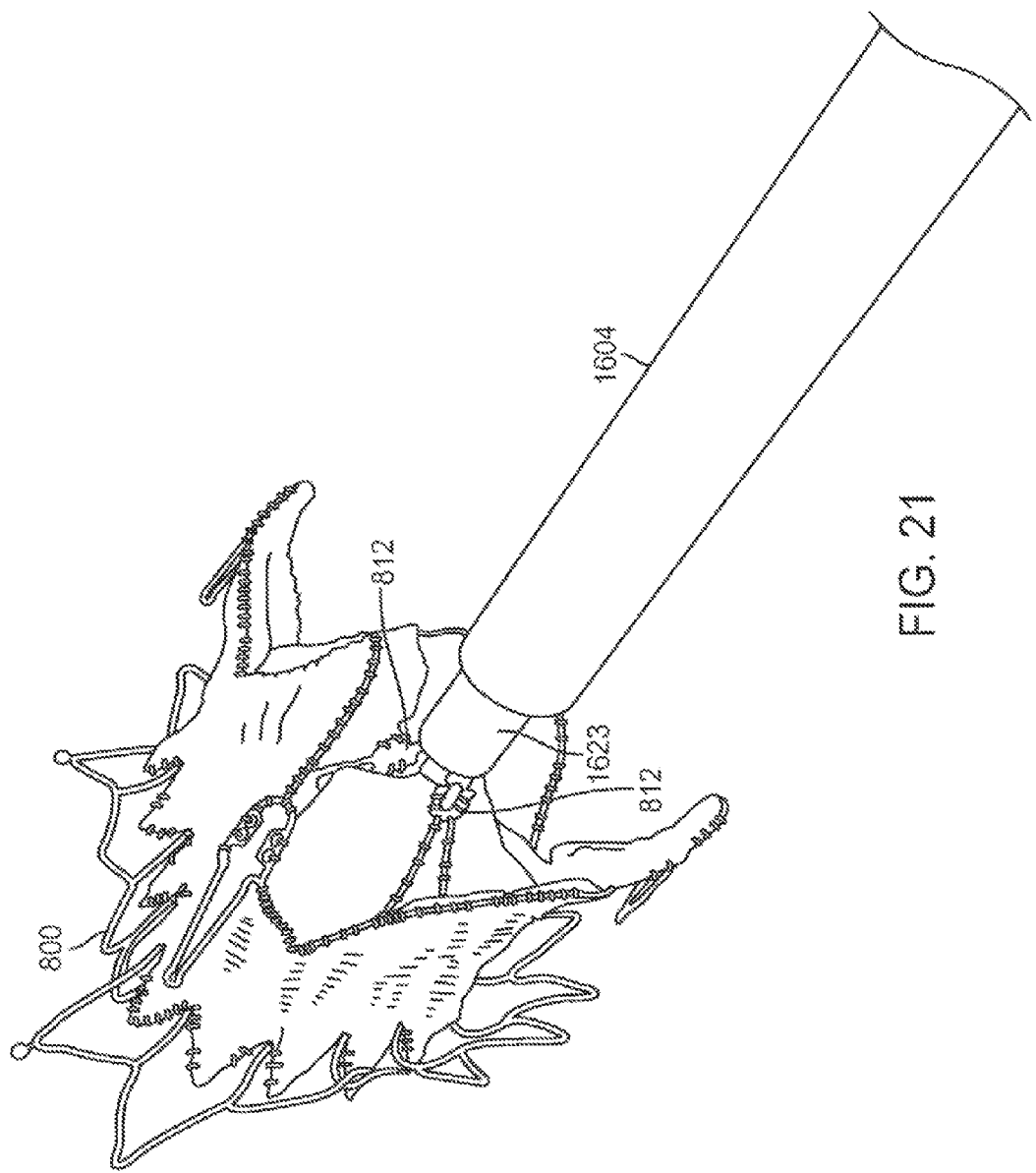

TRANSCATHETER MITRAL VALVE PROSTHESIS

CROSS-REFERENCE TO RELATED APPLICATIONS

This application is a continuation of U.S. patent application Ser. No. 14/046,606, filed Oct. 4, 2013, which is a divisional of U.S. patent application Ser. No. 13/096,572, now U.S. Pat. No. 8,579,964, filed Apr. 28, 2011, which claims the benefit of U.S. Provisional Patent Application Nos. 61/414,879 filed Nov. 17, 2010; 61/393,860 filed Oct. 15, 2010; and 61/331,799 filed May 5, 2010; the entire contents of which are incorporated herein by reference.

BACKGROUND OF THE INVENTION

1. Field of the Invention

The present invention generally relates to medical devices and methods, and more particularly relates to the treatment of valve insufficiency, such as mitral insufficiency, also referred to as mitral regurgitation. The use of prosthetic valves delivered by traditional surgical implantation methods, or by less invasive percutaneous catheter or minimally invasive transapical methods are one possible treatment for valvar insufficiency.

The heart of vertebrate animals is divided into four chambers, and is equipped with four valves (the mitral, aortic, pulmonary and tricuspid valves) that ensure that blood pumped by the heart flows in a forward direction through the cardiovascular system. The mitral valve of a healthy heart prevents the backflow of blood from the left ventricle into the left atrium of the heart, and comprises two flexible leaflets (anterior and posterior) that close when the left ventricle contracts. The leaflets are attached to a fibrous annulus, and their free edges are tethered by subvalvular chordae tendineae to papillary muscles in the left ventricle to prevent them from prolapsing into the left atrium during the contraction of the left ventricle.

Various cardiac diseases or degenerative changes may cause dysfunction in any of these portions of the mitral valve apparatus, causing the mitral valve to become abnormally narrowed or dilated, or to allow blood to leak (i.e. regurgitate) from the left ventricle back into the left atrium. Any such impairments compromise cardiac sufficiency, and can be debilitating or life threatening.

Numerous surgical methods and devices have accordingly been developed to treat mitral valve dysfunction, including open-heart surgical techniques for replacing, repairing or reshaping the native mitral valve apparatus, and the surgical implantation of various prosthetic devices such as annuloplasty rings to modify the anatomy of the native mitral valve. More recently, less invasive transcatheter techniques for the delivery of replacement mitral valve assemblies have been developed. In such techniques, a prosthetic valve is generally mounted in a crimped state on the end of a flexible catheter and advanced through a blood vessel or the body of the patient until the valve reaches the implantation site. The prosthetic valve is then expanded to its functional size at the site of the defective native valve.

While these devices and methods are promising treatments for valvar insufficiency, they can be difficult to deliver, expensive to manufacture, or may not be indicated for all patients. Therefore, it would be desirable to provide improved devices and methods for the treatment of valvar insufficiency such as mitral insufficiency. At least some of these objectives will be met by the devices and methods disclosed below.

2. Description of the Background Art

By way of example, PCT international patent number PCT/US2008/054410 (published as PCT international publication no. WO2008/103722), the disclosure of which is hereby incorporated by reference, describes a transcatheter mitral valve prosthesis that comprises a resilient ring, a plurality of leaflet membranes mounted with respect to the ring so as to permit blood flow therethrough in one direction, and a plurality of tissue-engaging positioning elements movably mounted with respect to the ring and dimensioned to grip the anatomical structure of the heart valve annulus, heart valve leaflets, and/or heart wall. Each of the positioning elements defines respective proximal, intermediate, and distal tissue engaging regions cooperatively configured and dimensioned to simultaneously engage separate corresponding areas of the tissue of an anatomical structure, and may include respective first, second, and third elongate tissue-piercing elements. The valve prosthesis may also include a skirt mounted with respect to the resilient ring for sealing a periphery of the valve prosthesis against a reverse flow of blood around the valve prosthesis.

PCT international patent number PCT/US2009/041754 (published as PCT international publication no. WO2009/134701), the disclosure of which is hereby incorporated by reference, describes a prosthetic mitral valve assembly that comprises an anchor or outer support frame with a flared upper end and a tapered portion to fit the contours of the native mitral valve, and a tissue-based one-way valve mounted therein. The assembly is adapted to expand radially outwardly and into contact with the native heart tissue to create a pressure fit, and further includes tension members anchoring the leaflets of the valve assembly to a suitable location on the heart to function as prosthetic chordae tendineae.

Also known in the prior art are prosthetic mitral valve assemblies that utilize a claw structure for attachment of the prosthesis to the heart (see, for example, U.S. patent application publication no. US2007/0016286 to Hermann et al., the disclosure of which is hereby incorporated by reference), as are prosthetic mitral valve assemblies that rely on the application of axial rather than radial clamping forces to facilitate the self-positioning and self-anchoring of the prosthesis with respect to the native anatomical structure.

Another method which has been proposed as a treatment of mitral valve regurgitation is the surgical bow tie method, which recently has been adapted into a minimally invasive catheter based treatment where an implant is used to clip the valve leaflets together. This procedure is more fully disclosed in the scientific and patent literature, such as in U.S. Pat. No. 6,629,534 to St. Goar et al., the entire contents of which are incorporated herein by reference.

Other relevant publications include U.S. Patent Publication No. 2011/0015731 to Carpentier et al.

BRIEF SUMMARY OF THE INVENTION

The present invention generally relates to medical devices and methods, and more particularly prosthetic valves used to treat mitral regurgitation. While the present disclosure focuses on the use of a prosthetic valve for treating mitral regurgitation, this is not intended to be limiting. The prosthetic valves disclosed herein may also be used to treat other body valves including other heart valves or venous valves. Exemplary heart valves include the aortic valve, the triscupsid valve, or the pulmonary valve.

In embodiments of the present subject matter, transcatheter mitral valve prostheses and transcatheter methods and systems of deploying the same are provided. In certain embodiments, the mitral valve prosthesis comprises a tissue-type prosthetic one-way valve structure comprising a plurality of leaflets affixed within a self-expanding or expandable anchor (i.e. frame) portion having a geometry that expands into a low profile atrial skirt region, an annular region dimensioned to generally conform to a native mitral valve annulus, a ventricular skirt region that displaces the native mitral valve leaflets, and a plurality of leaflet commissures extending into the sub-annular ventricular space (i.e. in the direction of the outflow of blood through the prosthesis) and configured to optimize the efficiency of the prosthetic valve structure and the load distribution on the leaflets thereof. The anchor portion may also in preferred embodiments be asymmetrical along its longitudinal axis, with the atrial skirt region, the annular region and/or the ventricular skirt region having differently configured anterior and posterior aspects in order to facilitate close accommodation of the asymmetrical contours and features of a typical native mitral valve apparatus. This asymmetry may result inherently from the structural configuration of the anchor portion as discussed further below, and/or as a consequence of shaping or forming steps employed during the manufacturing process.

The prosthetic valve structure in preferred embodiments may comprise a bicuspid or tricuspid valve in order, in part, to simplify manufacture of the mitral valve prosthesis, but as would be readily apparent to those of skill in the art, other configurations are possible. The leaflets may be fabricated from a single piece or from multiple pieces of standard biologic prosthetic materials, such as cryo- or chemically-preserved pericardium (e.g. bovine, equine, porcine, caprine, kangaroo), or from standard suitable synthetic prosthetic materials (e.g. fiber-reinforced matrix materials) well known in the art, and may be sewn or otherwise adhered to the anchor to form the valve leaflets in any standard suitable manner.

To optimize prosthetic valve efficiency and the load distribution on the prosthetic leaflets, the commissures extend generally axially in a cantilevered fashion downstream into the sub-annular space, and are capable of flexing radially and laterally along their axial lengths to distribute the forces associated with blood flow through the prosthetic valve structure. In some embodiments, the commissures define (when the mitral valve prosthesis is in an expended state) a somewhat frustoconical aperture that narrows along the forward direction of blood flow in order to aid in the closure of the prosthetic valve structure during contraction of the ventricle. To further optimize efficiency and load distribution on the leaflets, the commissures may be shaped and dimensioned so as to provide for the attachment of the leaflets along arcuate seams, and may also be made selectively flexible at different points or zones along their axial length through, for example, the addition or deletion of reinforcing struts, or through variation of the thickness of the commissures in selected regions.

The anchor portion of the mitral valve prosthesis is preferably fabricated from a single piece of metallic material that has been cut so as to permit the mitral valve prosthesis to be compressed into a compact, generally tubular delivery configuration, and expanded into the deployment configuration further described herein. In self-expanding embodiments, the anchor portion of the mitral valve prosthesis may be fabricated from a shape memory alloy (SMA) such as the nickel-titanium alloy nitinol, and in expandable embodiments, the anchor portion may be fabricated from any metallic material, such as chromium alloy or stainless steel, that is suitable for implantation into the body. In some embodiments, the metallic material may be of a single thickness throughout entirety of the anchor portion, and in others may vary in thickness so as to facilitate variations in the radial force that is exerted by the anchor portion in specific regions thereof, to increase or decrease the flexibility of the anchor portion in certain regions, and/or to control the process of compression in preparation for deployment and the process of expansion during deployment.

When deployed, the atrial skirt region of the mitral valve prosthesis extends generally radially outwards so as to lie flat against and cover the atrial surface of the native mitral valve annulus, and to anchor the mitral valve prosthesis against at least a portion of the adjoining atrial surface of the heart. The atrial skirt region has a low axial profile (extending only slightly into the atrium of the heart) in order to minimize potentially thrombogenic turbulence in blood flow, and in preferred embodiments, may be covered with standard biologic or synthetic prosthetic materials of the sort described above in order to seal the atrial skirt region against the atrial surface and to facilitate the funnelling of atrial blood through the mitral valve prosthesis. In some embodiments, the atrial skirt region further comprises atrial barbs or prongs to further facilitate the anchoring of the deployed prosthesis to the atrial heart surface. To facilitate the orientation and alignment of the mitral valve prosthesis within the native mitral valve upon deployment, particularly in embodiments where the anchor portion is longitudinally asymmetrical, the atrial skirt region of the anchor portion of the mitral valve prosthesis may preferably further comprise an alignment structure that may be differentiated (such as by angiography, computed tomography, etc.) from the remainder of the atrial skirt region and thereby used as an orientation guide during deployment. Most preferably, the alignment structure may comprise an elongation of the anterior aspect of the atrial skirt region configured to expand radially to accommodate the aortic root portion of the atrial surface.

The annular region of the mitral valve prosthesis is dimensioned, as noted above, to generally conform to and anchor against a native mitral valve annulus when deployed. In preferred embodiments, the deployed annular region may define a generally D-shaped annulus suitable for fitting the contours of a typical native mitral valve, and may be covered with standard biologic or synthetic prosthetic materials of the sort previously described to seal the annular region against the native mitral valve annulus.

The ventricular skirt region expands when deployed in the ventricular space generally radially outwards against the native mitral valve, but not so far as to obstruct the left ventricular outflow tract, nor to contact the ventricular wall. To anchor the mitral valve prosthesis against the displaced native leaflets in the ventricular space, the maximal radial displacement of the fully deployed ventricular skirt region is selected to be slightly greater than the circumference of the native mitral valve. In preferred embodiments, the ventricular skirt region also comprises ventricular and/or native leaflet barbs or prongs to further anchor the deployed prosthesis thereto. Most preferably, the ventricular skirt region is asymmetrical and the prongs thereof comprise two trigonal anchoring tabs located in the anterior aspect of the ventricular skirt region for anchoring against the fibrous trigones on either side of the anterior leaflet of the native mitral valve, and one posterior ventricular anchoring tab located in the posterior aspect of the ventricular skirt region for anchoring over the posterior leaflet of the native mitral valve. Associated with these tabs are deployment control regions as described in further detail below.

The ventricular skirt region may also in some embodiments be covered with standard biologic or synthetic prosthetic materials of the sort previously described in order to seal the ventricular skirt region against the displaced native leaflets, and thereby to funnel ventricular blood (during contraction of the ventricle) towards the prosthetic valve structure to assist in the closure thereof during contraction of the ventricle.

The combined 3-zone anchoring of the mitral valve prosthesis against the atrial surface, the native valve annulus, and the displaced native leaflets (supplemented, in preferred embodiments by a fourth zone of anchoring from the trigonal and posterior ventricular anchoring) in the ventricular space prevents the prosthesis from migrating or dislodging from within the native valve annulus during the contraction of the atrium or the ventricle, and lessens the anchoring pressure that is required to be applied in any given anchoring zone as compared to a prosthesis that is anchored in only a single anchoring zone, or in any combination of these four anchoring zones. The consequent reduction in radial force required to be exerted against the native structures in each zone minimizes the risk of obstruction or impingement of the nearby aortic valve or aortic root caused by the displacement of the native mitral valve apparatus. The combined 3 or 4-zone anchoring of the mitral valve prosthesis also facilitates the positioning and/or re-positioning of the mitral valve prosthesis as described below.

To deploy the mitral valve prosthesis within the native mitral valve apparatus, the prosthesis is first compacted and loaded into a suitably-adapted conventional catheter delivery system of the sort well known to those of skill in the art. Preferably, to facilitate later deployment, the commissures and associated prosthetic valve structure of the prosthesis are captured within an inner lumen of the catheter delivery system, and the remaining portions of the anchor region are captured within a secondary outer lumen of the catheter delivery system. The loaded mitral valve prosthesis may then be delivered (typically either transseptally or transapically) in its compacted form into the left atrium of the heart using a conventional catheter delivery system. The prosthesis is releasably attached to the catheter delivery system via its commissures, and shielded by the (preferably dual-lumen) delivery sheath thereof during transit into the atrial space. Once the prosthesis has been guided into the left atrium, the delivery sheath of the catheter delivery system is retracted as described below in order to permit expansion of the various regions of the prosthesis to proceed. Of course, in self-expanding embodiments, expansion of the prosthesis will occur spontaneously upon retraction of the delivery sheath, and in expandable embodiments, a catheter inflation structure such as a balloon is required to effect the expansion.

Deployment of the mitral valve prosthesis may proceed differently depending upon the features of the particular embodiment of the prosthesis being deployed. For example, in asymmetrical embodiments that comprise trigonal anchoring tabs and a posterior ventricular anchoring tab in the ventricular skirt region (as well as, preferably, an alignment structure in the atrial region), these tabs may preferably be deployed before deployment of the remaining portions of the ventricular skirt regions in order to facilitate the anchoring of these tabs against the native fibrous trigones and posterior leaflet, respectively.

In the first general deployment step, the atrial skirt region of the mitral valve prosthesis is permitted to expand by retracting the corresponding portion of the catheter delivery sheath (or is balloon-expanded following the retraction of the corresponding portion of the delivery sheath) within the left atrium of the heart, and the expanded atrial skirt region is then positioned over the atrial surface of the native mitral valve and anchored against at least a portion of the adjoining atrial surface of the heart. In preferred embodiments where the atrial skirt region comprises an alignment structure, this first general deployment step may be further broken down into two sub-steps, wherein the catheter delivery sheath is first retracted only so far as to permit expansion of the alignment structure (so that it may be visualized to facilitate manipulation of the delivery system in such a way as to orient the mitral valve prosthesis into a desired position), and then, once initial alignment of the prosthesis appears to be satisfactory, further retracted to permit the expansion, positioning and anchoring of the remaining portions of the atrial skirt region. In embodiments where the alignment structure comprises an elongation of the anterior aspect of the atrial skirt region, such initial alignment comprises the rotation and/or alignment of the alignment structure so that it is situated adjacent the aortic root and between the fibrous trigones of the native anterior leaflet.

Next, the annular region of the prosthesis is permitted to expand by further retraction of the catheter delivery sheath so as to engage the native mitral valve annulus (i.e. to contact the native valve annulus throughout at least a majority thereof) in order to create a second anchoring zone and to create a suitable opening for blood flow through the prosthetic valve structure.

Then, in embodiments that comprise trigonal anchoring tabs and a posterior ventricular anchoring tab in the ventricular skirt region, the catheter delivery sheath is further retracted so far as to permit the tabs to expand while the remainder of the ventricular skirt region of the prosthesis, including the deployment control regions of the tabs, remain sheathed. With the deployment control regions still retained within the delivery system and the atrial skirt region anchored against the atrial surface, the tabs project radially outward to facilitate engagement with the corresponding features of the native mitral valve. The posterior ventricular anchoring tab is aligned in the middle of the posterior leaflet of the mitral valve where there is an absence of chordae attachments to the posterior leaflet, and passed over the posterior leaflet to seat between the posterior leaflet and the ventricular wall. The two trigonal anchoring tabs are positioned on either side of the anterior leaflet with their heads positioned at the fibrous trigones. Slight rotation and realignment of the prosthesis can occur at this time.

Once the assembly has been satisfactorily positioned and the tabs aligned, the catheter delivery sheath may be further retracted to permit expansion of the remaining portions of the ventricular skirt region to secure the prosthesis within the mitral apparatus and seal the mitral annulus. Complete retraction of the outer catheter delivery sheath releases the ventricular skirt region and allows the anchoring tabs to proximate their anchoring location. As the prosthesis expands, the trigonal tabs anchor against the fibrous trigones, capturing the native anterior leaflet and chordae between the tabs and the anterior surface of the prosthetic valve assembly, and the posterior ventricular tab anchors between the ventricular wall and the posterior leaflet, capturing the posterior leaflet between the posterior anchoring tab and the posterior surface of the prosthetic valve assembly. The remaining portions of the ventricular skirt region expand out against the native mitral valve leaflets and adjacent anatomy, thereby creating a sealing funnel within the native leaflets and displacing the native leaflets from the prosthetic commissures to avoid obstruction of the prosthetic valve function. With the commissures of the prosthesis still captured within the delivery system, very minor adjustments may still made to ensure accurate positioning, anchoring and sealing.

In embodiments that do not comprise trigonal anchoring tabs and a posterior ventricular anchoring tab in the ventricular skirt region, the retraction of the catheter delivery sheath from the ventricular skirt region may, of course, be performed in one step after the atrial skirt and annular regions of the prosthesis have been initially anchored, to permit the ventricular skirt region of the prosthesis to expand against the native mitral valve, and to additionally anchor the prosthesis against the displaced native leaflets in the ventricular space. Optionally, the mitral valve prosthesis, which is still at this point releasably attached to the catheter delivery system via its commissures, may be driven slightly further downstream into ventricular space to create a greater seating force as between the atrial skirt region and atrial surface of the heart, and to provide additional purchase for any ventricular and/or native leaflet barbs or prongs that may be present in the ventricular skirt region. In embodiments where one or more of the atrial skirt region, the annular region and the ventricular skirt region are covered with a suitable biologic or synthetic prosthetic material, a seal may also be formed between the respective regions of the prosthesis and the associated zone of the native mitral valve apparatus.

Finally, once satisfactory positioning of the prosthesis has been achieved, the commissures are released from the catheter delivery system, allowing the catheter delivery system to be withdrawn, and leaving the mitral valve prosthesis in place as a functional replacement for the native mitral valve apparatus. Upon release of the commissures, the prosthesis may further undergo a final stage of foreshortening and seating as any remaining pressure exerted by the delivery system is released. The atrial skirt region may recoil slightly from this release in pressure, pulling the prosthesis slightly further up in to the left atrium, and thereby further seating the ventricular skirt region, including any associated barbs, prongs or tabs. In embodiments that comprise trigonal anchoring tabs, the seating thereof pulls the captured anterior leaflet tightly against the prosthesis, thereby avoiding or minimizing obstruction of the Left Ventricular Outflow Tract (LVOT), and firmly seats the ventricular skirt region in the annulus to prevent paravalvular leakage. Once final deployment is complete, the delivery system is retracted and removed.

In a first aspect of the present invention, a method of anchoring a prosthetic valve in a patient's heart comprises providing the prosthetic valve, wherein the prosthetic valve comprises an anchor having an atrial skirt, an annular region, a ventricular skirt, and a plurality of valve leaflets, wherein the anchor has a collapsed configuration for delivery to the heart and an expanded configuration for anchoring with the heart, and positioning the prosthetic valve in the patient's heart. The method also comprises expanding the atrial skirt radially outward so as to lie over a superior surface of the patient's native mitral valve, anchoring the atrial skirt against a portion of the atrium, and radially expanding the annular region of the anchor to conform with and to engage the native mitral valve annulus. The method also comprises radially expanding the ventricular skirt thereby displacing the native mitral valve leaflets radially outward.

At least a portion of the prosthetic valve may be covered with tissue or a synthetic material. Positioning the prosthetic valve may comprise transseptally delivering the prosthetic valve from the right atrium to the left atrium of the heart, or transapically delivering the prosthetic valve from a region outside the heart to the left ventricle of the heart.

Expanding the atrial skirt may comprise slidably moving a restraining sheath away from the atrial skirt thereby allowing radial expansion thereof. The atrial skirt may self-expand when the restraining sheath is removed therefrom. The method may further comprise applying a force on the prosthetic valve to ensure that the atrial skirt engages the superior surface of the mitral valve. The atrial skirt may comprise a plurality of barbs, and expanding the atrial skirt may comprise anchoring the barbs into the superior surface of the mitral valve. Expanding the atrial skirt may comprise sealing the atrial skirt against the superior surface of the native mitral valve.

Radially expanding the annular region may comprise slidably moving a restraining sheath away from the annular region thereby allowing radial expansion thereof. The annular region may self-expand when the restraining sheath is removed therefrom. Radially expanding the annular region may comprise asymmetrically expanding the annular region such that an anterior portion of the annular region is substantially flat, and a posterior portion of the annular region is cylindrically shaped.

The ventricular skirt may further comprise a trigonal anchoring tab on an anterior portion of the ventricular skirt, and radially expanding the ventricular skirt may comprise anchoring the trigonal anchoring tab against a first fibrous trigon on a first side of the anterior leaflet of the native mitral valve. The native anterior leaflet and adjacent chordae tendineae may be captured between the trigonal anchoring tab and an anterior surface of the anchor. The ventricular skirt may further comprise a second trigonal anchoring tab on the anterior portion of the ventricular skirt, and wherein radially expanding the ventricular skirt may comprise anchoring the second trigonal anchoring tab against a second fibrous trigon opposite the first fibrous trigon. The native anterior leaflet and adjacent chordae tendineae may be captured between the second trigonal anchoring tab and an anterior surface of the anchor. The ventricular skirt may further comprise a posterior ventricular anchoring tab on a posterior portion of the ventricular skirt. Radially expanding the ventricular skirt may comprise anchoring the posterior ventricular anchoring tab over a posterior leaflet of the native mitral valve to seat between the posterior leaflet and a ventricular wall of the heart. Radially expanding the ventricular skirt may comprise slidably moving a restraining sheath away from the ventricular skirt thereby allowing radial expansion thereof. The ventricular skirt may self-expand when the restraining sheath is removed therefrom.

The ventricular skirt may comprise a plurality of barbs, and expanding the ventricular skirt may comprise anchoring the barbs into heart tissue. The prosthetic valve may comprise a plurality of prosthetic valve leaflets, and radially expanding the ventricular skirt may comprise displacing the native mitral valve leaflets radially outward thereby preventing interference of the native mitral valve leaflets with the prosthetic valve leaflets. Radially expanding the ventricular skirt may comprise displacing the native mitral valve leaflets radially outward without contacting a ventricular wall, and without obstructing a left ventricular outflow tract. Radially expanding the ventricular skirt may comprise asymmetrically expanding the ventricular skirt such that an anterior portion of the ventricular skirt is substantially flat, and a posterior portion of the ventricular skirt is cylindrically shaped.

The atrial skirt may comprise an alignment element, and the method may comprise aligning the alignment element relative to the patient's valve. The valve may comprise a mitral valve, and aligning may comprise aligning the alignment element with an aortic root and disposing the alignment between two fibrous trigones of an anterior leaflet of the mitral valve. Aligning may comprise rotating the prosthetic valve. The prosthetic valve may comprise a plurality of prosthetic leaflets coupled to one or more commissures, and the method may comprise releasing the commissures from a delivery catheter. The prosthetic valve may comprise a tricuspid leaflet configuration.

The prosthetic valve may have an open configuration in which the prosthetic valve leaflets are disposed away from one another, and a closed configuration in which the prosthetic valve leaflets engage one another. Blood flows freely through the prosthetic valve in the open configuration, and retrograde blood flow across the prosthetic valve is substantially prevented in the closed configuration. The method may comprise reducing or eliminating mitral regurgitation. The prosthetic valve may comprise a therapeutic agent, and the method may comprise eluting the therapeutic agent from the prosthetic valve into adjacent tissue.

In another aspect of the present invention, a prosthetic cardiac valve comprises an anchor having an atrial skirt, an annular region, and a ventricular skirt. The anchor has a collapsed configuration for delivery to the heart and an expanded configuration for anchoring the prosthetic cardiac valve to a patient's heart. The prosthetic valve also comprises a plurality of prosthetic valve leaflets, each of the leaflets having a first end and a free end, wherein the first end is coupled with the anchor and the free end is opposite of the first end. The prosthetic cardiac valve has an open configuration in which the free ends of the prosthetic valve leaflets are disposed away from one another to allow antegrade bloodflow therepast, and a closed configuration in which the free ends of the prosthetic valve leaflets engage one another and substantially prevent retrograde bloodflow therepast.

At least a portion of the atrial skirt may be covered with tissue or a synthetic material. The atrial skirt may further comprise a plurality of barbs coupled thereto, the plurality of barbs adapted to anchor the atrial skirt into a superior surface of the patient's mitral valve. The atrial skirt may comprise a collapsed configuration and an expanded configuration. The collapsed configuration may be adapted for delivery to the patient's heart, and the expanded configuration may be radially expanded relative to the collapsed configuration and adapted to lie over a superior surface of the patient's native mitral valve, thereby anchoring the atrial skirt against a portion of the atrium. The atrial skirt may self-expand from the collapsed configuration to the radially expanded configuration when unconstrained. The atrial skirt may comprise one more radiopaque markers. The atrial skirt may comprise a plurality of axially oriented struts connected together with a connector element thereby forming a series of peaks and valleys. Some of the peaks and valleys may extend axially outward further than the rest of the atrial skirt, thereby forming an alignment element.

At least a portion of the annular region may be covered with tissue or a synthetic material. The annular region may have a collapsed configuration and an expanded configuration. The collapsed configuration may be adapted for delivery to the patient's heart, and the expanded configuration may be radially expanded relative to the collapsed configuration and adapted to conform with and to engage the native mitral valve annulus. The annular region may self-expand from the collapsed configuration to the expanded configuration when unconstrained. The annular region may comprise an asymmetrically D-shaped cross-section having a substantially flat anterior portion, and a cylindrically shaped posterior portion. The annular region may comprise a plurality of axially oriented struts connected together with a connector element thereby forming a series of peaks and valleys. One or more of the axially oriented struts may comprise one or more suture holes extending therethrough, the suture holes sized to receive a suture.

At least a portion of the ventricular skirt may be covered with tissue or a synthetic material. The ventricular skirt may comprise an asymmetrically D-shaped cross-section having a substantially flat anterior portion, and a cylindrically shaped posterior portion. The ventricular skirt may have a collapsed configuration and an expanded configuration. The collapsed configuration may be adapted for delivery to the patient's heart, and the expanded configuration may be radially expanded relative to the collapsed configuration and adapted to displace the native mitral valve leaflets radially outward. The ventricular skirt may self-expand from the collapsed configuration to the expanded configuration when unconstrained.

The ventricular skirt may further comprise a trigonal anchoring tab disposed on an anterior portion of the ventricular skirt. The trigonal anchoring tab may be adapted to being anchored against a first fibrous trigon on a first side of an anterior leaflet of the patient's mitral valve. Thus, the anterior leaflet and adjacent chordae tendineae may be captured between the trigonal anchoring tab and an anterior surface of the anchor. The ventricular skirt may further comprise a second trigonal anchoring tab that may be disposed on the anterior portion of the ventricular skirt. The second trigonal anchoring tab may be adapted to being anchored against a second fibrous trigon opposite the first fibrous trigon, such that the anterior leaflet and adjacent chordae tendineae are captured between the second trigonal anchoring tab and the anterior surface of the anchor. The ventricular skirt may further comprise a posterior ventricular anchoring tab disposed on a posterior portion of the ventricular skirt. The posterior ventricular anchoring tab may be adapted to being anchored over a posterior leaflet of the patient's mitral valve, such that the posterior ventricular anchoring tab is seated between the posterior leaflet and a ventricular wall of the patient's heart. The ventricular skirt may further comprise a plurality of barbs coupled thereto, and that may be adapted to anchor the ventricular skirt into heart tissue. The ventricular skirt may comprise a plurality of struts connected together with a connector element thereby forming a series of peaks and valleys. The one or more struts may comprise one or more suture holes extending therethrough, and that may be sized to receive a suture.

The plurality of prosthetic valve leaflets may comprise a tricuspid leaflet configuration. At least a portion of the one or more prosthetic valve leaflets may comprise tissue or a synthetic material. One or more of the plurality of prosthetic valve leaflets may be disposed over one or more commissure posts or struts that are radially biased inward relative to the ventricular skirt. The one or more commissure posts or struts may comprise one or more suture holes extending therethrough and that may be sized to receive a suture. The one or more prosthetic valve leaflets may be coupled to a commissure post or strut having a commissure tab adapted to releasably engage the commissure post or strut with a delivery device.

The prosthetic cardiac valve may further comprise an alignment element coupled to an anterior portion of the anchor. The alignment element may be adapted to be aligned with an aortic root of the patient's heart and disposed between two fibrous trigones of an anerior leaflet of the patient's mitral valve. The alignment element may be coupled with the atrial skirt. The prosthetic cardiac valve may further comprise a therapeutic agent coupled thereto, and adapted to being controllably eluted therefrom.

In still another aspect of the present invention, a delivery system for delivering a prosthetic cardiac valve to a patient's heart comprises an inner guidewire shaft having a lumen extending therethrough and adapted to slidably receive a guidewire, and a hub shaft concentrically disposed over the inner guidewire shaft. The delivery system also comprises a bell shaft slidably and concentrically disposed over the hub shaft, a sheath slidably and concentrically disposed over the bell shaft, and a handle near a proximal end of the delivery system. The handle comprises an actuator mechanism adapted to advance and retract the bell shaft and the sheath.

The system may further comprise the prosthetic cardiac valve which may be housed in the sheath in a radially collapsed configuration. The prosthetic cardiac valve may comprise an anchor having an atrial skirt, an annular region, and a ventricular skirt. The prosthetic valve may also comprise a plurality of prosthetic valve leaflets. Each of the leaflets may have a first end and a free end. The first end may be coupled with the anchor and the free end may be opposite of the first end. The prosthetic cardiac valve may have an open configuration in which the free ends of the prosthetic valve leaflets are disposed away from one another to allow antegrade bloodflow therepast. The valve may have a closed configuration in which the free ends of the prosthetic valve leaflets engage one another and substantially prevent retrograde blood flow therepast.

Proximal retraction of the sheath relative to the bell shaft may remove a constraint from the prosthetic cardiac valve thereby allowing the prosthetic cardiac valve to self-expand into engagement with the patient's native heart tissue. The prosthetic cardiac valve may be releasably coupled with the hub shaft, and proximal retraction of the bell shaft relative to the hub shaft may release the prosthetic cardiac valve therefrom. The actuator mechanism may comprise a rotatable wheel. The system may further comprise a tissue penetrating distal tip coupled to the hub shaft. The tissue penetrating distal tip may be adapted to pass through and expand an incision in the patient's heart. The system may further comprise a pin lock mechanism releasably coupled with the handle. The pin lock mechanism may limit proximal retraction of the sheath.

These and other embodiments are described in further detail in the following description related to the appended drawing figures.

BRIEF DESCRIPTION OF THE DRAWINGS

In the drawings, like reference numerals designate like or similar steps or components.

FIGS. 15A-15C are cross-sectional views of a distal portion of the delivery device in FIG. 11.

FIGS. 19A-19B are side views of the delivery device in FIG. 16 during various stages of operation.

FIG. 21 illustrates engagement of the delivery device in FIG. 16 with the prosthetic valve of FIG. 8A.

DETAILED DESCRIPTION OF THE INVENTION

Specific embodiments of the disclosed device, delivery system, and method will now be described with reference to the drawings. Nothing in this detailed description is intended to imply that any particular component, feature, or step is essential to the invention.

Figure 1:
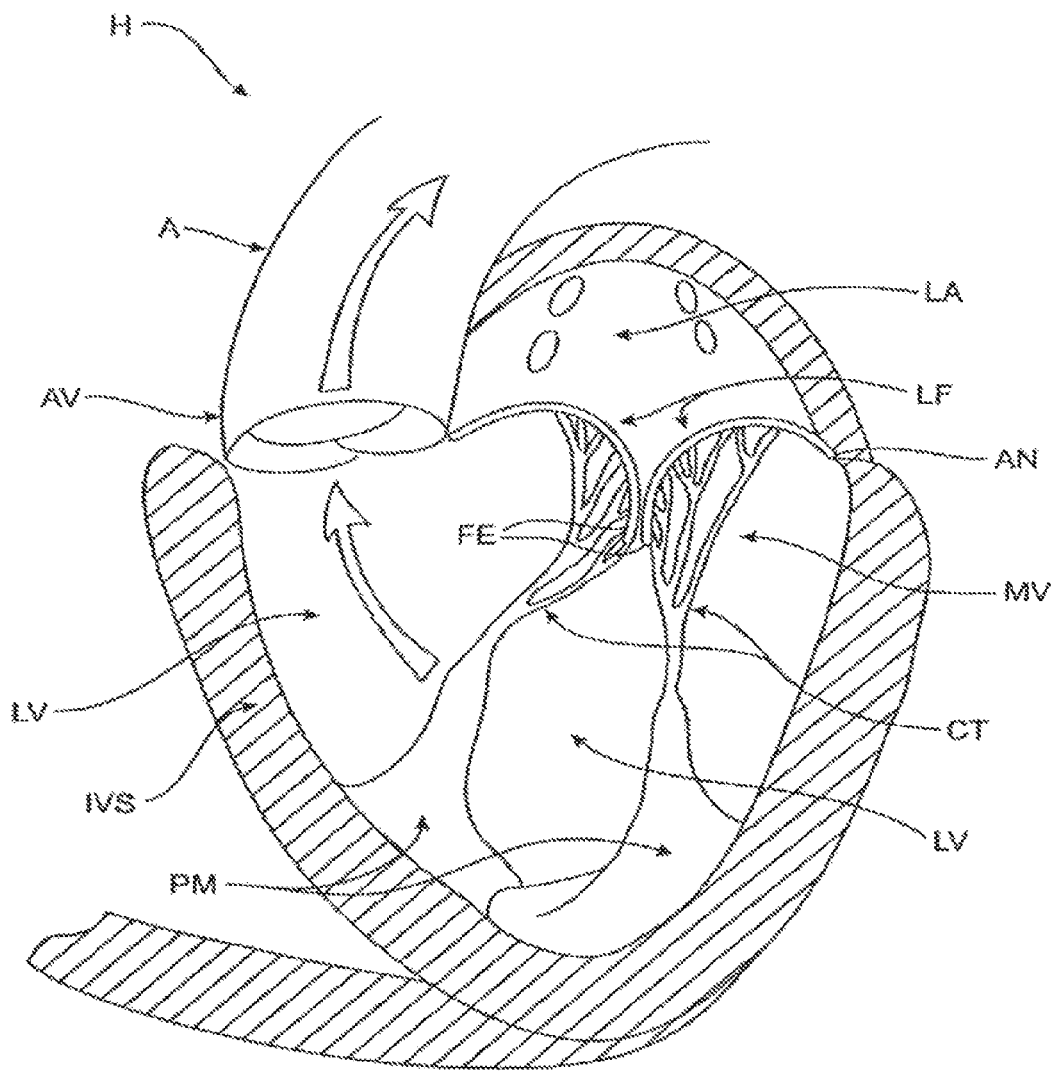
FIG. 1 is a schematic illustration of the left ventricle of a heart showing blood flow during systole with arrows.

Cardiac Anatomy. The left ventricle LV of a normal heart H in systole is illustrated in FIG. 1. The left ventricle LV is contracting and blood flows outwardly through the aortic valve AV, a tricuspid valve in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendineae CT (also referred to herein as the chordae) which include a plurality of branching tendons secured over the lower surfaces of each of the valve leaflets LF. The chordae CT in turn, are attached to the papillary muscles PM which extend upwardly from the lower portions of the left ventricle and interventricular septum IVS.

Figure 2:
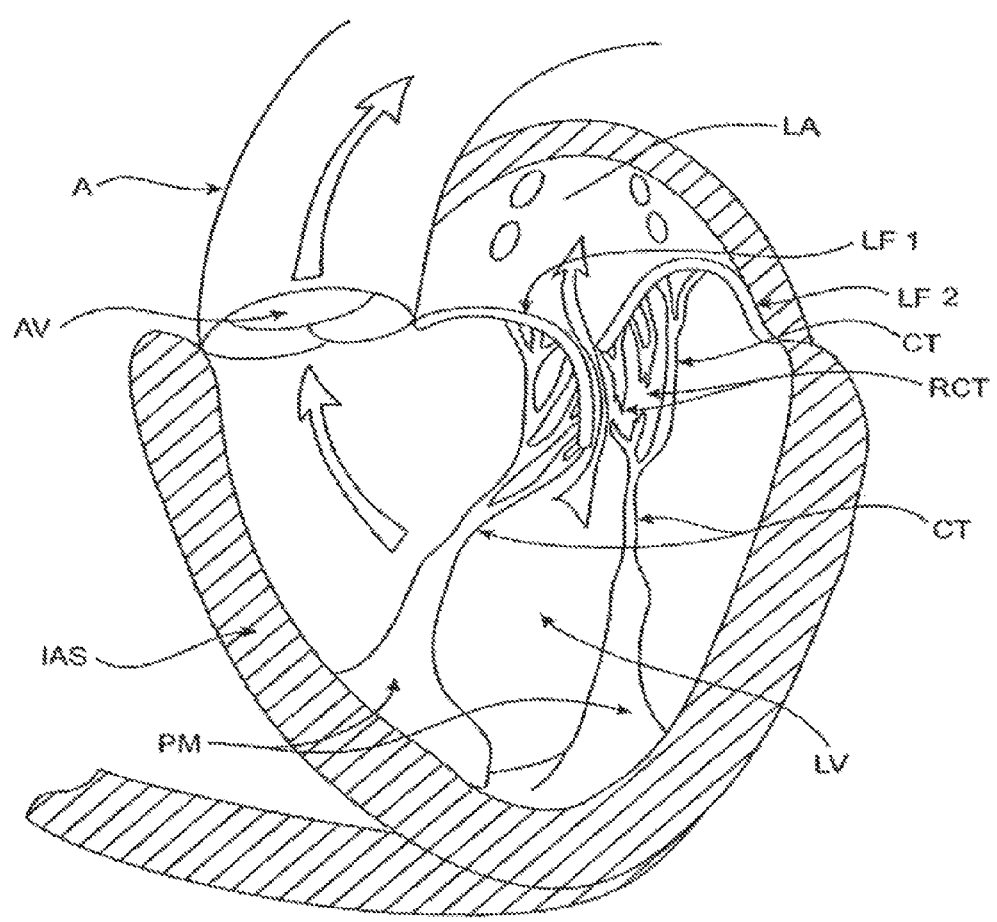
FIG. 2 is a schematic illustration of the left ventricle of a heart having prolapsed leaflets in the mitral valve.
Figure 3:
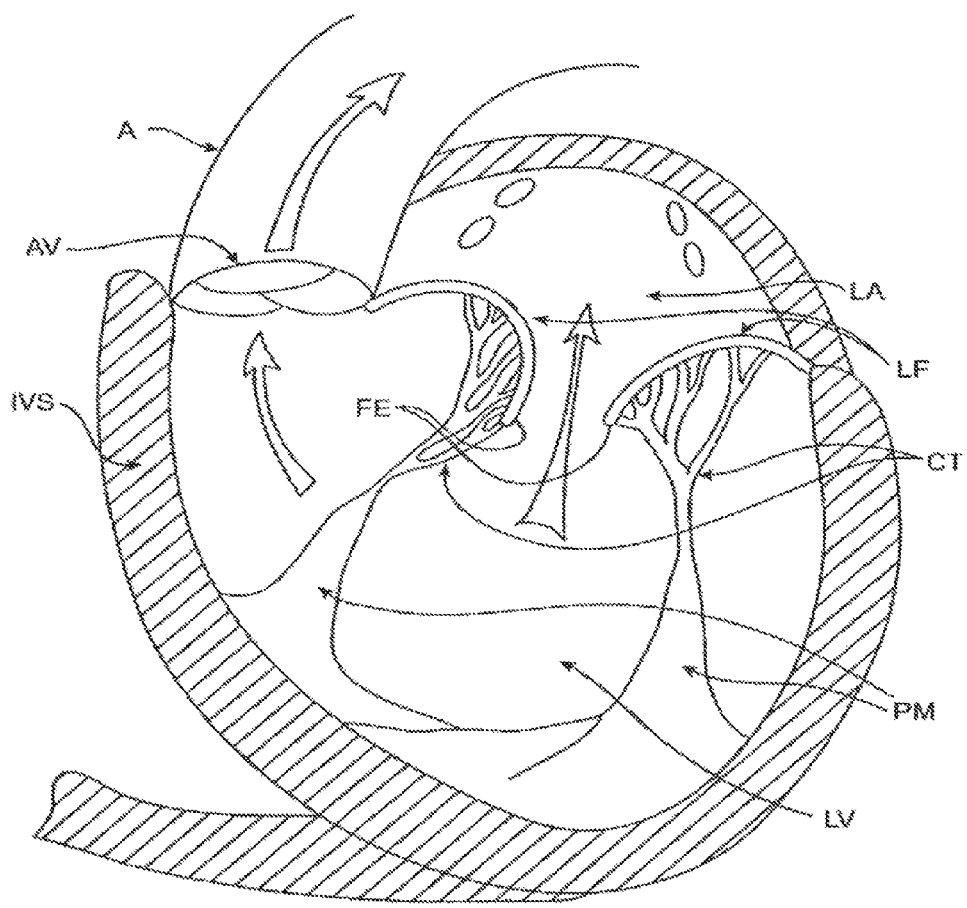
FIG. 3 is a schematic illustration of a heart in a patient suffering from cardiomyopathy where the heart is dilated and the leaflets do not meet.
Figure 4:
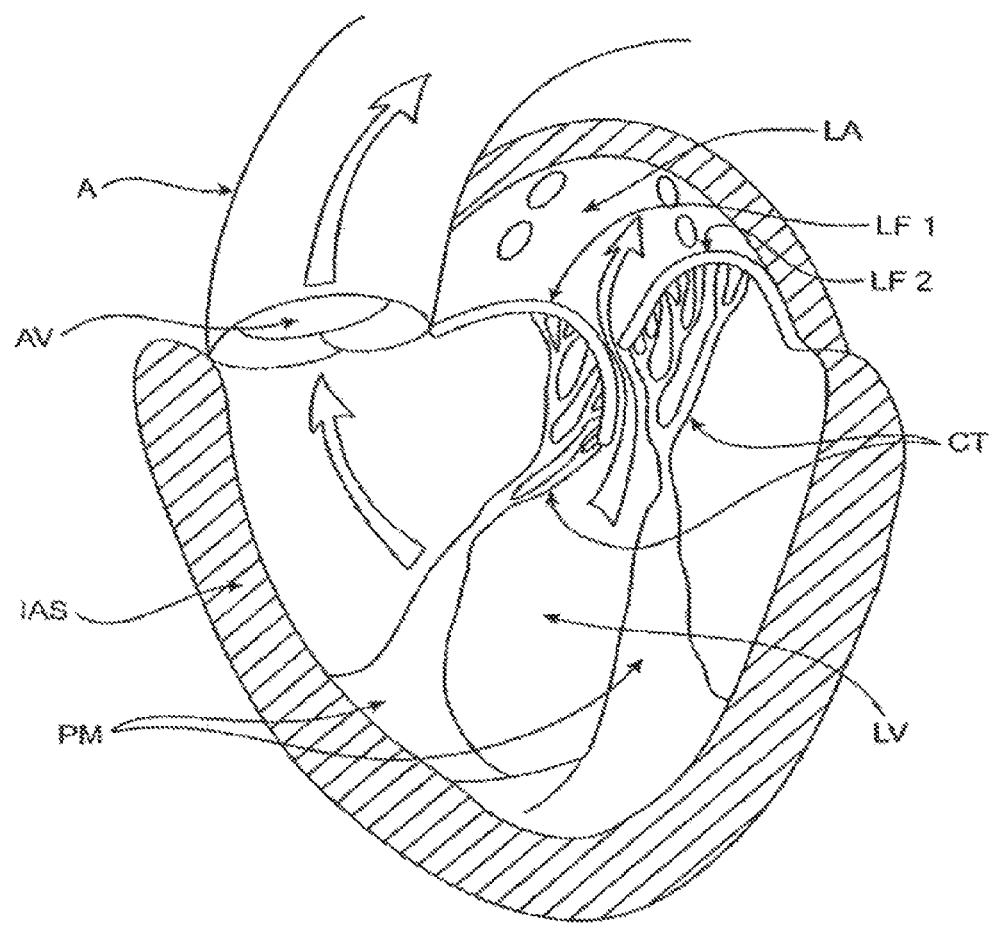
FIG. 4 illustrates mitral valve regurgitation in the left ventricle of a heart having impaired papillary muscles.

Referring now to FIGS. 2-4, a number of structural defects in the heart can cause mitral prolapse since inadequate tension is transmitted to the leaflet via the chordae. While the other leaflet LF1 maintains a normal profile, the two valve leaflets do not properly meet and leakage from the left ventricle LV into the left atrium LA will occur, as shown by the arrow.

Figure 3A:
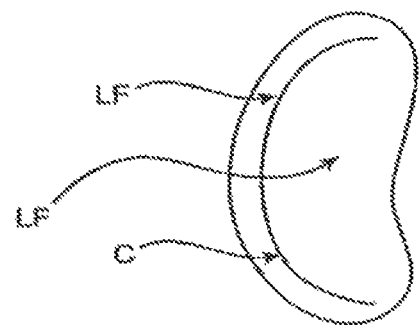
FIG. 3A shows, normal closure of the leaflets.
Figure 3B:
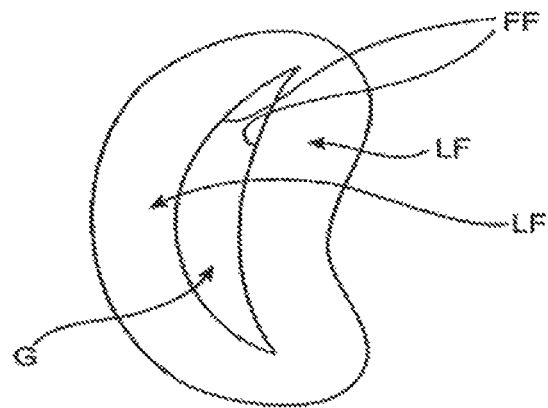
FIG. 3B shows abnormal closure in the dilated heart.

Regurgitation also occurs in the patients suffering from cardiomyopathy where the heart is dilated and the increased size prevents the valve leaflets LF from meeting properly, as shown in FIG. 3. The enlargement of the heart causes the mitral annulus to become enlarged, making it impossible for the free edges FE to meet during systole. The free edges of the anterior and posterior leaflets normally meet along a line of coaptation C as shown in FIG. 3A, but a significant gap G can be left in patients suffering from cardiomyopathy, as shown in FIG. 3B.

Mitral valve regurgitation can also occur in patients who have suffered ischemic heart disease where the functioning of the papillary muscles PM is impaired, as illustrated in FIG. 4. As the left ventricle LV contracts during systole, the papillary muscles PM do not contract sufficiently to effect proper closure. The leaflets LF1 and LF2 then prolapse, as illustrated. Leakage again occurs from the left ventricle LV to the left atrium LA, as shown by the arrow.

Figure 5A:
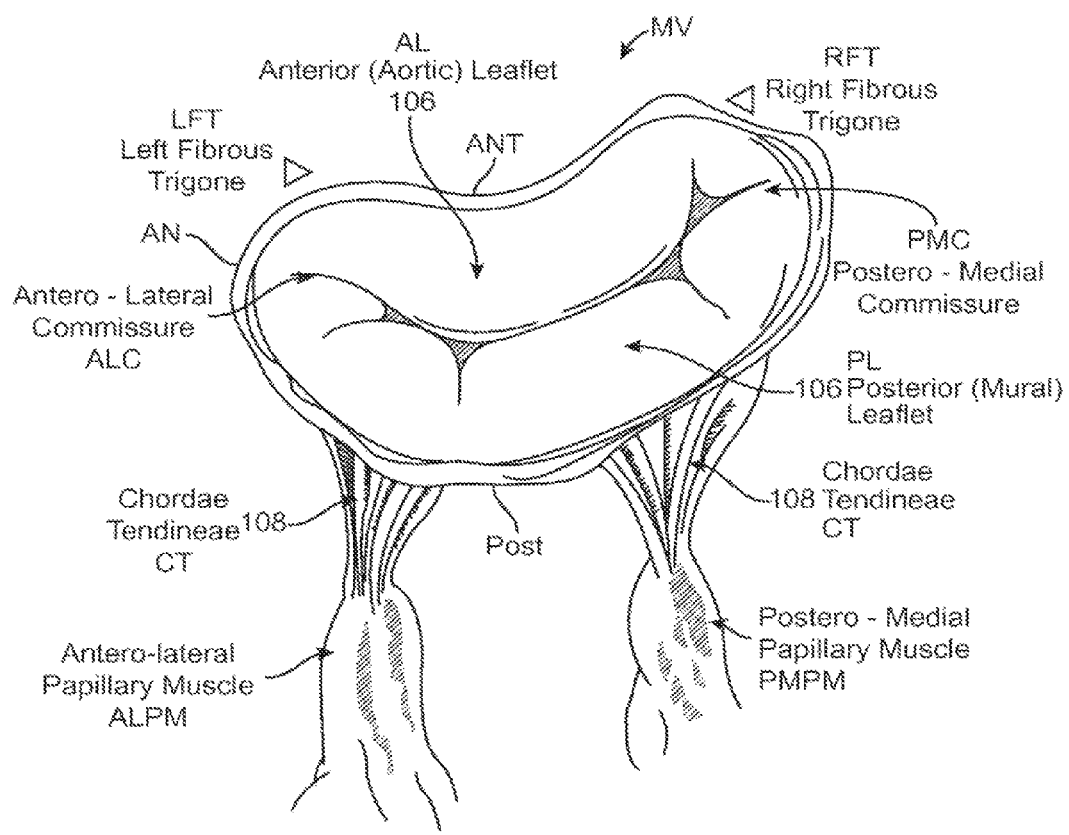
FIGS. 5A-5B illustrate the mitral valve.
Figure 5B:
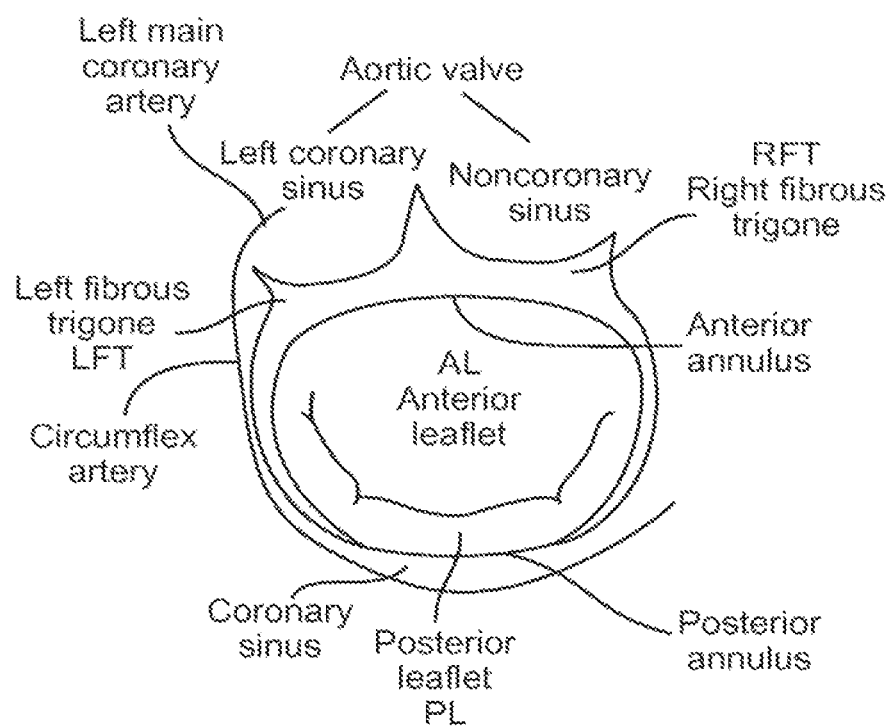

FIG. 5A more clearly illustrates the anatomy of a mitral valve MV which is a bicuspid valve having an anterior side ANT and a posterior side POST. The valve includes an anterior (aortic) leaflet AL and a posterior (mural) leaflet PL. Chordae tendineae CT couple the valve leaflets AL, PL with the antero-lateral papillary muscle ALPM and the postero-medial papillary muscle PMPM. The valve leaflets AL, PL join one another along a line referred to as the antero-lateral commissure ALC and the posterior-medial commissure PMC. The annulus AN circumscribes the valve leaflets, and two regions adjacent an anterior portion of the annulus, on opposite sides of the anterior leaflet are referred to as the left fibrous trigone LFT and also the right fibrous trigone RFT. These areas are indicted by generally by the solid triangles. FIG. 5B more clearly illustrates the left and right fibrous trigones, LFT, RFT.

While various surgical techniques as well as implantable devices have been proposed and appear to be promising treatments for mitral regurgitation, surgical approaches can require a lengthy recovery period, and implantable devices have varying clinical results. Therefore, there still is a need for improved devices and methods for treating mitral regurgitation. While the embodiments disclosed herein are directed to an implantable prosthetic mitral valve for treating mitral regurgitation, one of skill in the art will appreciate that this is not intended to be limiting, and the device and methods disclosed herein may also be used to treat other cardiac valves such as the tricuspid valve, aortic valve, pulmonary valve, etc, as well as other valves in the body such as venous valves.

Prosthetic Valve. Prosthetic valves have been surgically implanted in the heart as a treatment for mitral regurgitation. Some of these valves have been valves harvested from animals such as porcine valves, and others have been prosthetic mechanical valves with or without a tissue covering. More recently, minimally invasive catheter technology has been used to deliver prosthetic valves to the heart. These valves typically include an anchor for securing the valve to the patient's heart, and a valve mechanism, either a mechanical valve, a valve with animal tissue, or combinations thereof. The prosthetic valve once implanted, takes over for malfunctioning native valve, thereby reducing or eliminating valvar insufficiency. While some of these valves appear promising, there still is a need for improved valves. The following discloses exemplary embodiments of a prosthetic valve, a delivery system for the prosthetic valve, and methods of delivering the valve that overcome some of the challenges associated with existing prosthetic valves.

Figure 6:
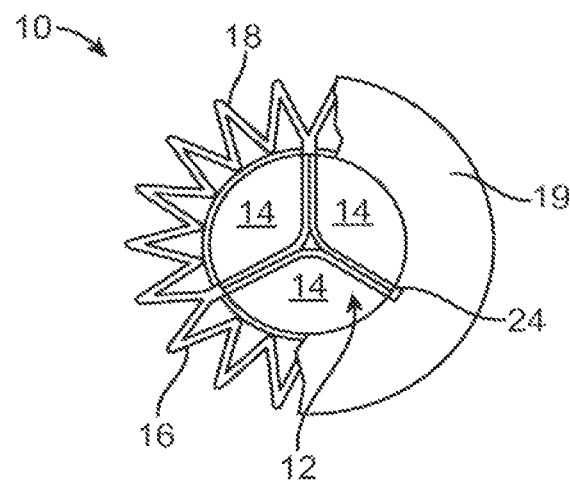
FIG. 6 illustrates a bottom, partial cross-sectional view of an exemplary prosthetic mitral valve.
Figure 7:
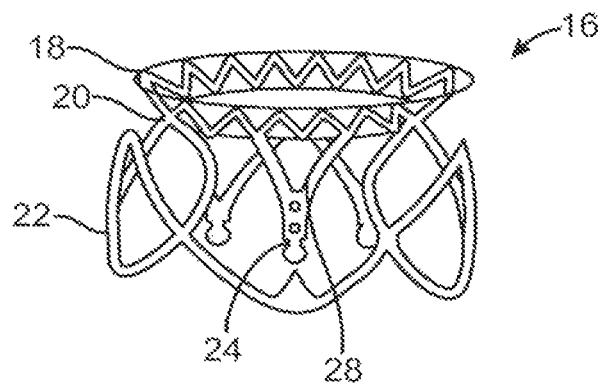
FIG. 7 is a perspective view of the anchor portion of the prosthetic mitral valve seen in FIG. 6.

Referring now to FIGS. 6-7, exemplary embodiments of a mitral valve prosthesis generally designated with reference numeral 10 comprise tricuspid tissue-type prosthetic one-way valve structure 12 comprising leaflets 14 affixed within self-expanding or expandable anchor portion 16 having a geometry that expands into low profile atrial skirt region 18, annular region 20, ventricular skirt region 22, and a plurality of leaflet commissures 24 (also referred to herein as commissure posts) extending axially in a cantilevered fashion downstream into the sub-annular space defined by ventricular skirt region 22. FIG. 6 shows a partial cross-section of the valve 10 from the patient's left ventricle looking upward toward the right atrium. The atrial skirt region 18 is anchored to a lower portion of the right atrium 19. The valve leaflets 14 have an open position (not illustrated) and a closed position illustrated in FIG. 6. In the open position, the leaflets 14 are displaced away from one another to allow blood flow therepast, and in the closed position, the leaflets 14 engage one another to close the valve and prevent retrograde blood flow therepast. The valve commissures 24 may be configured to optimize the efficiency of the prosthetic valve structure 12 and the load distribution on the leaflets 14 by providing for the attachment of the leaflets 14 along arcuate seams 28 (best seen in FIG. 7), and by being made selectively flexible at different points or zones along their axial length through the addition/deletion of reinforcing struts.

FIG. 7 shows a perspective view of the anchor portion 16 of the valve 10 which has been formed from a series of interconnected struts. The atrial skirt region 18 forms an annular flanged region on the anchor to help secure an upper portion of the prosthetic valve in the atrium, and the annular region 20 is a cylindrical region for anchoring the valve along the native valve annulus. The ventricular skirt region 22 similarly is cylindrically shaped and helps anchor a lower portion of the valve in the patient's left ventricle. Any portion, or all of the anchor may be covered with tissue such as pericardium or other tissues disclosed herein, or a synthetic material such as Dacron or ePTFE may be used to cover the anchor. The covering helps to seal the anchor to the native valve, and this helps funnel blood into and through the prosthetic valve, rather than around the valve. In some embodiments, the anchor may remain uncovered. The prosthetic valve has an expanded configuration and a collapsed configuration. The collapsed configuration has a low profile cylindrical shape that is suitable for mounting on a delivery system and delivery is preferably made either transluminally on a catheter, or transapically through the heart wall. The expanded configuration (as illustrated) allow the prosthetic valve to be anchored into a desired position.

Figure 8A:
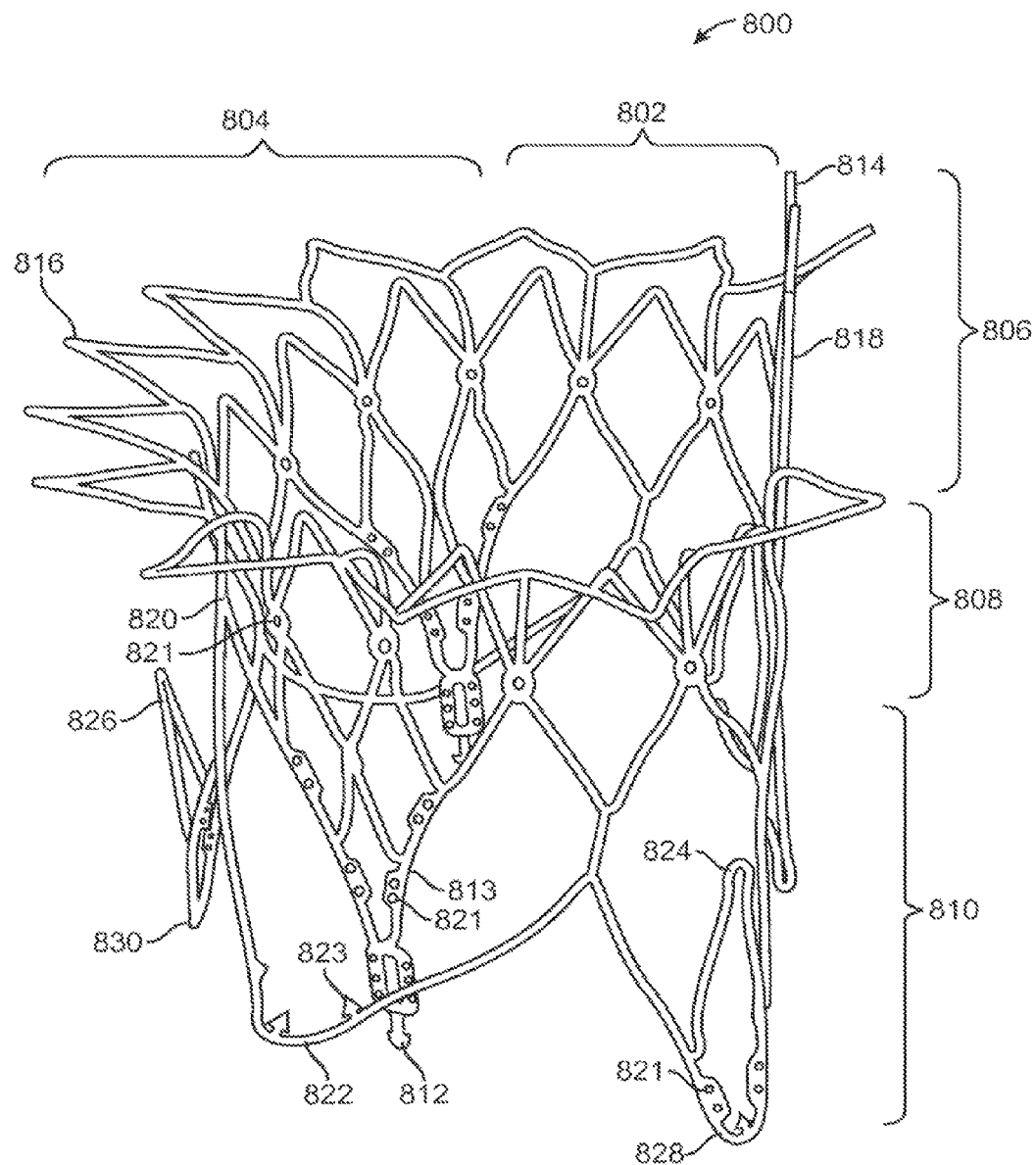
FIG. 8A is a perspective view of a prosthetic mitral valve.
Figure 8B:
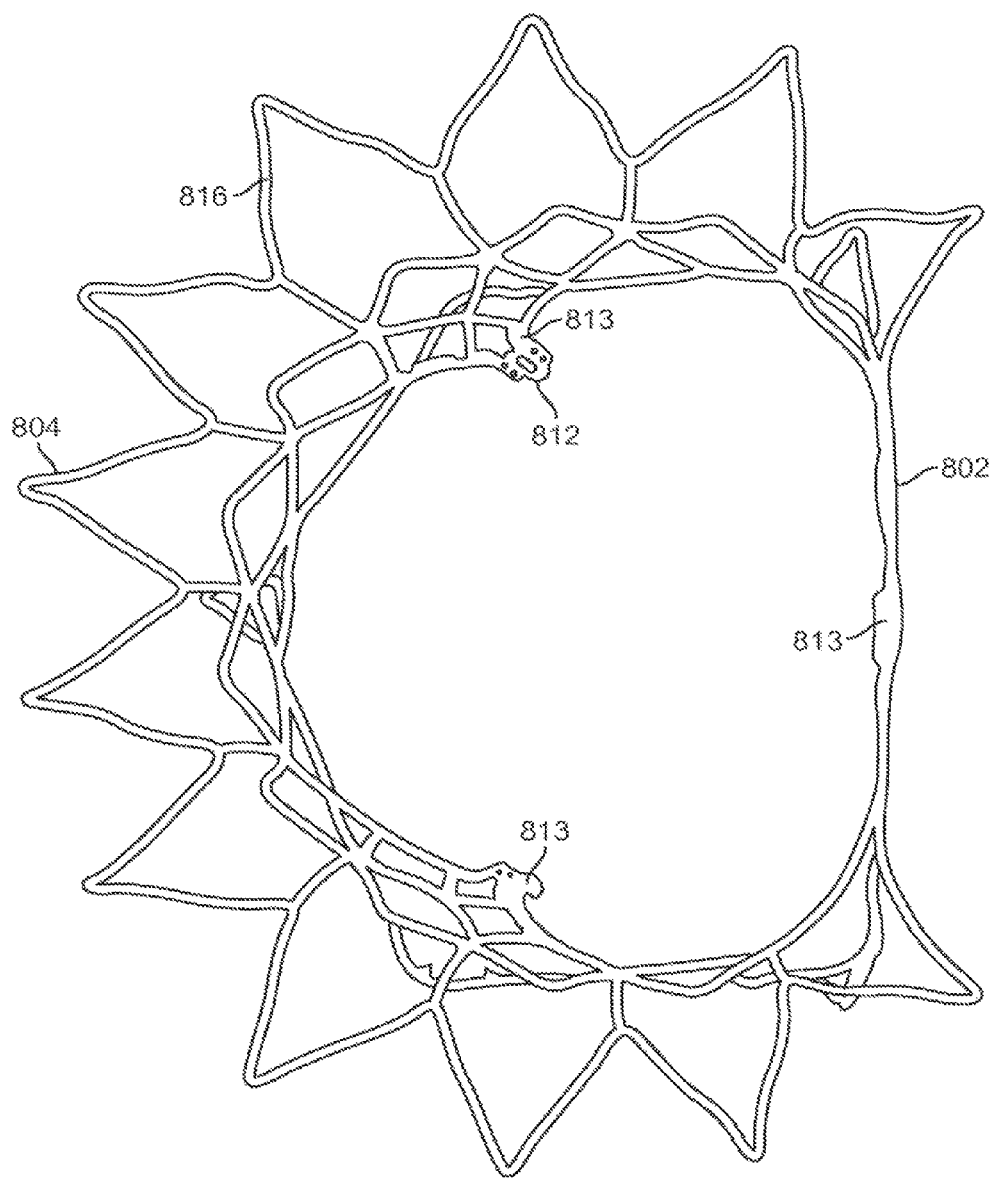
FIG. 8B is a top view from the atrium of the prosthetic valve in FIG. 8A.

FIG. 8A illustrates a perspective view of a preferred embodiment of a prosthetic mitral valve with optional coverings removed to allow visibility of the anchor struts. FIG. 8B illustrates a top view of the prosthetic valve in FIG. 8A from the atrium looking down into the ventricle. The valve 800 includes an asymmetrical expanded anchor portion having a D-shaped cross-section. As shown, the anchor portion generally comprises anterior 802 and posterior 804 aspects along the longitudinal axis thereof, as well as atrial 806, annular 808 and ventricular 810 regions that correspond generally to the atrial skirt 18, annular 20 and ventricular skirt 22 regions of the embodiment described above in FIGS. 6-7. Commissures (also referred to herein as commissure posts) 813 also correspond generally to the leaflets 14 of the embodiment in FIGS. 6-7. The prosthetic valve 800 has a collapsed configuration and an expanded configuration. The collapsed configuration is adapted to loading on a shaft such as a delivery catheter for transluminal delivery to the heart, or on a shaft for transapical delivery through the heart wall. The radially expanded configuration is adapted to anchor the valve to the patient's native heart adjacent the damaged valve. In order to allow the valve to expand from the collapsed configuration to the expanded configuration, the anchor portion of the valve may be fabricated from a self-expanding material such as a nickel titanium alloy like nitinol, or it may also be made from spring temper stainless steel, or a resilient polymer. In still other embodiments, the anchor may be expandable with an expandable member such as a balloon. In preferred embodiments, the anchor is fabricated by laser cutting, electrical discharge machining (EDM), or photochemically etching a tube. The anchor may also be fabricated by photochemically etching a flat sheet of material which is then rolled up with the opposing ends welded together.

The atrial skirt portion 816 forms a flanged region that helps to anchor the prosthetic valve to the atrium, above the mitral valve. The atrial skirt includes a plurality of triangular fingers which extend radially outward from the anchor to form the flange. The posterior 804 portion of the atrial skirt 816 is generally round or circular, while a portion of the anterior 802 part of the atrial skirt 816 is flat. Thus, the atrial skirt region preferably has a D-shaped cross-section. This allows the prosthetic valve to conform to the patient's cardiac anatomy without obstructing other portions of the heart, as will be discussed below. Each triangular finger is formed from a pair of interconnected struts. The triangular fingers of the atrial skirt generally are bent radially outward from the central axis of the prosthetic valve and lie in a plane that is transverse to the valve central axis. In some embodiments, the atrial skirt lies in a plane that is substantially perpendicular to the central axis of the valve. The anterior portion 802 of the atrial skirt 806 optionally includes an alignment element 814 which may be one or more struts which extend vertically upward and substantially parallel to the prosthetic valve. The alignment element 814 may include radiopaque markers (not illustrated) to facilitate visualization under fluoroscopy. The alignment element helps the physician to align the prosthetic valve with the native mitral valve anatomy, as will be discussed later.

Disposed under the atrial skirt region is the annular region 820 which also has a collapsed configuration for delivery, and an expanded configuration for anchoring the prosthetic valve along the native valve annulus. The annular region is also comprised of a plurality of interconnected struts that form a series of cells, preferably closed. Suture holes 821 in some of the struts allow tissue or other coverings (not illustrated) to be attached to the annular region. Covering all or a portion of the anchor with tissue or another covering helps seal the anchor against the heart valve and adjacent tissue, thereby ensuring that blood is funneled through the valve, and not around it. The annular region may be cylindrical, but in preferred embodiments has a posterior portion 804 which is circular, and an anterior portion 802 which is flat, thereby forming a D-shaped cross-section. This D-shaped cross-section conforms better to the native mitral valve anatomy without obstructing blood flow in other areas of the heart.

The lower portion of the prosthetic valve includes the ventricular skirt region 828. The ventricular skirt region also has a collapsed configuration for delivery, and an expanded configuration for anchoring. It is formed from a plurality of interconnected struts that form a series of cells, preferably closed, that can radially expand. The ventricular skirt in the expanded configuration anchors the prosthetic valve to the ventricle by expanding against the native mitral valve leaflets. Optional barbs 823 in the ventricular skirt may be used to further help anchor the prosthetic valve into the ventricular tissue. Barbs may optionally also be included in the atrial skirt portion as well as the annular region of the anchor. Additionally, optional suture holes 821 in the ventricular skirt may be used to help suture tissue or another material to the ventricular skirt region, similarly as discussed above. The anterior 802 portion of the ventricular skirt may be flat, and the posterior 804 portion of the ventricular skirt may be circular, similarly forming a D-shaped cross-section to anchor and conform to the native anatomy without obstructing other portions of the heart. Also, the lower portions of the ventricular skirt serve as deployment control regions since the lower portions can remain sheathed thereby constraining the ventricular skirt from radial expansion until after the optional ventricular trigonal tabs and posterior tab have expanded, as will be explained in greater detail below.

The ventricular skirt portion may optionally also include a pair of ventricular trigonal tabs 824 on the anterior portion of the anchor (only 1 visible in this view) for helping to anchor the prosthetic valve as will be discussed in greater detail below. The ventricular skirt may also optionally include a posterior tab 826 on a posterior portion 804 of the ventricular skirt for anchoring the prosthetic valve to a posterior portion of the annulus. The trigonal tabs 824 or the posterior tab 826 are tabs that extend radially outward from the anchor, and they are inclined upward in the upstream direction.

The actual valve mechanism is formed from three commissures posts (also referred to as commissures) 813 which extend radially inward toward the central axis of the anchor in a funnel or cone-like shape. The commissures 813 are formed from a plurality of interconnected struts that create the triangular shaped commissures. The struts of the commissures may include one or more suture holes 821 that allow tissue or a synthetic material to be attached to the commissures. In this exemplary embodiment, the valve is a tricuspid valve, therefore it includes three commissures 813. The tips of the commissures may include a commissure tab 812 (also referred to as a tab) for engaging a delivery catheter. In this embodiment, the tabs have enlarged head regions connected to a narrower neck, forming a mushroom-like shape. The commissures may be biased in any position, but preferably angle inward slightly toward the central axis of the prosthetic valve so that retrograde blood flow forces the commissures into apposition with one another to close the valve, and antegrade blood flow pushes the commissures radially outward, to fully open the valve. FIG. 8B is a top view illustrating the prosthetic valve of FIG. 8A from the atrial side, and shows the preferred D-shaped cross-section.

Figure 9A:
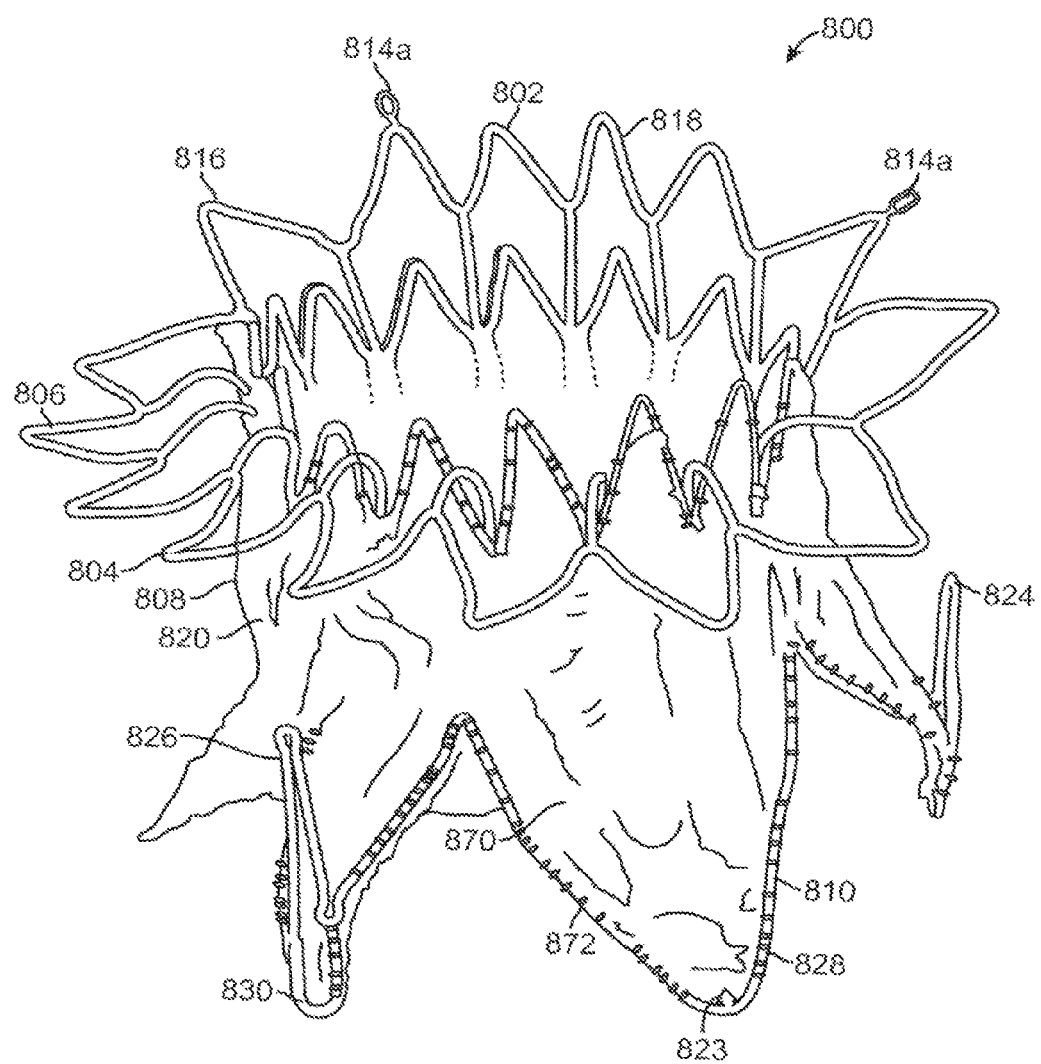
FIG. 9A is a perspective view of the prosthetic valve in FIG. 8A from the atrium.

FIG. 9A illustrates the prosthetic mitral valve of FIGS. 8A-8B with a covering 870 coupled to portions of the anchor with suture 872. This view is taken from an atrial perspective. In this embodiment, the covering is preferably pericardium which may come from a number of sources as disclosed elsewhere in this specification. In alternative embodiments, the covering may be a polymer such as Dacron polyester, ePTFE, or another synthetic material. The covering is preferably disposed over the annular region 820 and the ventricular skirt region 828, and in some embodiments the anterior ventricular trigonal 824 tabs and the ventricular posterior tab 830 may also be covered with the same or a different material. The covering helps seal the anchor against the adjacent tissue so that blood funnels through the valve mechanism. In this embodiment, the atrial skirt is left uncovered, as well as tabs 824, 830. Additionally, radiopaque markers 814a form a portion of the alignment element and facilitate visualization of the prosthetic valve under fluoroscopy which is important during alignment of the valve.

Figure 9B:
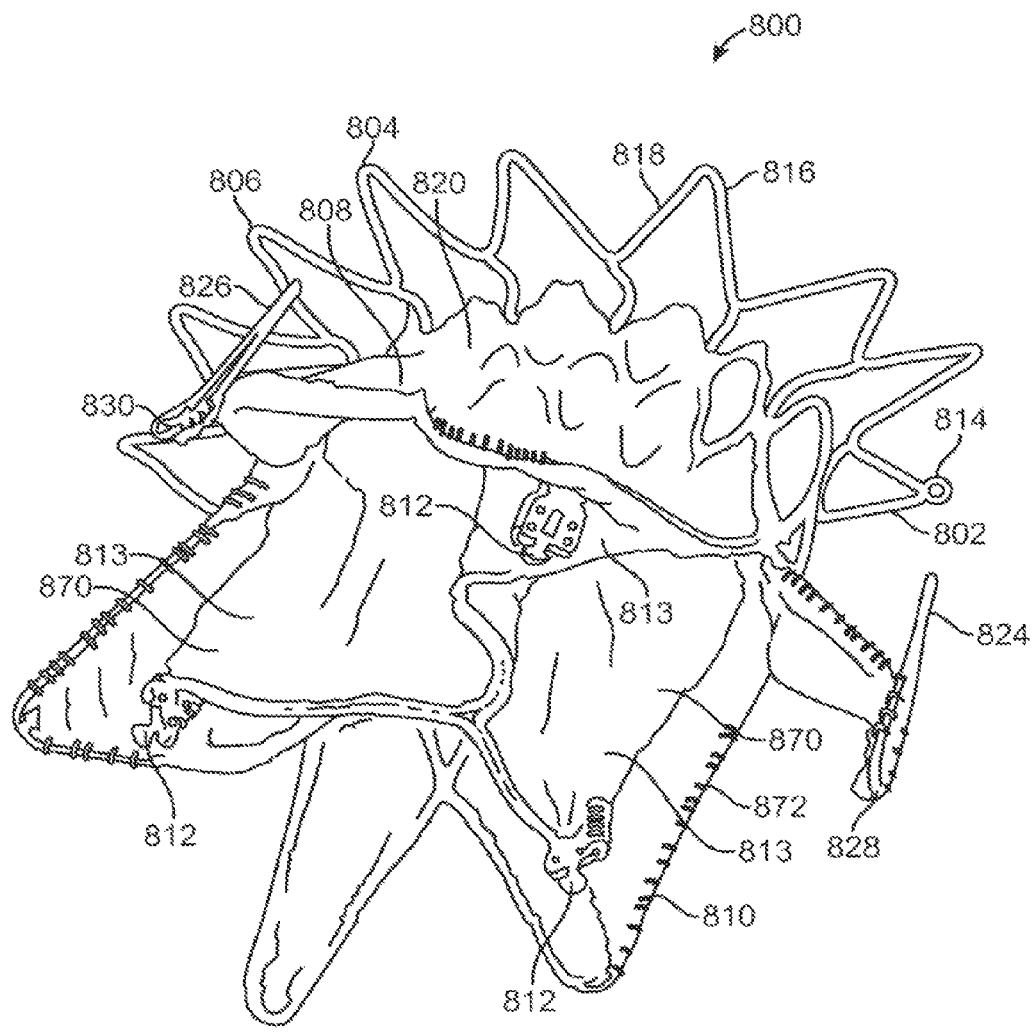
FIG. 9B illustrates a perspective view of the prosthetic valve in FIG. 8A from the ventricle.

FIG. 9B is a perspective view of the prosthetic mitral valve seen in FIG. 9A, as seen from the ventricle. The struts of the valve commissures are covered with the same material or a different material as the annular and ventricular regions as discussed above, thereby forming the tricuspid valve leaflets 813. FIG. 9B shows the valve in the closed configuration where the three leaflets are engaged with one another preventing retrograde blood flow. Commissure tabs 812 remain uncovered and allow the commissures to be coupled with a delivery device as will be explained below. The prosthetic valve in FIGS. 9A-9B may be sterilized so they are suitable for implantation in a patient using methods known in the art.

Figure 10:
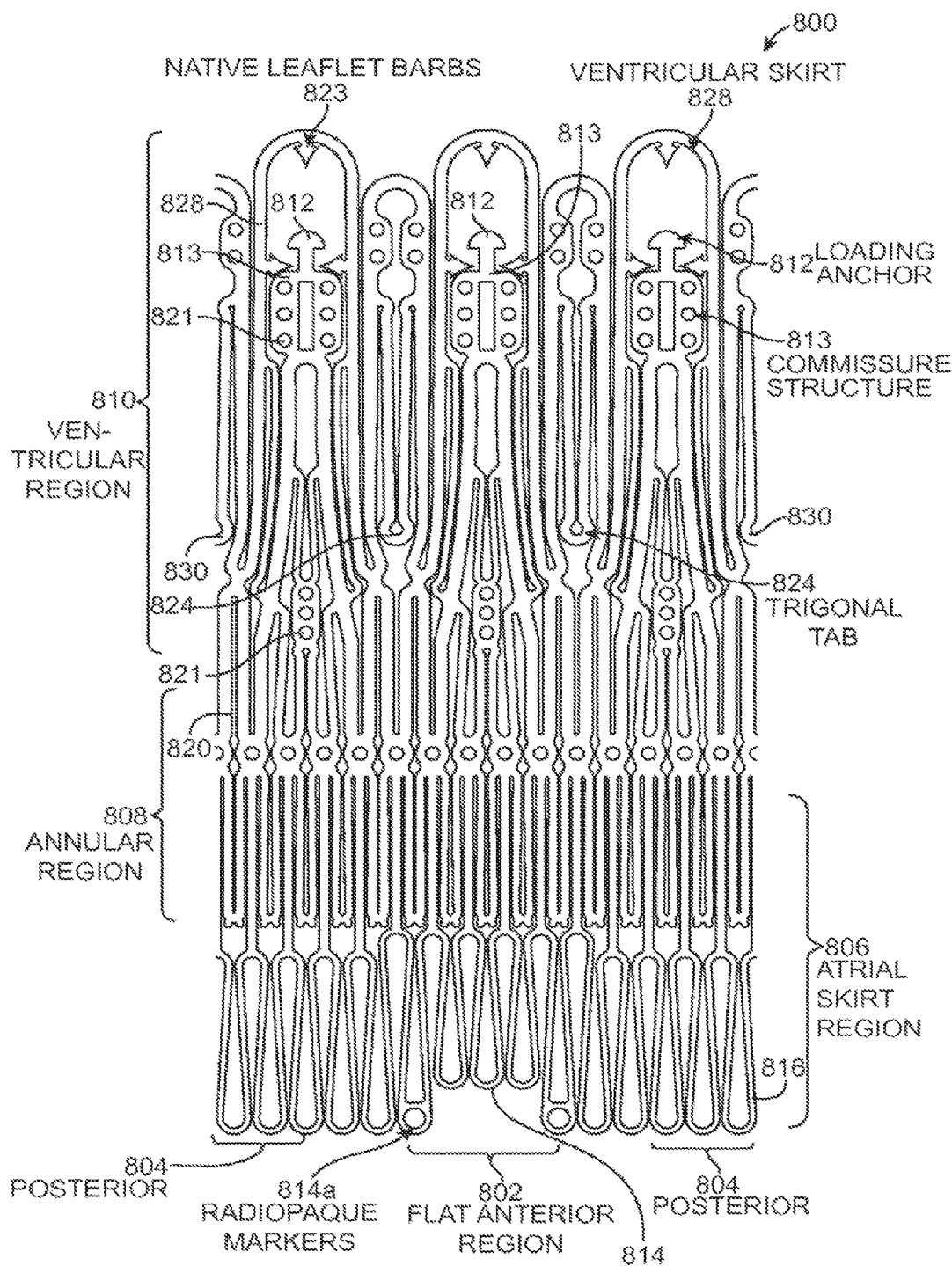
FIG. 10 illustrates the prosthetic valve of FIG. 8A uncovered and unrolled in a flat pattern.

FIG. 10 illustrates the prosthetic valve of FIG. 9A with the covering removed, and the remaining anchor unrolled and flattened out. The prosthetic valve 800 is formed from a plurality of interconnected struts. For example, the atrial skirt region 806 includes a plurality of interconnected struts that form a series of peaks and valleys. The flat anterior region 802 of the prosthetic valve has its peaks and valleys axially offset from those of the remaining portion of the atrial skirt, and this region becomes a part of the alignment element 814. Radiopaque markers 814a are disposed on either side of the offset peaks and valleys and help with visualization during implantation of the valve. An axially oriented connector joins the struts of the skirt region 806 with the struts of the annular region 808. The annular region is also comprised of a plurality of axially oriented and interconnected struts that form peaks and valleys. Connector struts couple struts of the annular region with the struts of the ventricular region 810. The ventricular region also includes a plurality of interconnected struts that form peaks and valleys. Additionally, the struts form the leaflet commissures 813, the ventricular skirt 828, as well as the trigonal and posterior tabs 824, 830. Suture holes 821 are disposed along the struts of the annular region as well as the ventricular region to allow attachment of a cover such as pericardium or a polymer such as Dacron or ePTFE. Barbs 823 are disposed along the ventricular skirt 828 to help anchor the prosthetic valve to adjacent tissue. Commissure tabs or tabs 812 are disposed on the tips of the commissures 813 and may be used to releasably couple the prosthetic valve with a delivery system as will be described below. One of skill in the art will appreciate that a number of strut geometries may be used, and additionally that strut dimensions such as length, width, thickness, etc. may be adjusted in order to provide the anchor with the desired mechanical properties such as stiffness, radial crush strength, commissure deflection, etc. Therefore, the illustrated geometry is not intended to be limiting.

Once the flat anchor pattern has been formed by EDM, laser cutting, photochemical etching, or other techniques known in the art, the anchor is radially expanded into a desired geometry. The anchor is then heat treated using known processes to set the shape. Thus, the anchor may be loaded onto a delivery catheter in a collapsed configuration and constrained in the collapsed configuration with a constraining sheath. Removal of the constraining sheath will allow the anchor to self-expand into its unbiased pre-set shape. In other embodiments, an expandable member such as a balloon may be used to radially expand the anchor into its preferred expanded configuration.

Delivery Systems. FIGS. 11-15C show a delivery apparatus 1124 fashioned to deliver a prosthetic mitral valve to the heart transapically. However, one of skill in the art will appreciate that the delivery system may be modified and relative motion of the various components adjusted to allow the device to be used to deliver a prosthetic mitral valve transseptally. The delivery apparatus is generally comprised of a handle 1101 that is the combination of a handle section 1102 and a handle section 1103 (best seen in FIG. 12), as well as a flexible tip 1110 that can smoothly penetrate the apex of the heart, and a sheath catheter 1109 which houses several additional catheters that are designed to translate axially and will be described in detail below.

The handle 1101 includes a female threaded luer adaptor 1113 which connects to a Tuohy Borst adaptor 1114 in order to provide a hemostatic seal with a 0.035" diameter guide wire (not shown). The female threaded luer adaptor 1113 is in threaded contact with the proximal section of the handle 1101 through a threaded port 1131 (best seen in FIG. 12).

Figure 11:
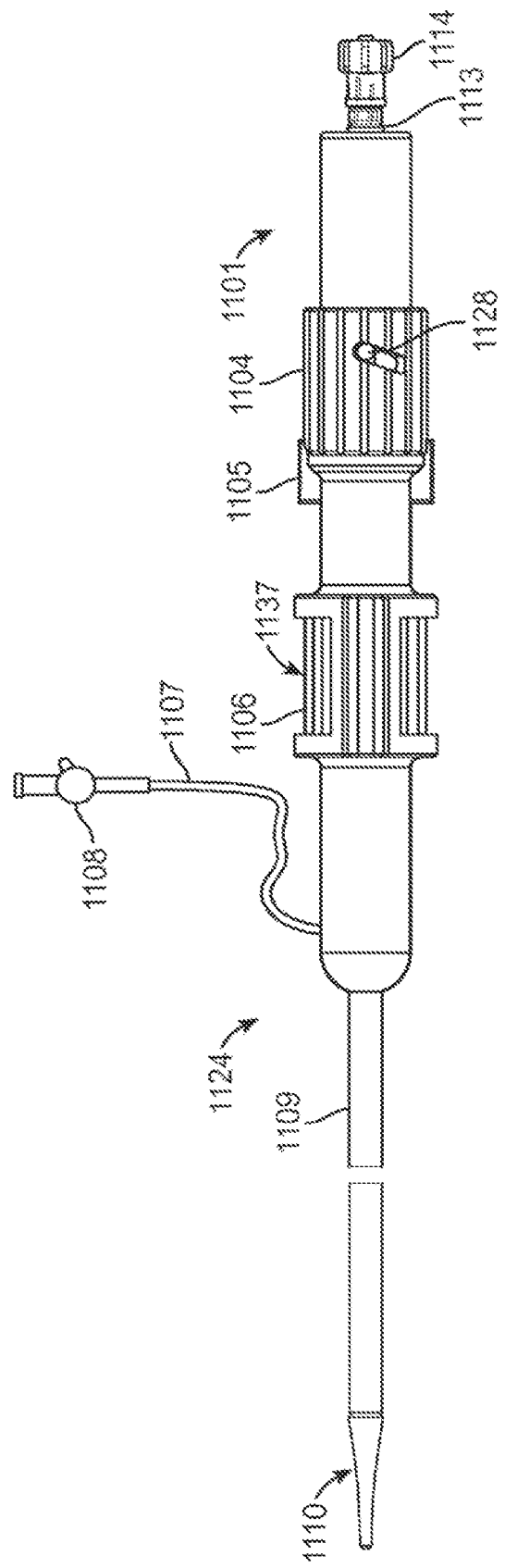
FIG. 11 is a side view of a delivery device for implantation of a prosthetic valve.

As can be seen in FIG. 11, the handle 1101 provides location for the control mechanisms used to position and deploy a prosthetic mitral valve. The handle 1101 provides housing for a thumbwheel 1106 that can be accessed through a window 1137 that appears on both the top and bottom of the handle 1101. The thumbwheel 1106 internally mates with a threaded insert 1115 (best seen in FIG. 12) that actuates the sheath catheter 1109, and the mechanics of this interaction will be explained in detail below.

FIG. 11 also shows a deployment thumbwheel 1104 that provides linear translation to a deployment catheter 1120 (best seen in FIG. 12) when turned, since the turning motion of the deployment thumbwheel 1104 acts as a power screw, pushing the peg 1128 forward and distally from the user. The mechanics behind the peg 1128 will be further detailed below. The thumbwheel lock 1105 provides a security measure against unwanted rotation of the deployment thumbwheel 1104 by acting as a physical barrier to rotation. In order to turn the deployment thumbwheel 1104 the user must push forward the thumbwheel lock 1105, disengaging it from two slots 1147 (seen in FIG. 12) in the deployment thumbwheel 1105.

As can also be seen in FIG. 11, a bleed valve 1108 and fluid line 1107 are connected to an internal mechanism in the distal portion of the handle 1101, which provides a hemostatic seal for the sheath catheter 1109. The details of this connection will be described below.

Figure 12:
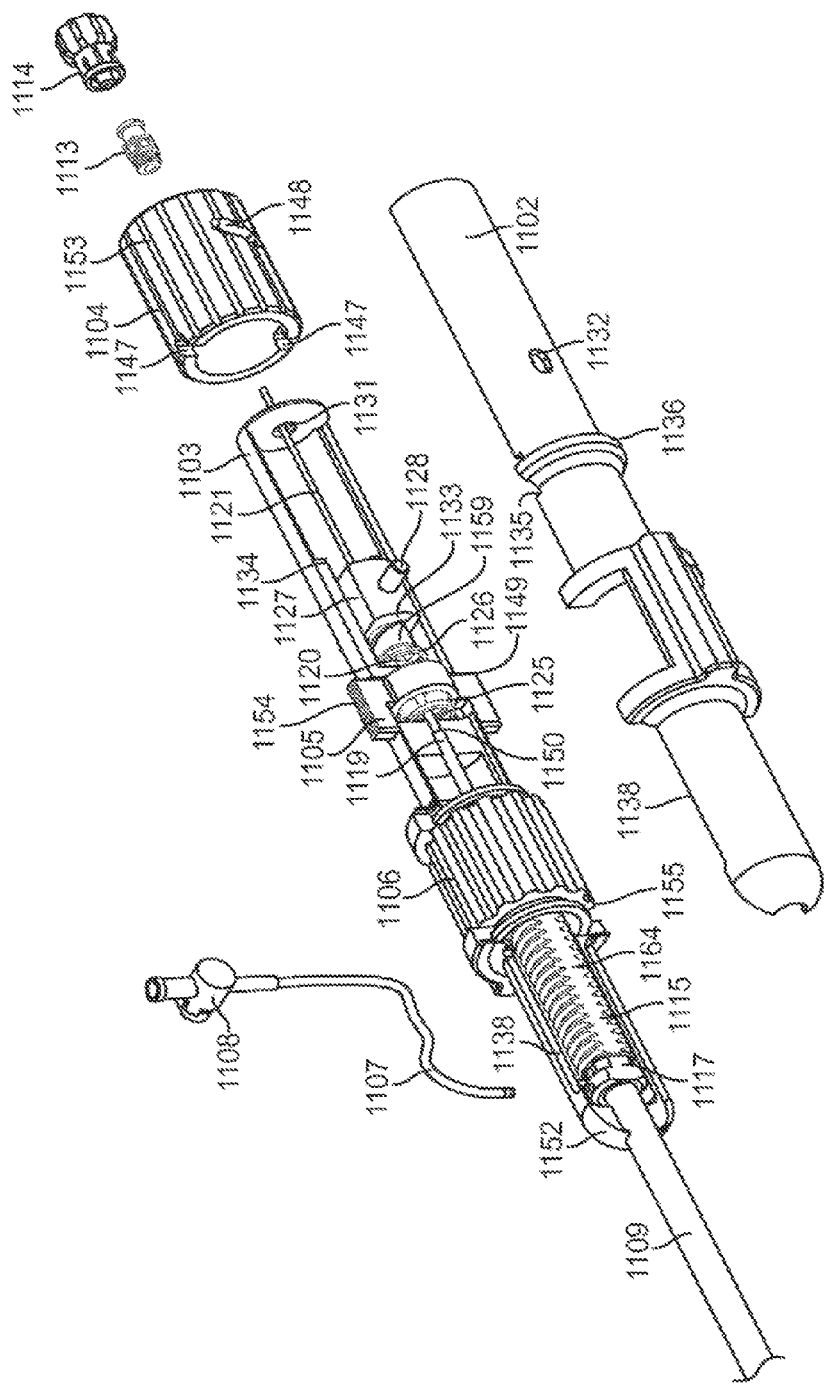
FIG. 12 is a perspective exploded view of a proximal portion of the delivery device in FIG. 11.

Internal mechanics of the delivery apparatus 1124 are illustrated in detail in FIG. 12, and the following descriptions will reveal the interactions between individual components, and the manner in which those components combine in order to achieve a prosthetic heart valve delivery apparatus.

As seen in FIG. 12, a handle section 1103 and handle section 1102 combine to create a handle 1101 that forms the basis of the delivery apparatus 1124. In order to advance the sheath catheter 1109 during valve loading, or retract the sheath catheter 1109 during deployment, a rotatable thumbwheel 1106 is in threaded contact (internal threads 1129 seen in FIG. 14) with a threaded insert 1115 (external threads 1130 of FIG. 13) that translates linearly along the axis of the delivery apparatus, from a proximal position to a distal position. The sheath catheter 1109 is in mating contact with the threaded insert 1115 and is fastened through the use of a collar 1117 that aligns and mates the collar with the insert. The collar 1117 is fastened with screws 1116 (best seen in DETAIL A in FIG. 14) to the threaded insert 1115 and contains a fluid port 1142 (best seen in DETAIL A in FIG. 14) that provides location for the fluid line 1117 so that hemostasis can be maintained between the patient and delivery apparatus. An O-ring 1118 (best seen in DETAIL A in FIG. 14) seals the stationary catheter 1119 (best seen in FIG. 14) against the sheath catheter 1109. The fluid line 1107 also provides a means of visually locating the sheath catheter 1109 with respect to position, as a slot 1138 in the handle 1101 allows the fluid line 1107 to translate with the sheath catheter 1109 (through a hole 1151 (best seen in DETAIL A in FIG. 14) during operation, and this translation is highly visible. In order to prevent rotation of the threaded insert during translation, a flat face 1164 has been machined onto both sides of the threaded insert 1115. The flat faces 1164 remain in contact with bosses 1139 and 1140 that are located on both handle section 1102 and handle section 1103 so that the bosses 1139 and 1140 act to grip the threaded insert 1115 and prevent rotation. A textured pattern 1155 allows the user to easily turn the thumbwheel 1106 in the surgical field. Detents 1141 (best seen in FIG. 14) locate flanges 63 (seen in FIG. 14) on the thumbwheel 1116 in order to allow for rotation.

The manner in which individual catheters (there are four catheters) move with respect to each other is illustrated in FIG. 12. Sheath catheter 1109 provides housing for the stationary catheter 1119, which in turn provides housing for the movable hub catheter 1120. The hub catheter 1120 translates linearly with respect to the nose catheter 1121 which can also be translated with respect to each previous catheter, and the handle 1101. The stationary catheter 1119 is mated to a handle section 1103 in an internal bore 1150 which also forms a seal between the stationary catheter 1119 and the hub catheter 1120. The distal portion of the stationary catheter 1119 is formed in the shape of a bell 1122 (see DETAIL A in FIG. 15A) which acts as a housing to retain the hub capture 1123 (seen in DETAIL A in FIG. 15A).

As previously stated a thumbwheel lock 1105 prevents rotation of the deployment thumbwheel 1104. In order to provide a seating force that keeps the thumbwheel lock 1105 in a locked position until manipulated, a spring 1125 is housed in an internal bore 62 (best seen in FIG. 14) and abuts against a shoulder 1161 (best seen in FIG. 14) that is located inside the thumbwheel lock 1105. This spring 1125 maintains the leading edge 1149 of the thumbwheel lock 1105 in a locked position within the two slots 1147 of the deployment thumbwheel 1104. Gripping texture 1154 is provided on the thumbwheel lock 1105 for ease of use. In order to locate and retain the thumbwheel lock 1105 inside of the handle 1101, a slot 1135 has been provided in both a handle section 1102 and a handle section 1103.

As shown in FIG. 12, a sliding block 1127 is housed inside of flat parallel faces 1134 which appear on the inside of the handle 1101. This sliding block 1127 is in mating contact with hub catheter 1120 and is the physical mechanism that linearly actuates the catheter. A spring 1126 is mounted on an external post 1159 and abuts against a shoulder 1133 that is located on the distal end of the sliding block 1127. This spring 1126 forces a peg 1128 (located inside a thru-hole 1156 of FIG. 14) into contact with the proximal edge of an angled slot 1148 that is cut into the deployment thumbwheel 1104. The deployment thumbwheel 1104 is contained between a shoulder 1136 and a snap ring (not shown), both of which are features of the handle 1101. Gripping texture 1153 on the deployment thumbwheel 1104 allows the user to easily rotate the thumbwheel in a clockwise direction, actuating the peg 1128 to ride distally along the slot 1148 and move the sliding block 1127, which pushes the hub catheter 1120 and hub 1123 (best seen in DETAIL A of FIG. 15A) forward and out of the bell 1122 (seen in DETAIL A of FIG. 15A). A slot 1132 appears in a handle section 1102 and a handle section 1103 and prevents the peg 1128 from translating beyond a desired range.

A nose catheter 1121 extends from a Tuohy Borst adaptor 1114 on the proximal end of the handle 1101, and internally throughout the handle and the respective catheters (sheath catheter 1109, stationary catheter 1119, and hub catheter 1120), terminating inside the rigid insert 1112 (seen in FIG. 15A) of the flexible tip 1110 (seen in FIG. 15A) that abuts with the distal end of the sheath catheter 1109.

Figure 13:
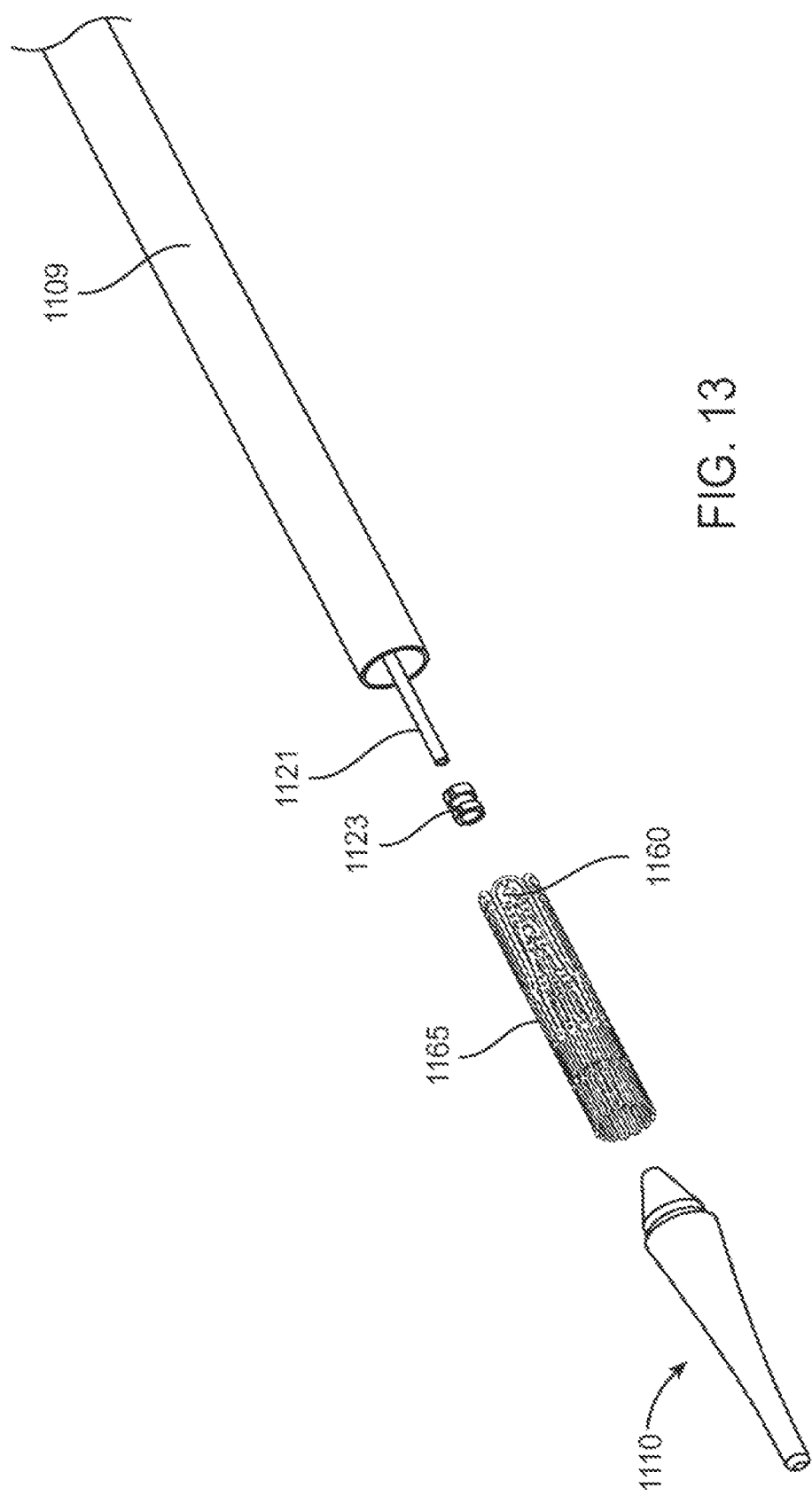
FIG. 13 is a perspective exploded view of a distal portion of the delivery device in FIG. 11.
Figure 14:
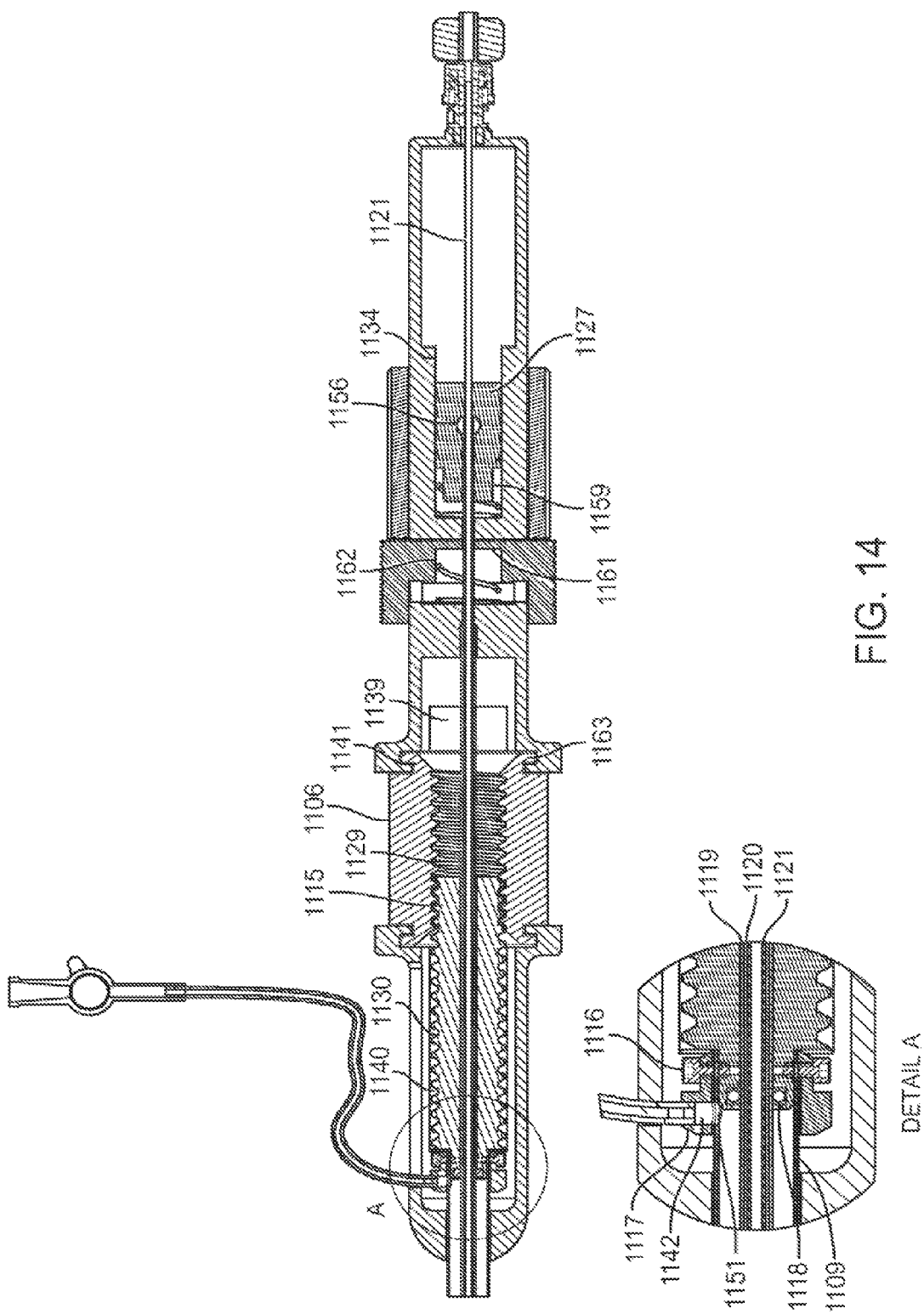
FIG. 14 is a cross-section of the a proximal portion of the delivery device in FIG. 11.

FIG. 13 displays an exploded view of the tip section of the delivery apparatus 1124, and shows the relation between prosthetic mitral valve 1165 and the internal and external catheters. When crimped and loaded, the prosthetic mitral valve 1165 is encased between the internal surface of the sheath catheter 1109 and the external surface of the nose catheter 1121. In order to capture and anchor the prosthetic mitral valve 1165 within the delivery apparatus 1124, three commissure tabs 1160 (circumferentially spaced at 120.degree. apart) appearing on the proximal end of the prosthetic mitral valve 1165 provide points of contact between the valve and three slots 1143 (seen in FIG. 15A) that are machined into the outer surface of the hub 1123 (circumferentially spaced at 120.degree. apart). After first advancing the hub catheter 1120 (FIG. 15A) by rotating the deployment thumbwheel 1104 (seen in FIG. 12) clockwise, the three commissure tabs 1160 can be captured within the three slots 1143 (seen in FIG. 15A). The hub 1123 can then be retracted into the bell 1122 by releasing the deployment thumbwheel 1104 (seen in FIG. 12). In this position the prosthetic mitral valve 1165 is anchored to the delivery apparatus 1124, and further crimping of the valve will allow the sheath catheter 1109 to be advanced over the valve.

Figure 15B:
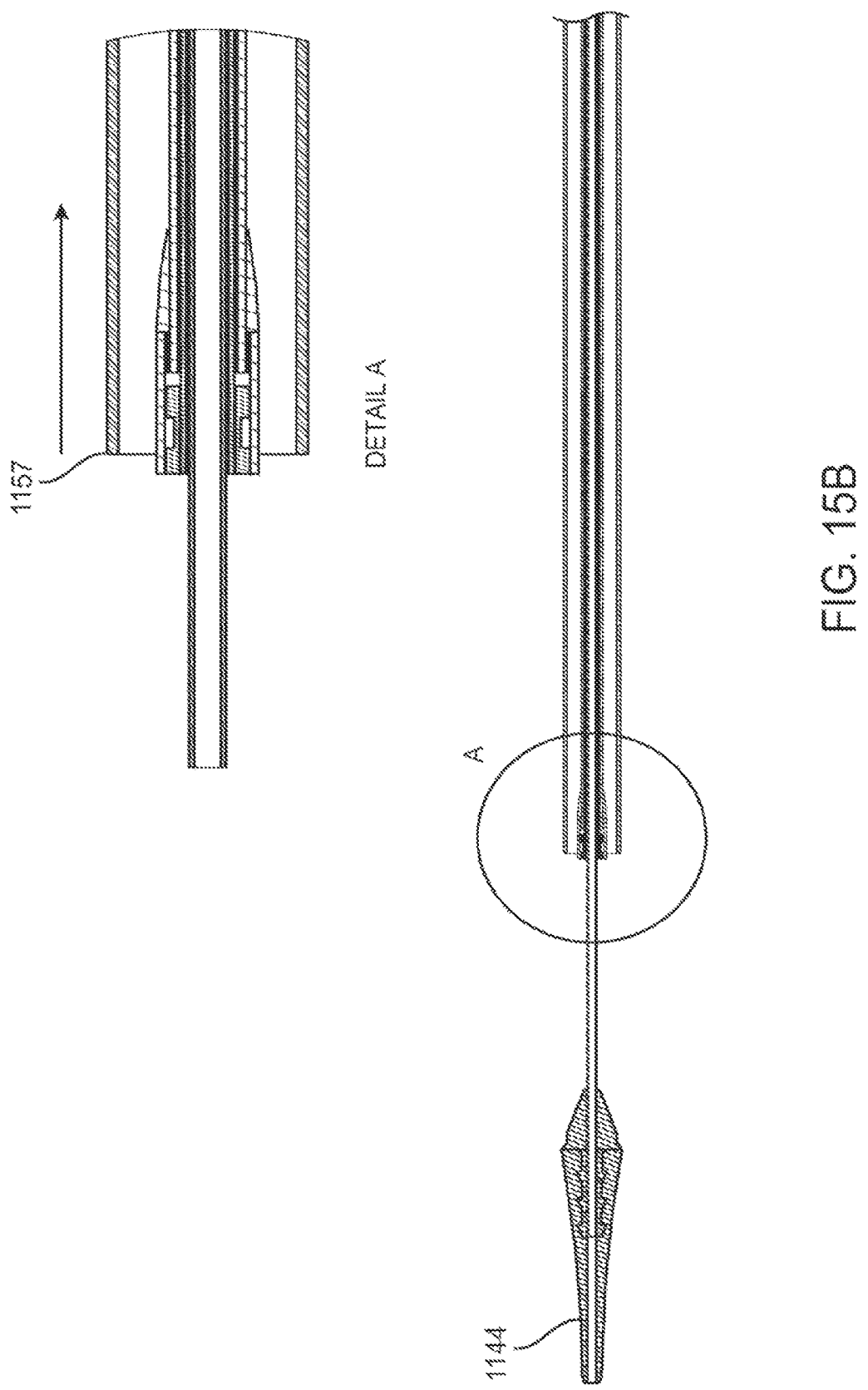

FIGS. 15A-15C further detail the manner in which loading of the prosthetic mitral valve 1165 (seen in FIG. 13) into the delivery apparatus 1124 can be achieved. Initially, the flexible tip 1110 is abutted against the distal edge 1157 of the sheath catheter 1109. The flexible tip 1110 is comprised of a rigid insert 1112, and a soft and flexible tip portion 1111 which is over-molded onto the rigid insert 1112. The shoulder 1145 and tapered face 1146 of the rigid insert 1112 act to guide and locate the distal edge 1157 of the sheath catheter 1109, so that the catheter may rest against and be stiffened by the flexible tip 1110, and be more easily introduced into the apex of the heart.

An initial position from which loading can be achieved is illustrated in FIG. 15A. As a first step in the loading of a prosthetic mitral valve 1165 (seen in FIG. 13) into the delivery apparatus 1124, the sheath catheter 1109 is withdrawn by rotation of the thumbwheel 1106 in a clockwise direction. The distal edge 1157 of the sheath catheter 1109 is retracted until it passes the distal edge of the bell 1122, as illustrated in DETAIL A of FIG. 15B. As a second step in the loading of a prosthetic mitral valve 1165 (seen in FIG. 13) into the delivery apparatus 1124, the hub 1123 is advanced from beneath the bell 1122 by clockwise turning of the deployment thumbwheel 1104 (seen in FIG. 12), as illustrated in DETAIL A of FIG. 15C. The deployment thumbwheel may only be turned once the thumbwheel lock 1105 (see FIG. 12) has been set in the forward position, disengaging it from contact with the thumbwheel. Advancement of the hub 1123 uncovers three slots 1143 into which three commissure tabs 1160 of the prosthetic mitral valve 1165 (seen in FIG. 13) will fit and be anchored. After anchoring of the commissure tabs 1160 into the slots 1143 by retraction of the hub 1123 has been achieved, a third step in the loading of a prosthetic mitral valve 1165 (seen in FIG. 13) into the delivery apparatus 1124 may be performed. The prosthetic mitral valve 1165 (seen in FIG. 13) can be crimped down to a minimum diameter by a loading mechanism (not shown), and then the sheath cannula 1109 can be advanced forward so as to cover the valve, by rotation of the thumbwheel 1106 in a counter-clockwise direction. The delivery apparatus 1124 and prosthetic mitral valve 1165 are then ready for deployment.

FIGS. 16-19B illustrate another exemplary embodiment of a delivery device for implanting a prosthetic valve in the heart transapically. However, one of skill in the art will appreciate that the delivery system may be modified and relative motion of the various components adjusted to allow the device to be used to deliver a prosthetic transseptally. The delivery apparatus is generally comprised of a handle 1601 that is the combination of two halves (1610 and 1635), as well as a tip 1603 that can smoothly penetrate the apex of the heart, and a flexible sheath 1602 which is comprised of concentric catheters that are designed to translate axially and will be described in detail below.

The handle 1601 includes a handle cap 1611 which connects to a female threaded luer adaptor 1612 in order to provide a sealable exit for a 0.035" diameter guide-wire (not shown). The handle cap 1611 is attached to the handle 1601 with threaded fasteners 1613. The female threaded luer adaptor 1612 is in threaded contact with the handle cap 1611 through a tapped port, and when fully inserted squeezes against an o-ring (1636 best seen in FIG. 18) which seals against the outer diameter of a guide-wire catheter (1621 best seen in FIG. 18).

Figure 17:
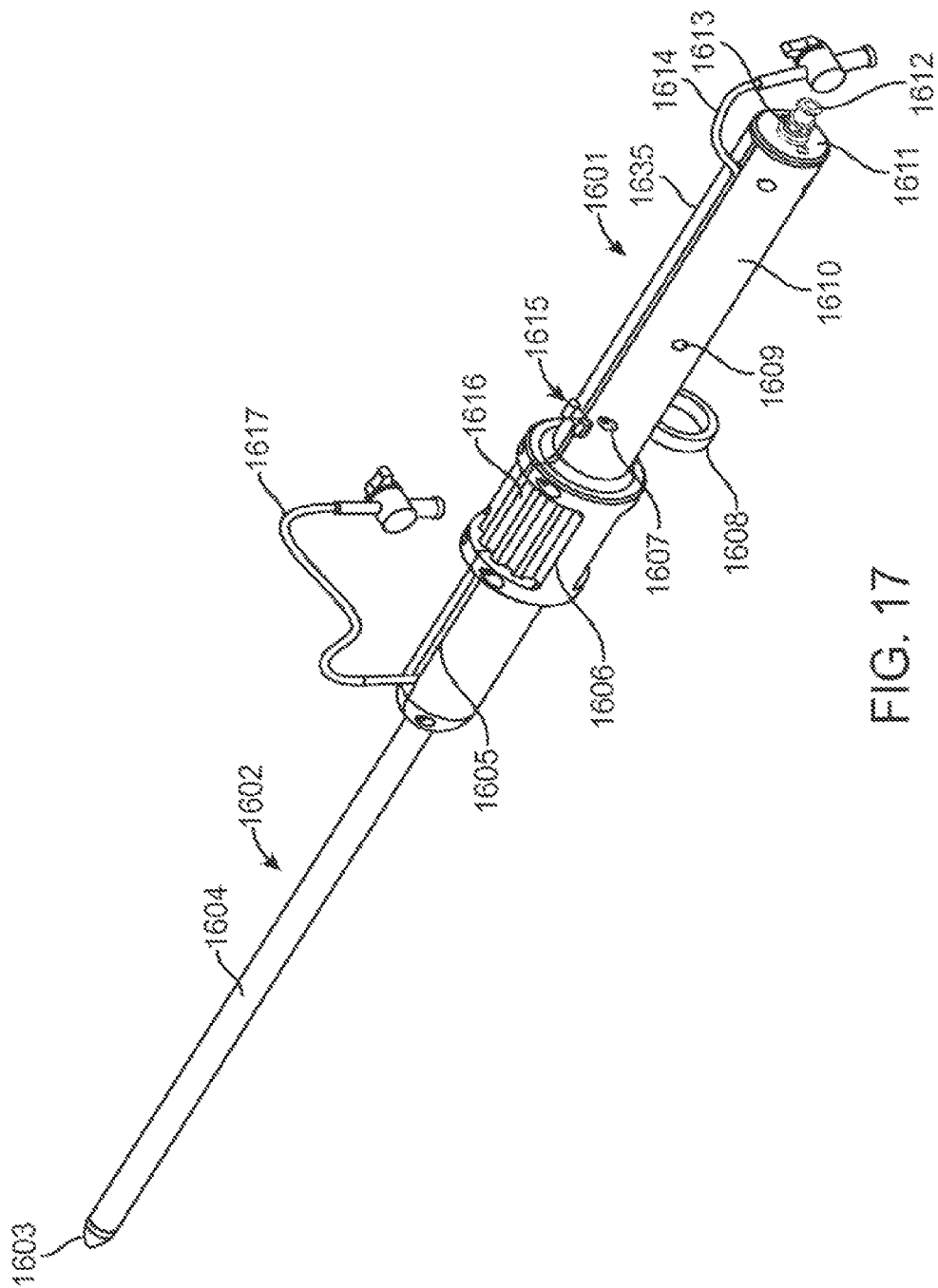
FIG. 17 is a perspective view of the delivery device in FIG. 16.

As can be seen in FIG. 17, the handle 1601 provides location for the control mechanisms used to position and deploy a prosthetic mitral valve. The handle 1601 provides housing for a thumbwheel 1616 that can be accessed through a window 1606 that appears on both the top and bottom of the handle 1601. The thumbwheel 1616 internally mates with a threaded insert (1627 in FIG. 18) that actuates the sheath catheter 1604, and the mechanics of this interaction will be explained in detail below.

Figure 18:
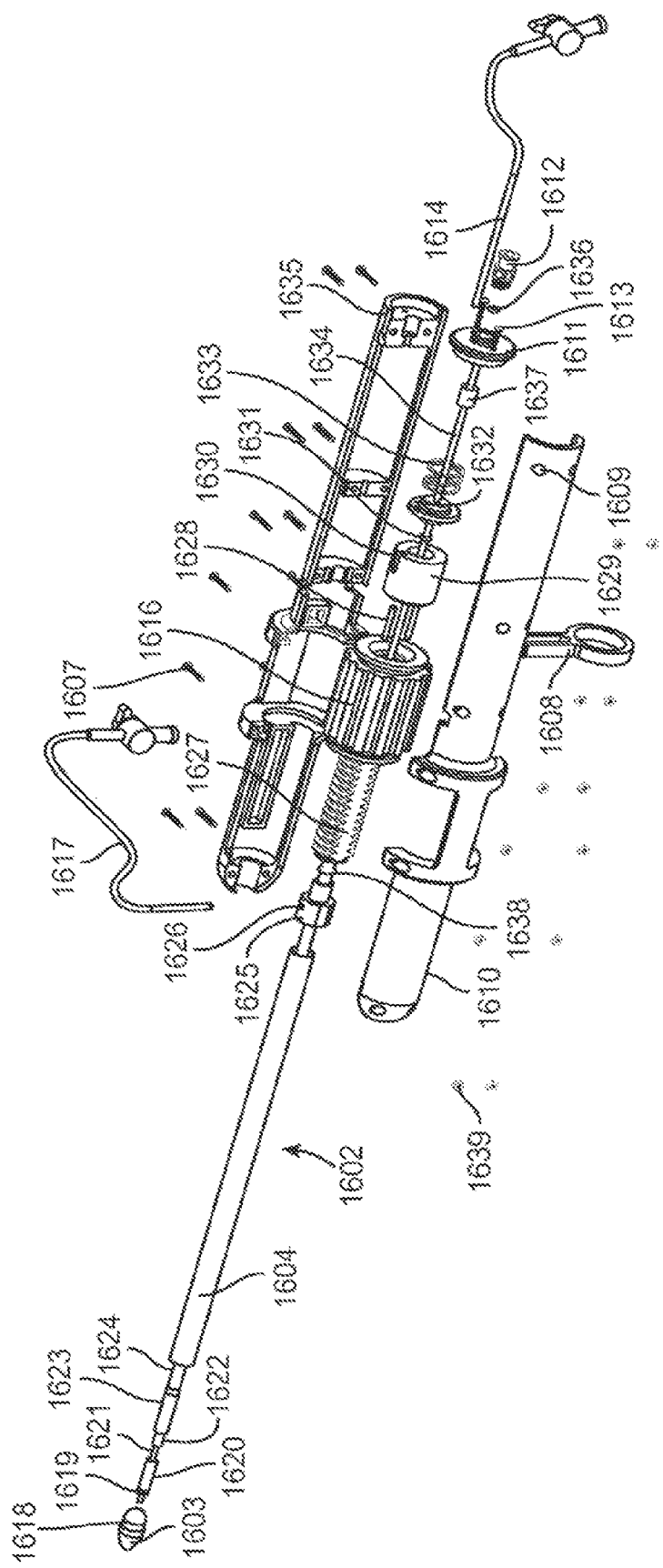
FIG. 18 is a perspective exploded view of the delivery device in FIG. 16.

FIG. 17 also shows a first hemostasis tube 1617 that is inserted internally through a slot 1605, and that mates with a first hemo-port through a hole (1625 and 1626 in FIG. 18 respectively). The first hemostasis tube 1617 allows for fluid purging between internal catheters. The position of the first hemostasis tube 1617 along the slot 1605 provides a visual cue as to the position of the sheath catheter 1604, and relative deployment phase of a prosthetic mitral valve (not shown). The relationship between the connection of the first hemostasis tube 1617 and the sheath catheter 1604 will be described below.

As can also be seen in FIG. 17, a second hemostasis tube 1614 is inserted into the handle 1601 and mated to a second hemo-port (1629 in FIG. 18) in order to allow fluid purging between internal catheters, and details of this insertion will be described below. Finally, a pin lock 1608 provides a security measure against premature release of a prosthetic mitral valve, by acting as a physical barrier to translation between internal mechanisms. Pin lock prongs 1615 rely on spring force to retain the pin lock 1608 in the handle 1601, and a user must first pull out the pin lock 1608 before final deployment of a prosthetic valve.

FIG. 17 also shows how the handle 1601 is fastened together by use of threaded fasteners and nuts (1607 and 1639 of FIG. 18 respectively), and countersunk locator holes 1609 placed throughout the handle length.

Internal mechanisms of the delivery system are illustrated in detail in FIG. 18, and the following descriptions will reveal the interactions between individual components, and the manner in which those components combine in order to create a system that is able to deliver a prosthetic mitral valve preferably transapically.

As seen in FIG. 18, the flexible sheath 1602 is comprised of four concentrically nested catheters. In order from smallest to largest in diameter, the concentrically nested catheters will be described in detail. The innermost catheter is a guide-wire catheter 1621 that runs internally throughout the entire delivery system, beginning at the tip 1603 and terminating in the female threaded luer adaptor 1612. The guide-wire catheter 1621 is composed of a lower durometer, single lumen Pebax extrusion and is stationary. It provides a channel through which a guide-wire (not shown) can communicate with the delivery system. The next catheter is the hub catheter 1622 which provides support for the hub 1620 and is generally comprised of a higher durometer, single lumen PEEK extrusion. The hub catheter 1622 is in mating connection with both the hub 1622 at the distal end, and a stainless steel support rod 1634 at the proximal end. The stainless steel support rod 1634 is held fixed by virtue of a stopper 1637 that is encased in the handle 1601. The hub catheter 1622 is stationary, and provides support and axial rigidity to the concentrically nested catheters. The next catheter is the bell catheter 1624, which provides housing to the hub 1620 and is generally comprised of a medium durometer, single lumen Pebax extrusion, including internal steel braiding and lubricious liner, as well as a radiopaque marker band (not shown). The bell catheter 1624 translates axially, and can be advanced and retracted with respect to the hub 1620. The bell catheter 1624 is in mating connection with the second hemo-port 1629 at the proximal end, and hemostasis between the bell catheter 1624 and the stainless steel support rod 1634 can be achieved by purging the second hemostasis tube 1614. The bell catheter 1624 is bumped up to a larger diameter 1623 on the distal end in order to encapsulate the hub 1620. The outermost and final catheter is the sheath catheter 1604 which provides housing for a prosthetic mitral valve (not shown), and which is able to penetrate the apex of the heart (not shown), by supporting and directing a tip 1603 and assisting in the dilation of an incision in the heart wall muscle. The sheath catheter 1604 is generally comprised of a medium durometer, single lumen Pebax extrusion, including internal steel braiding and lubricious liner, as well as radiopaque marker band (not shown). The sheath catheter 1604 translates axially, and can be advanced and retracted with respect to the hub 1620. The sheath catheter 1604 is in mating connection with the first hemo-port 1625 at the proximal end, and hemostasis between the sheath catheter 1604 and the bell catheter 1624 can be achieved by purging the first hemostasis tube 1617.

As seen in FIG. 18, the proximal end of the sheath catheter 1604 is in mating contact with a first hemo-port 1625. The first hemo-port is in mating contact with a threaded insert 1627, and an o-ring 1638, which is entrapped between the first hemo-port 1625 and the threaded insert 1627 in order to compress against the bell catheter 1624, creating a hemostatic seal. As the thumbwheel 1616 is rotated, the screw insert 1627 will translate, and the sheath catheter 1624 can be retracted or advanced by virtue of attachment. In order to provide adequate stiffness to dilate heart wall tissue, the distal edge of the sheath catheter 1604 will abut against a shoulder 1618 located on the tip 1603. This communication allows the tip 1603 to remain secure and aligned with the sheath catheter 1604 during delivery, and creates piercing stiffness.

FIG. 18 also details the mechanism through which the bell catheter 1624 can be retracted or advanced with respect to the hub 1620. The thumbwheel 1616 can be rotated to such an extent that the screw insert 1627 will be brought into contact with two pins 1628 that are press fit into the second hemo-port 1629. As the bell catheter 1624 is in mating contact with the second hemo-port 1629, further rotation of the thumbwheel 1616 will cause the second hemo-port 1629 to translate and press against a spring 1633 by virtue of connection to a second hemo-port cap 1632. This advancement will cause the bumped larger diameter section 1623 of the bell catheter 1624 to be retracted from the hub 1620. As the thumbwheel 1616 is rotated in the opposite direction, restoring force produced by the spring 1633 will cause the second hemo-port 1629 to be pushed in the opposite direction, drawing the bumped larger diameter section 1623 of the bell catheter 1624 back over the hub 1620, an action that is necessary during the initial loading of a valve prosthesis.

FIG. 18 further details the manner in which hemostasis is achieved between the stainless steel support rod 1634 and the bell catheter 1624. An o-ring 1631 is compressed between the second hemo-port 1629 and the second hemo-port cap 1632, creating a seal against the stainless steel support rod 1634. Hemostasis between the bell catheter 1624 and the stainless steel support rod 1634 can be achieved by purging the second hemostasis tube 1614, which is in communication with the void to be purged through a slot and hole 1630.

Figure 19A:
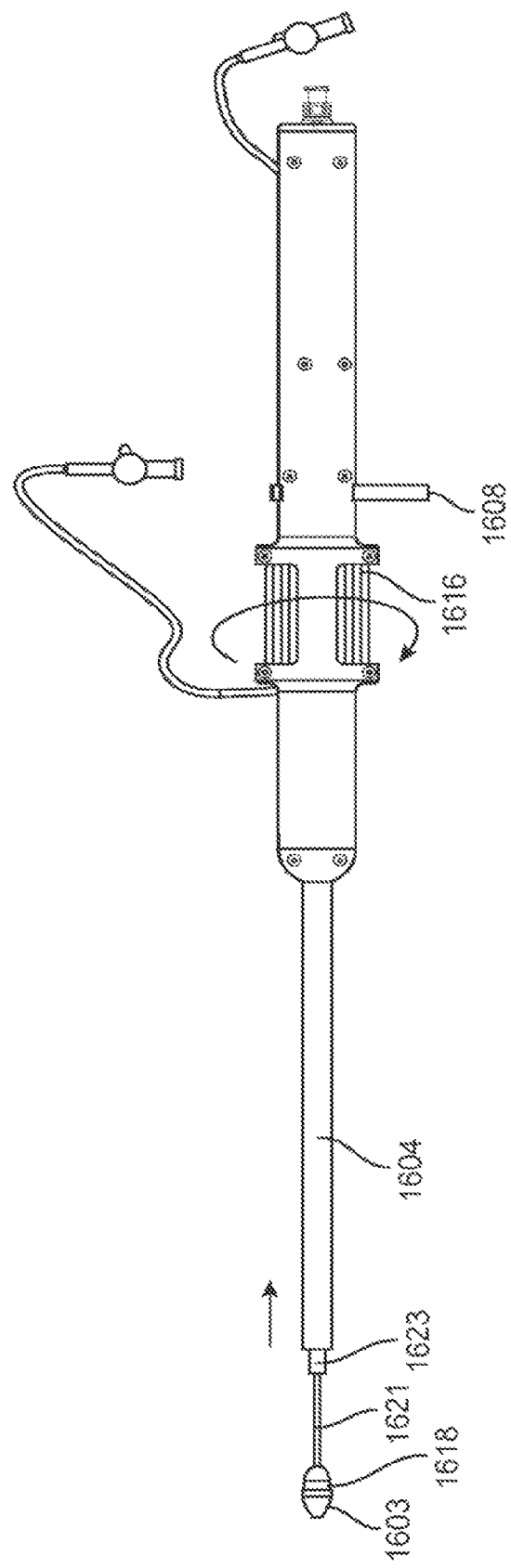

The deployment process and actions necessary to activate the mechanisms responsible for deployment are detailed in FIGS. 19A-19B. When performed in the reverse order, these actions also necessitate the first loading of a valve (not shown) prior to surgery.

As seen in FIG. 19A, manipulation of the thumbwheel 1616 will provide translational control of the sheath catheter 1604. In order to effect the deployment of a heart valve (not shown), the user must withdraw the sheath catheter 1604 from contact with the shoulder 1618 of the tip 1603 until it passes the larger diameter section 1623 of the bell catheter 1624. A heart valve (not shown) will reside concentrically above the guide-wire catheter 1621 in the position indicated by the leader for 1621 in FIG. 19A, similarly as to the embodiment illustrated in FIG. 13. The sheath catheter 1604 can be withdrawn until the screw insert 1627 comes into contact with the pin lock 1608. The pin lock 1608 must then be removed before further travel of the screw insert 1627 can be achieved.

As seen in FIG. 19B, the pin lock 1608 is removed from the handle 1601 in order to allow further translation of the sheath catheter 1604. When the sheath catheter 1604 is fully retracted, the larger diameter section 1623 of the bell catheter 1624 is also fully retracted, which completely frees the heart valve (not shown) from the delivery system. Three hub slots 1619, spaced circumferentially at 120.degree. from each other provide the anchoring mechanism and physical link between delivery system and heart valve. Once the larger diameter section 1623 of the bell catheter 1624 has been withdrawn, the hub slots 1619 become uncovered which allows the heart valve anchor (not shown) to fully expand.

Figure 16:
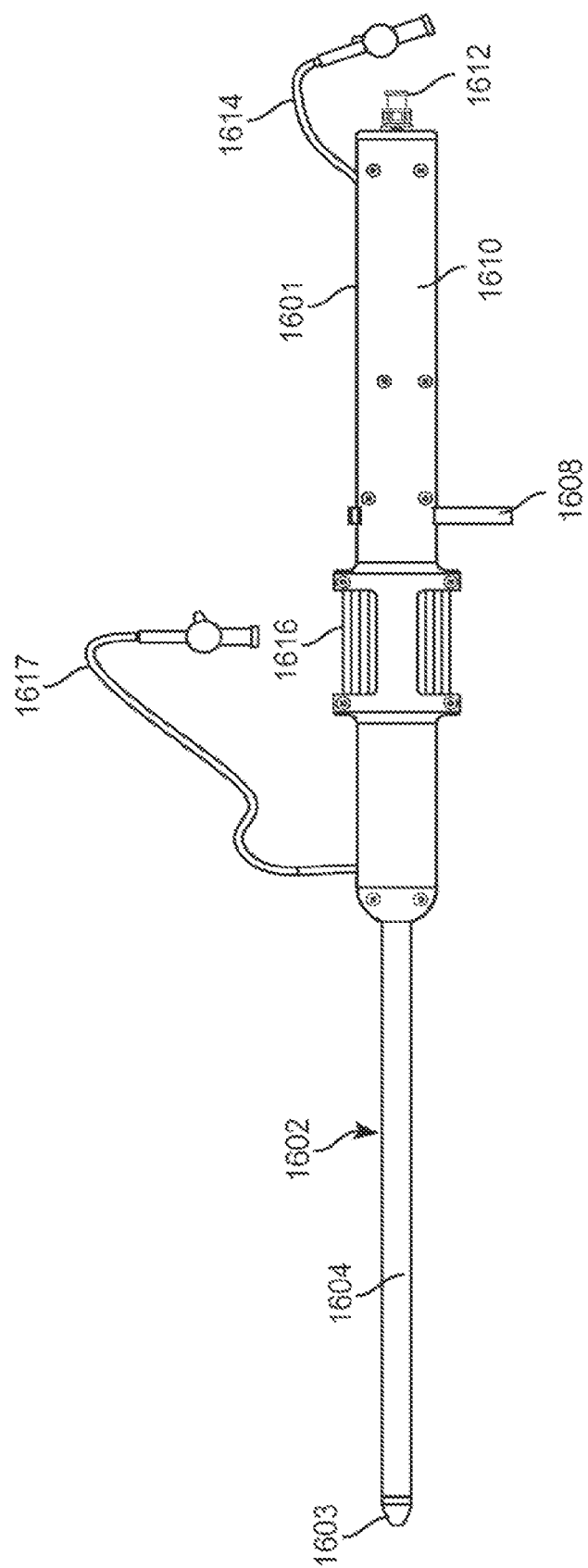
FIG. 16 is a side view of another exemplary embodiment of a delivery device for implantation of a prosthetic valve.
Figure 20:
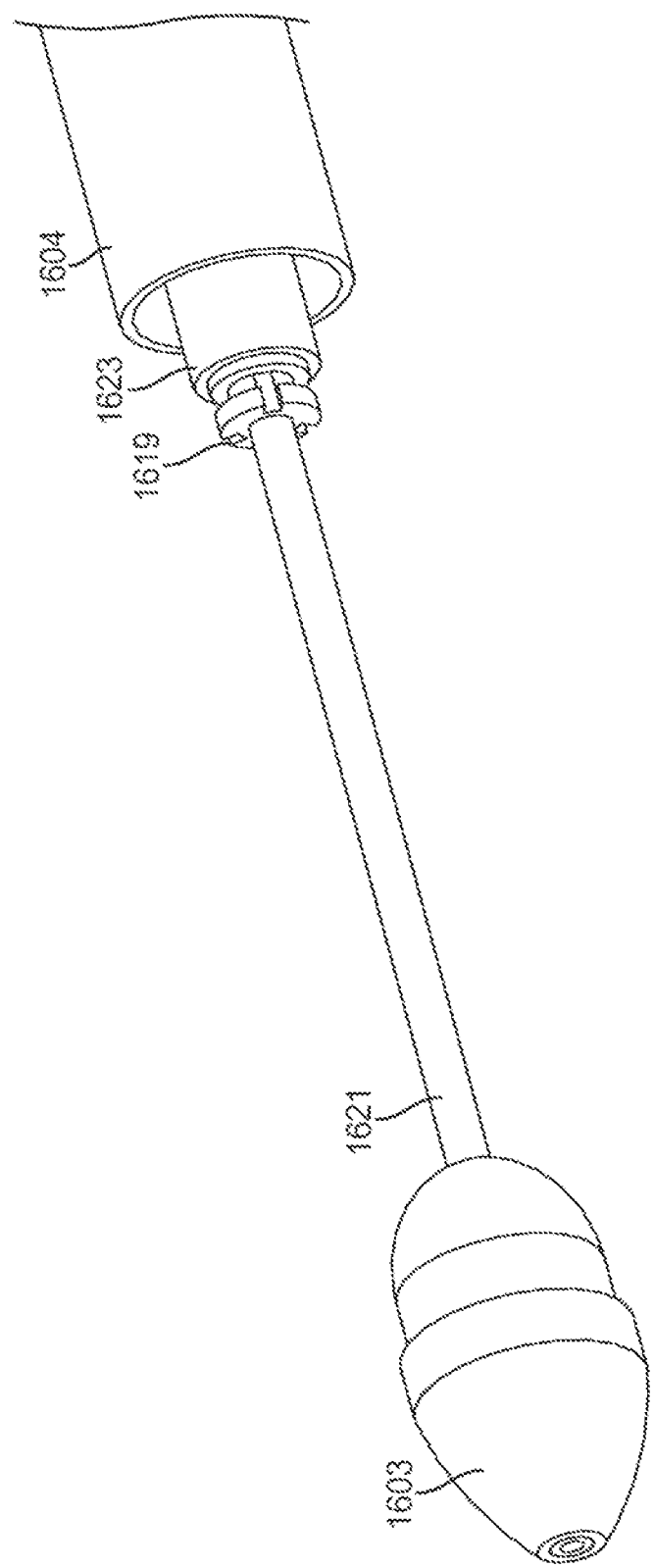
FIG. 20 illustrates a distal portion of the delivery device in FIG. 16 that is adapted to engage a portion of a prosthetic valve.

FIG. 20 illustrates a distal portion of the delivery device in FIG. 16. Three hub slots 1619 are slidably disposed distally relative to the large diameter tip 1623 of bell catheter 1624. These slots allow engagement with a prosthetic valve. The valve may be releasably held by the slots by disposing the commissure tabs or tabs 812 of the prosthetic valve into slots 1619 and then retracting the slots 1619 under tip 1623 of bell catheter 1624. The prosthetic valve may be released from the delivery catheter by advancing the slots distally relative to the bell catheter so that the loading anchors or tabs 812 may self-expand out of and away from slots 1619 when the constraint of tip 1623 on bell catheter 1624 has been removed.

FIG. 21 illustrates a prosthetic mitral valve 800 (as discussed above with reference to FIG. 8A) with the anchor tabs 812 disposed in the hub slots (not visible), and bell catheter 1623 advanced thereover. Thus, even though most of the prosthetic valve 800 has self-expanded into its expanded configuration, the valve commissures remain in a collapsed configuration with the tabs 812 captured in slots 1619. Once the constraint provided by bell catheter 1623 has been removed from the slots 1619, the tabs 812 may self-expand out of slots 1619, the commissures will open up to their unbiased position. The prosthetic valve is then disconnected and free from the delivery device.

Figure 22A:
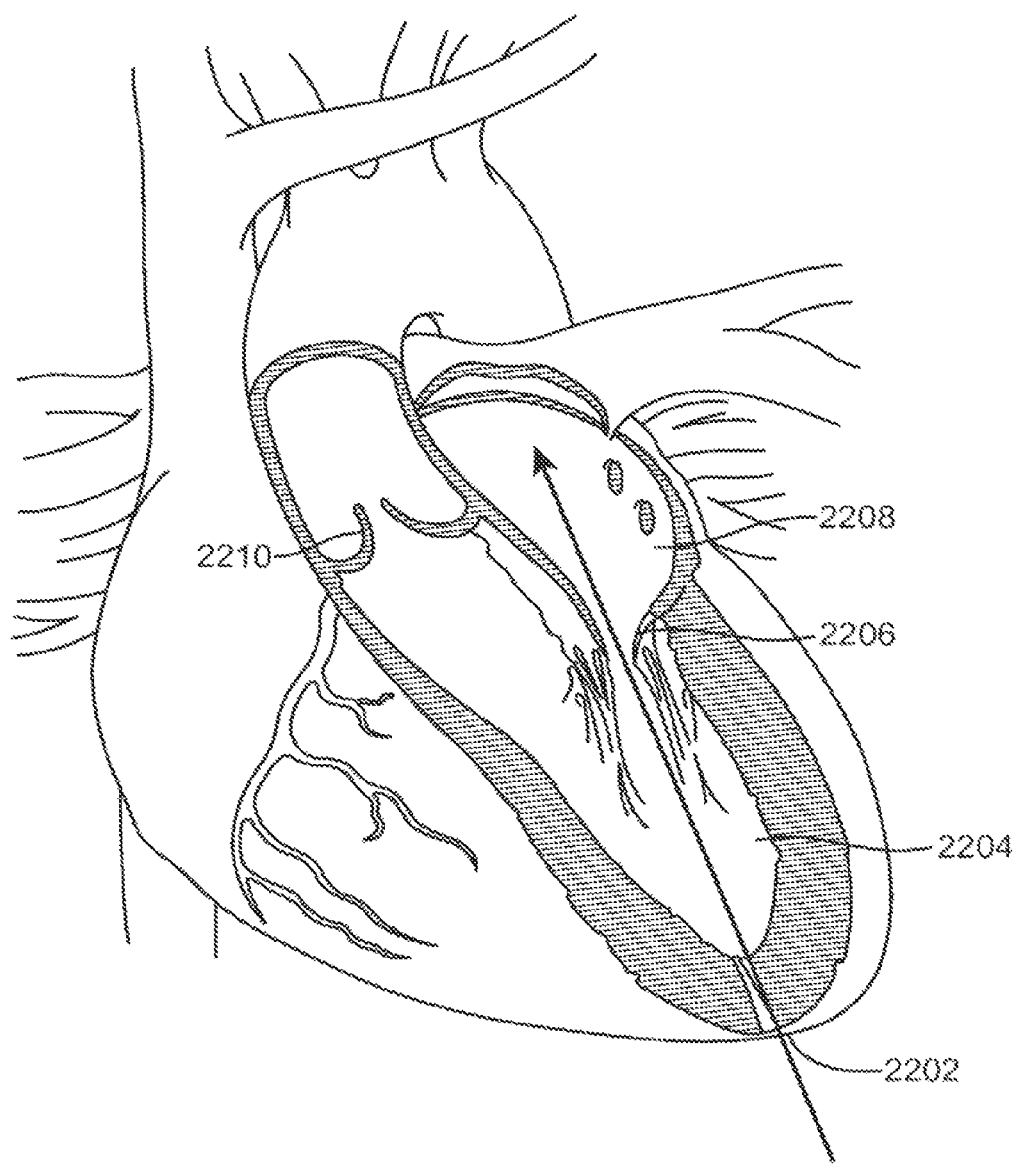
FIGS. 22A-22G illustrate an exemplary method of transapically delivering a prosthetic mitral valve.

Transapical Delivery Methods. FIGS. 22A-22G illustrate an exemplary method of transapically delivering a prosthetic mitral valve. This embodiment may use any of the prosthetic valves described herein, and may use any of the delivery devices described herein. FIG. 22A illustrates the general transapical pathway that is taken with entry into the heart at the apex 2202, through the left ventricle 2204, across the mitral valve 2206 and into the left atrium 2208. The aortic valve 2210 remains unaffected. Transapical delivery methods have been described in the patent and scientific literature, such as in International PCT Publication No. WO2009/134701, the entire contents of which are incorporated herein by reference.

Figure 22B:
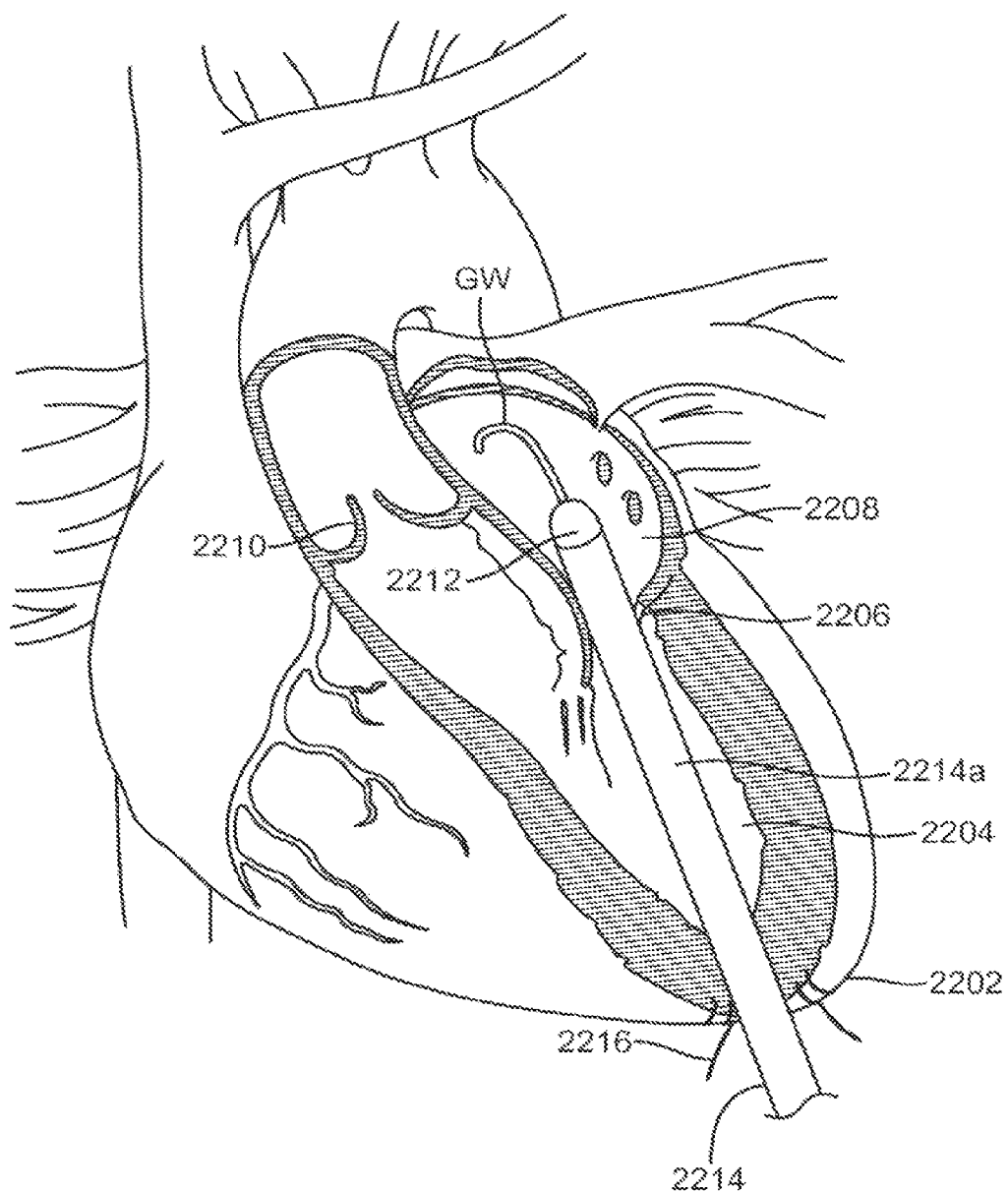

In FIG. 22B a delivery device 2214 is introduced through an incision in the apex 2202 and over a guidewire GW through the ventricle 2204, past the mitral valve 2206 with a distal portion of the delivery device 2214 disposed in the atrium 2208. The delivery device has a rounded tip 2212 that is configured to pass through and dilate the incision, and can be advanced through the heart without causing unwanted trauma to the mitral valve 2206 or adjacent tissue. Suture 2216 may be stitched around the delivery device 2214 at the apex 2202 using a purse string stitch or other patterns known in the art in order to prevent excessive bleeding and to help hold the delivery device in position.

Figure 22C:
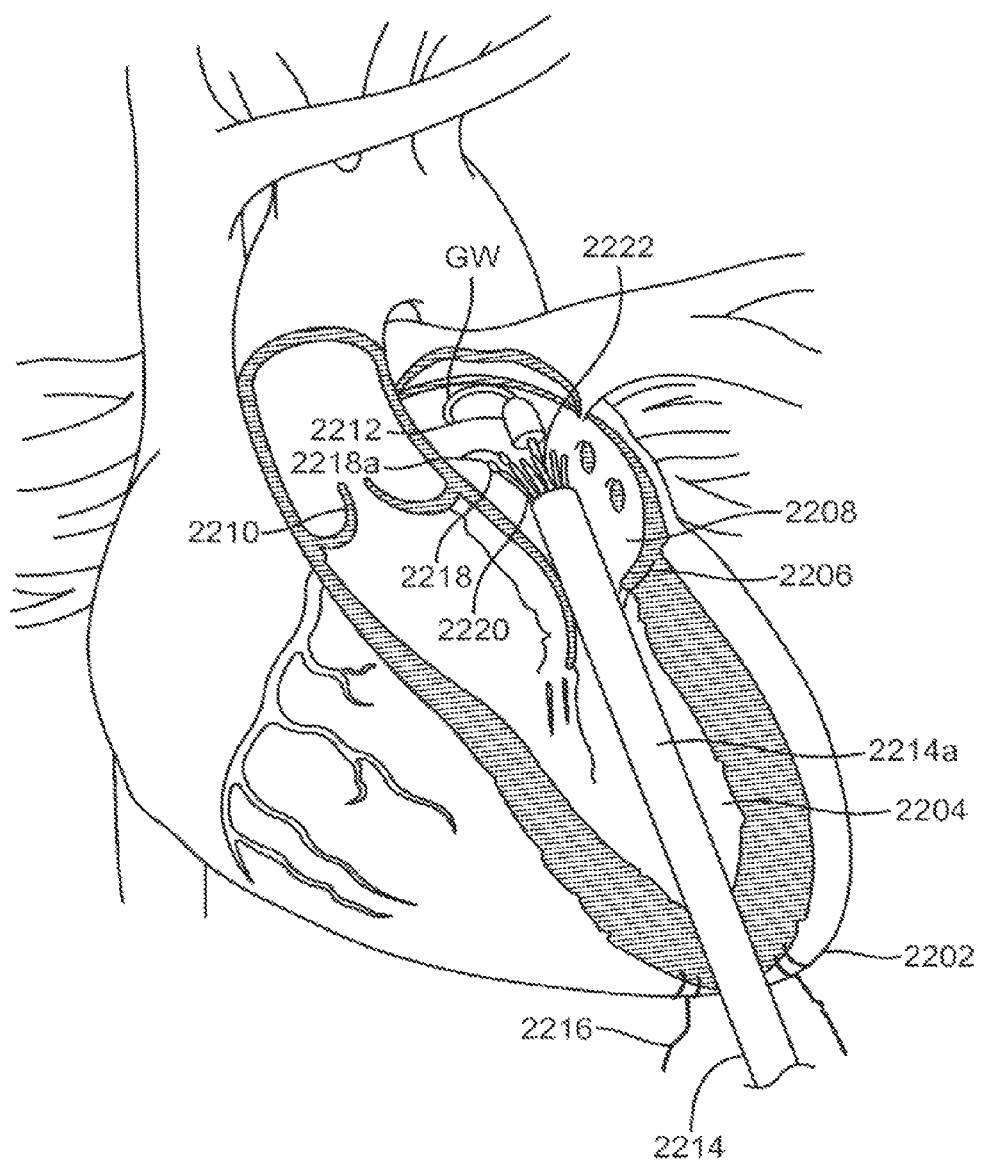

In FIG. 22C, the outer sheath 2214a of the delivery device 2214 is retracted proximally relative to the prosthetic mitral valve 2220 (or the prosthetic mitral valve is advanced distally relative to the outer sheath 2214a) to expose the alignment element 2218 and a portion of the atrial skirt region 2222 on the prosthetic mitral valve 2220 which allows the atrial skirt region 2222 to begin to partially radially expand outward and flare open. Alignment element 2218 may include a pair of radiopaque markers 2218a which facilitate visualization under fluoroscopy. The physician can then align the alignment element so that the radiopaque markers 2218a are disposed on either side of the anterior mitral valve leaflet. Delivery device 2214 may be rotated in order to help align the alignment element. The alignment element is preferably situated adjacent the aortic root and between the fibrous trigones of the native anterior leaflet.

Figure 22D:
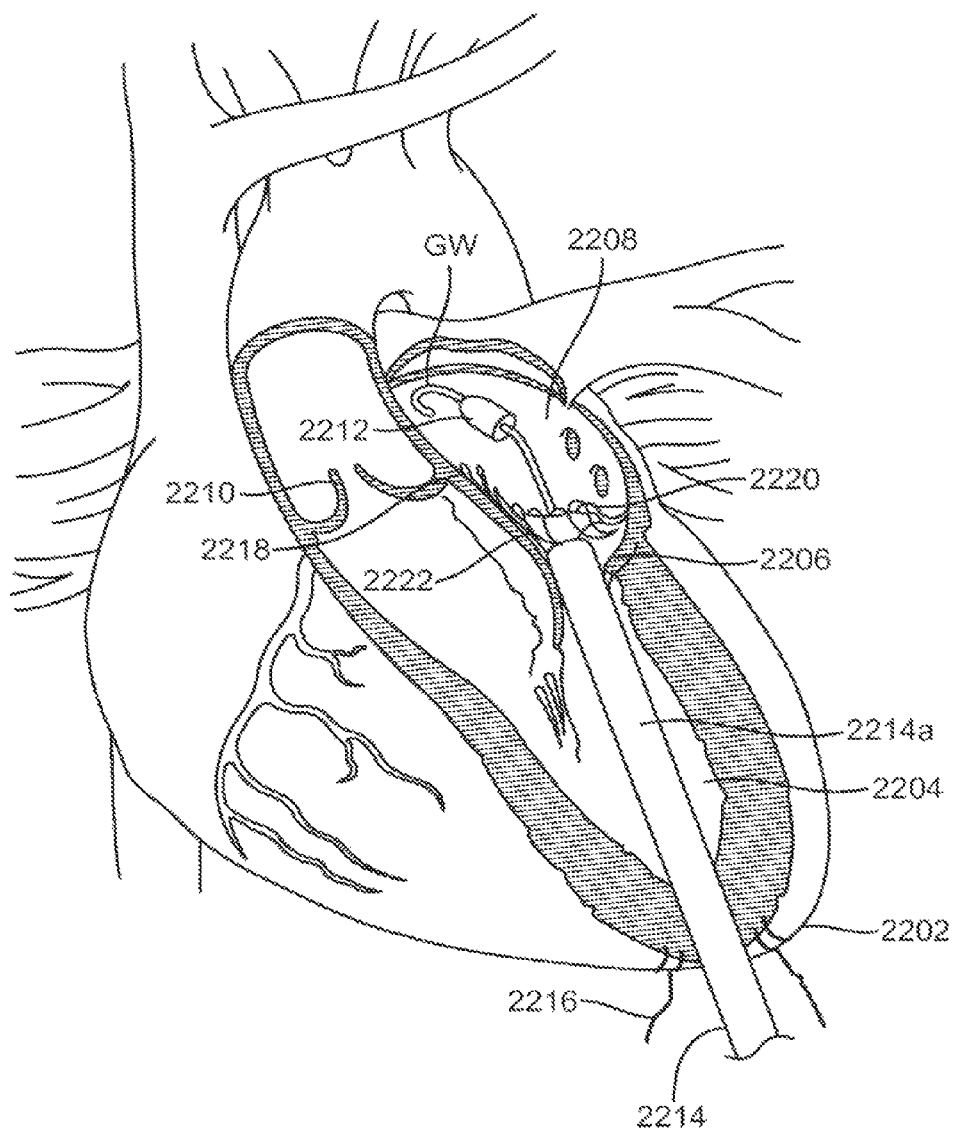

In FIG. 22D once alignment has been obtained, the sheath 2214a is further retracted proximally, allowing radial expansion of the atrial skirt 2222 which flares outward to form a flange. Proximal retraction of the delivery device 2214 and prosthetic valve 2220 seat the atrial skirt 2222 against an atrial surface adjacent the mitral valve 2206 thereby anchoring the prosthetic valve in a first position.

Figure 22E:
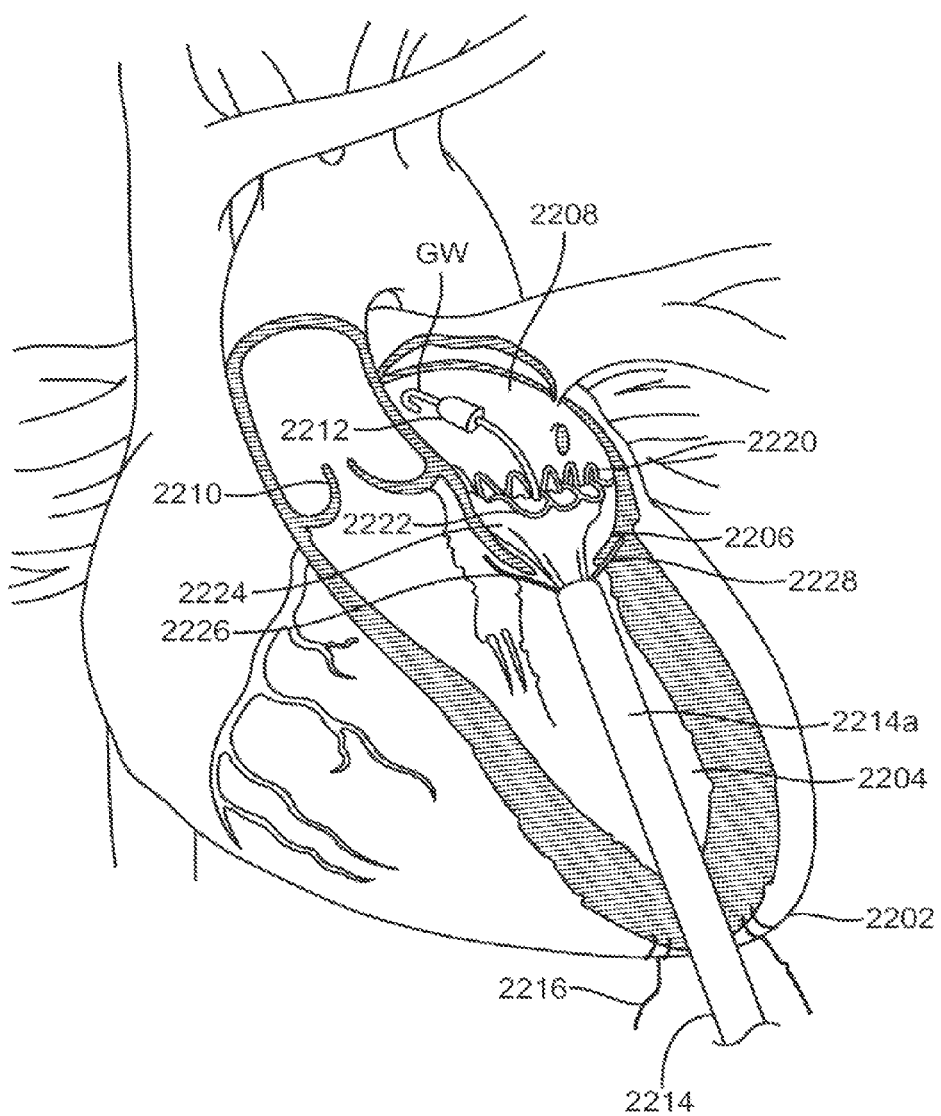

FIG. 22E shows that further proximal retraction of sheath 2214a exposes and axially removes additional constraint from the prosthetic valve 2220, thereby allowing more of the valve to self-expand. The annular region 2224 expands into engagement with the mitral valve annulus and the ventricular trigonal tabs 2226 and the posterior tab 2228 radially expand. Portions of the ventricular skirt serve as deployment control regions and prevent the entire ventricular skirt from expanding because they are still constrained. The tabs are captured between the anterior and posterior mitral valve leaflets and the ventricular wall. The posterior ventricular anchoring tab 2228 is preferably aligned in the middle of the posterior mitral valve leaflet where there is an absence of chordae attachments, and is passed over the posterior leaflet to seat between the posterior leaflet and the ventricular wall. The two ventricular trigonal anchoring tabs 2226 are positioned on either side of the anterior leaflet with their heads positioned at the fibrous trigones. Slight rotation and realignment of the prosthesis can occur at this time. As the prosthesis expands, the anterior trigonal tabs anchor against the fibrous trigones, capturing the native anterior leaflet and chordae between the tabs and the anterior surface of the prosthetic valve, and the posterior ventricular tab anchors between the ventricular wall and the posterior leaflet, capturing the posterior leaflet between the posterior anchoring tab and the posterior surface of the prosthetic valve assembly.

Figure 22F:
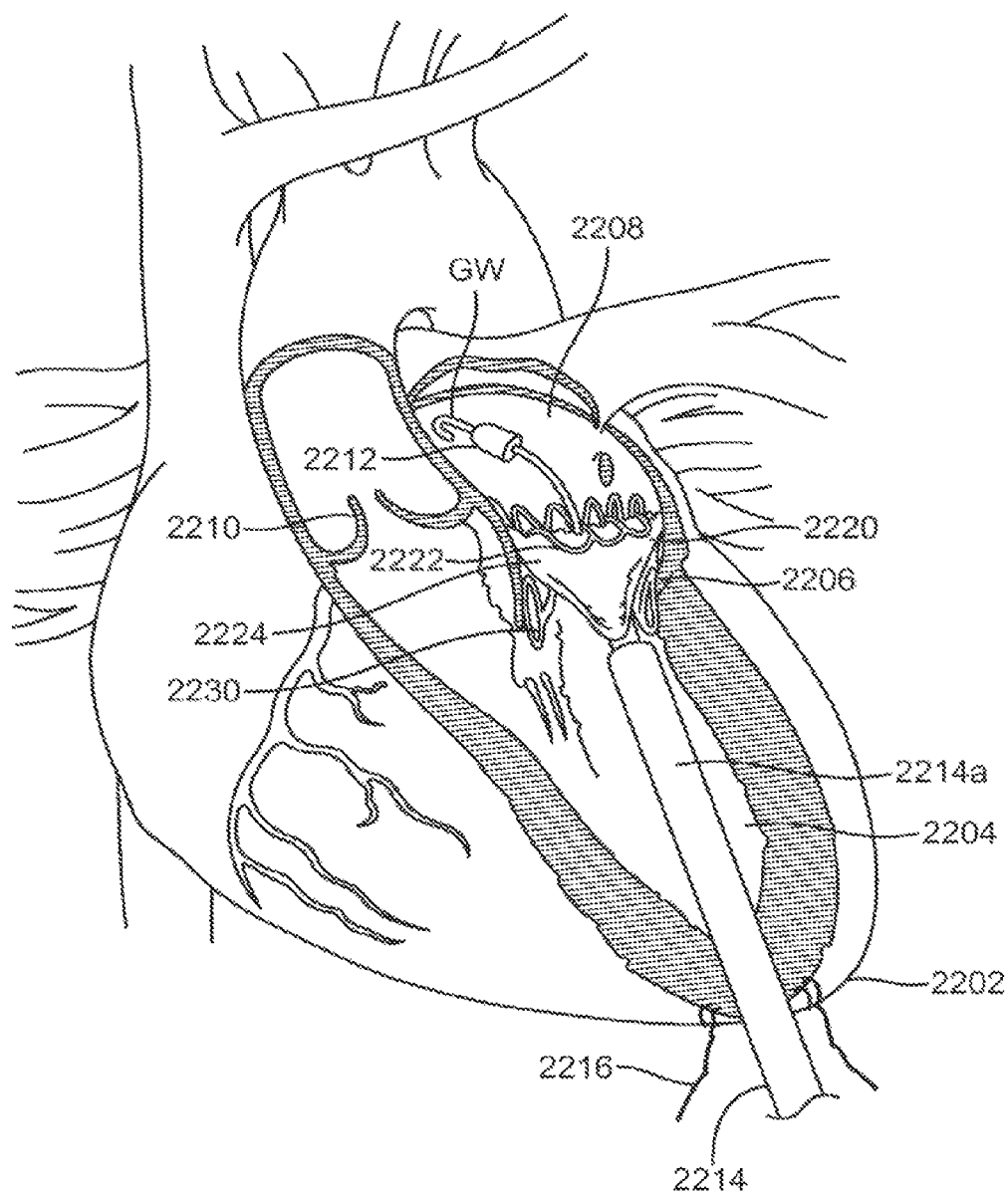
Figure 22G:
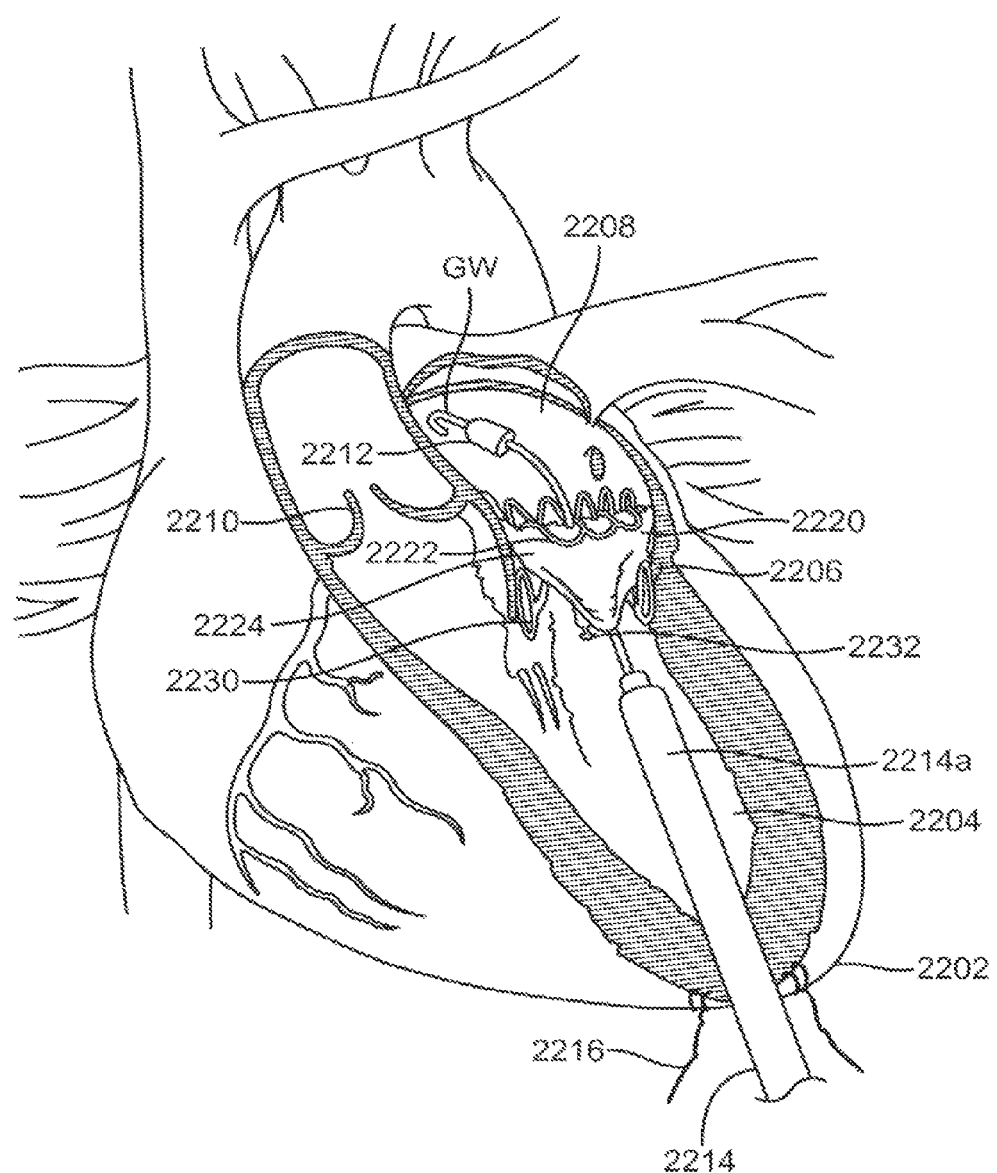

FIG. 22F shows that further retraction of sheath 2214a releases the ventricular trigonal tabs and the posterior tab and the deployment control regions of the ventricular skirt 2230 are also released and allowed to radially expand outward against the native mitral valve leaflets.

This creates a sealing funnel within the native leaflets and helps direct blood flow through the prosthetic mitral valve. With the commissures of the prosthesis still captured within the delivery system, very minor adjustments may still be made to ensure accurate positioning, anchoring and sealing. The prosthetic valve is now anchored in four positions. The anchor tabs 2232 are then released from the delivery device by retraction of an inner shaft, allowing the tabs to self-expand out of slots on the delivery catheter as previously discussed above and shown in FIG. 22G. The prosthetic valve is now implanted in the patient's heart and takes over the native mitral valve. The delivery device 2214 may then be removed from the heart by proximally retracting it and removing it from the apex incision. The suture 2216 may then be tied off, sealing the puncture site.

Figure 23A:
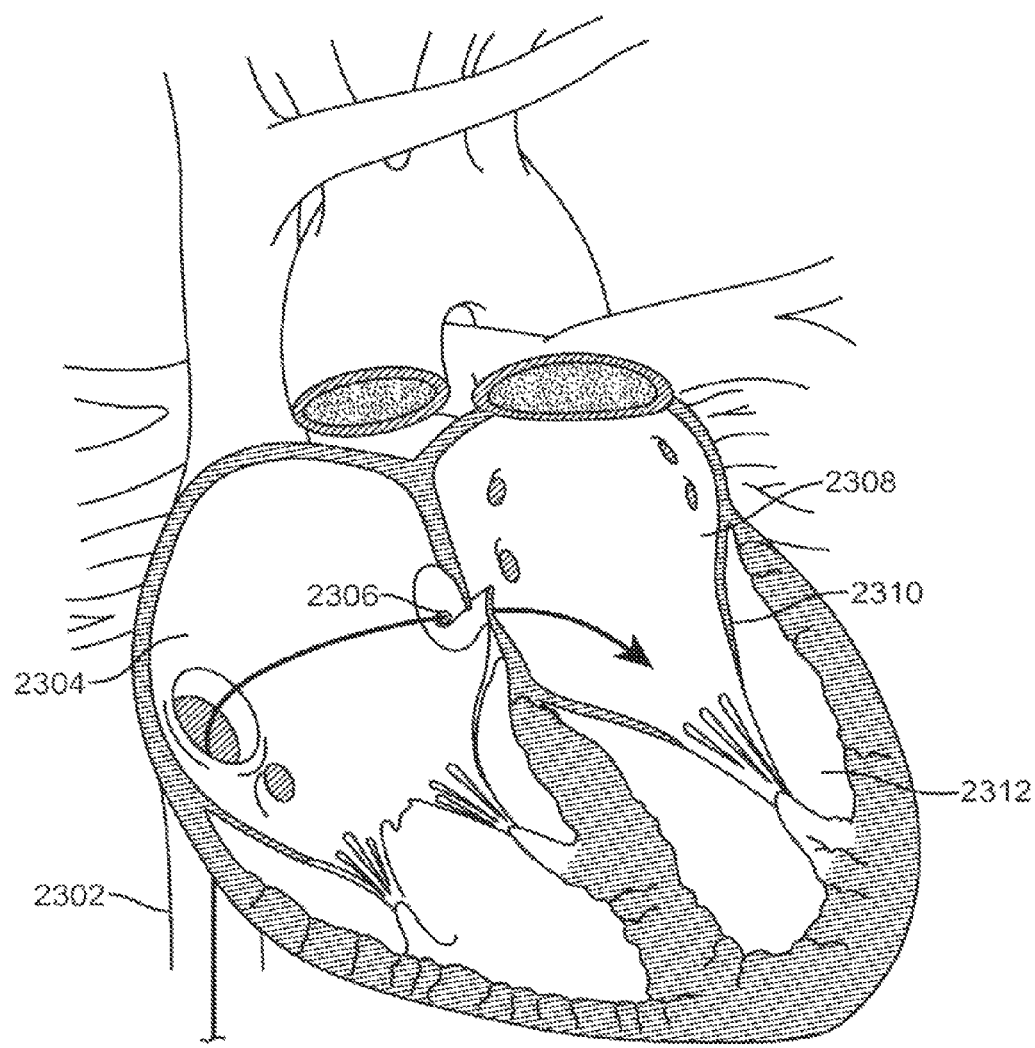
FIGS. 23A-23G illustrate an exemplary method of transseptally delivering a prosthetic mitral valve.

Transseptal Delivery Methods. FIGS. 23A-23G illustrate an exemplary method of transseptally delivering a prosthetic mitral valve. This embodiment may use any of the prosthetic valves described herein, and may use any of the delivery devices described herein if modified appropriately. One of skill in the art will appreciate that relative motion of the various shafts in the delivery system embodiments disclosed above may need to be reversed in order to accommodate a transseptal approach. FIG. 23A illustrates the general transseptal pathway that is taken with the delivery device passing up the vena cava 2302 into the right atrium 2304. A transseptal puncture 2306 is created through the atrial septum, often through the foramen ovale, so that the device may be passed into the left atrium 2308, above the mitral valve 2310 and adjacent the left ventricle 2312. Transseptal techniques have been published in the patent and scientific literature, such as in U.S. Patent Publication No. 2004/0181238 to Zarbatany et al., the entire contents of which are incorporated herein by reference.

Figure 23B:
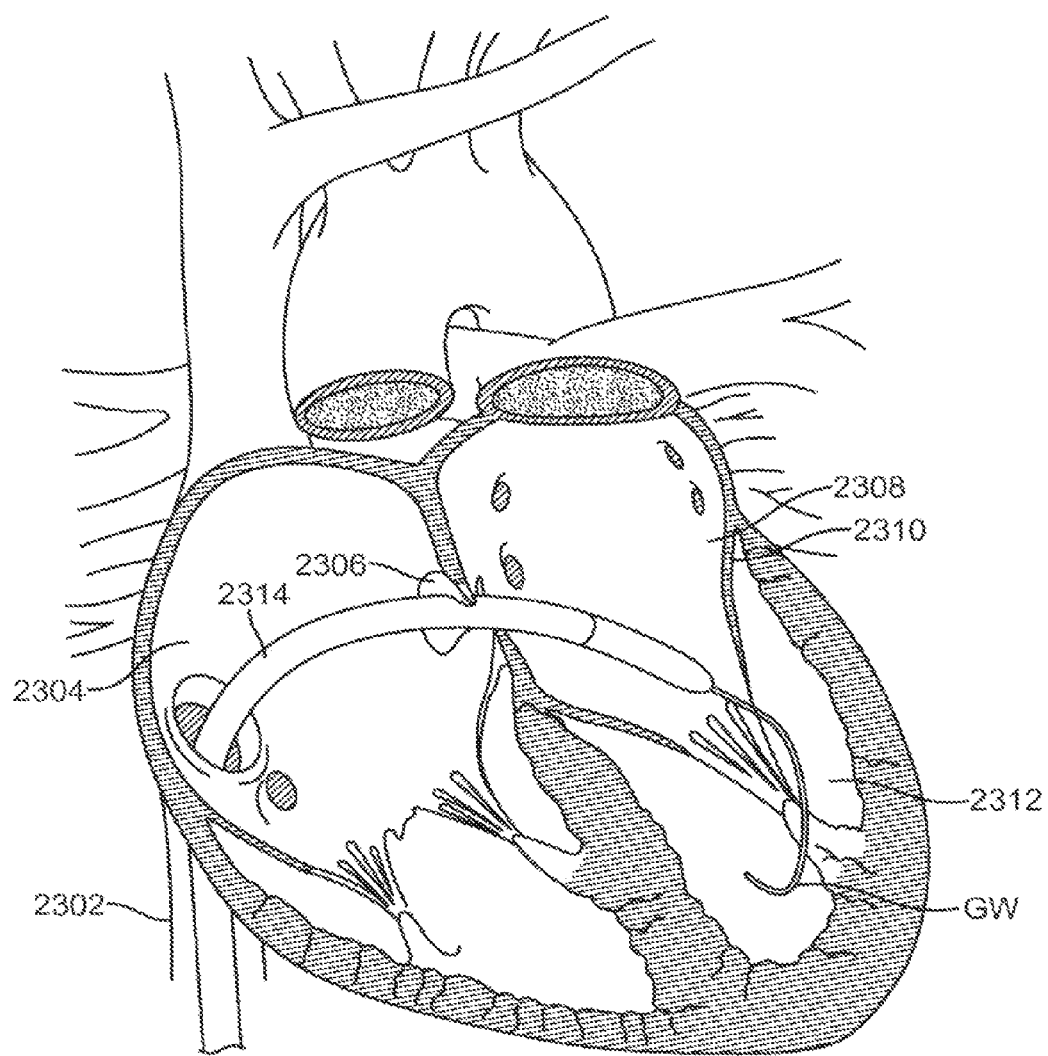

In FIG. 23B a delivery device 2314 is passed over a guidewire GW through the vena cava 2302 into the right atrium 2306. The delivery device 2314 is then transseptally passed through the atrial wall into the left atrium 2308 adjacent the mitral valve 2310. The guidewire GW may be disposed across the mitral valve 2310 in the left ventricle 2312. The distal tip of the delivery device typically includes a nose cone or other atraumatic tip to prevent damaging the mitral valve or adjacent tissue.

Figure 23C:
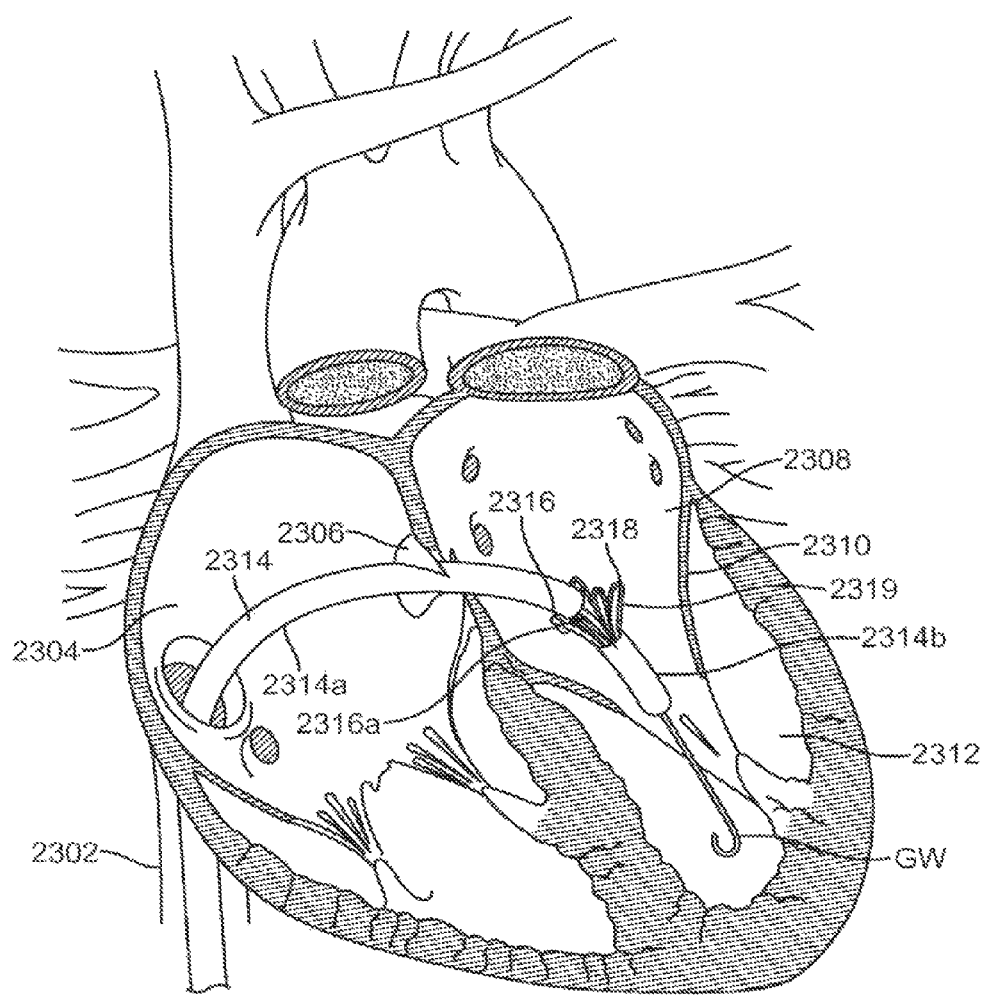

In FIG. 23C, the outer sheath 2214a of the delivery device 2214 is retracted proximally relative to the prosthetic mitral valve 2319. Alternatively, a distal portion 2314b of the delivery device 2214 may be advanced distally relative to the prosthetic valve 2319 to expose the alignment element 2316 and a portion of the atrial skirt region 2318 on the prosthetic mitral valve 2319 which allows the atrial skirt region 2318 to begin to partially radially expand outward and flare open. Alignment element 2316 may include a pair of radiopaque markers 2316a which facilitate visualization under fluoroscopy. The physician can then align the alignment element so that the radiopaque markers 2316a are disposed on either side of the anterior mitral valve leaflet. The alignment element is preferably situated adjacent the aortic root and between the fibrous trigones of the native anterior leaflet. Delivery device 2214 may be rotated in order to help align the alignment element.

Figure 23D:
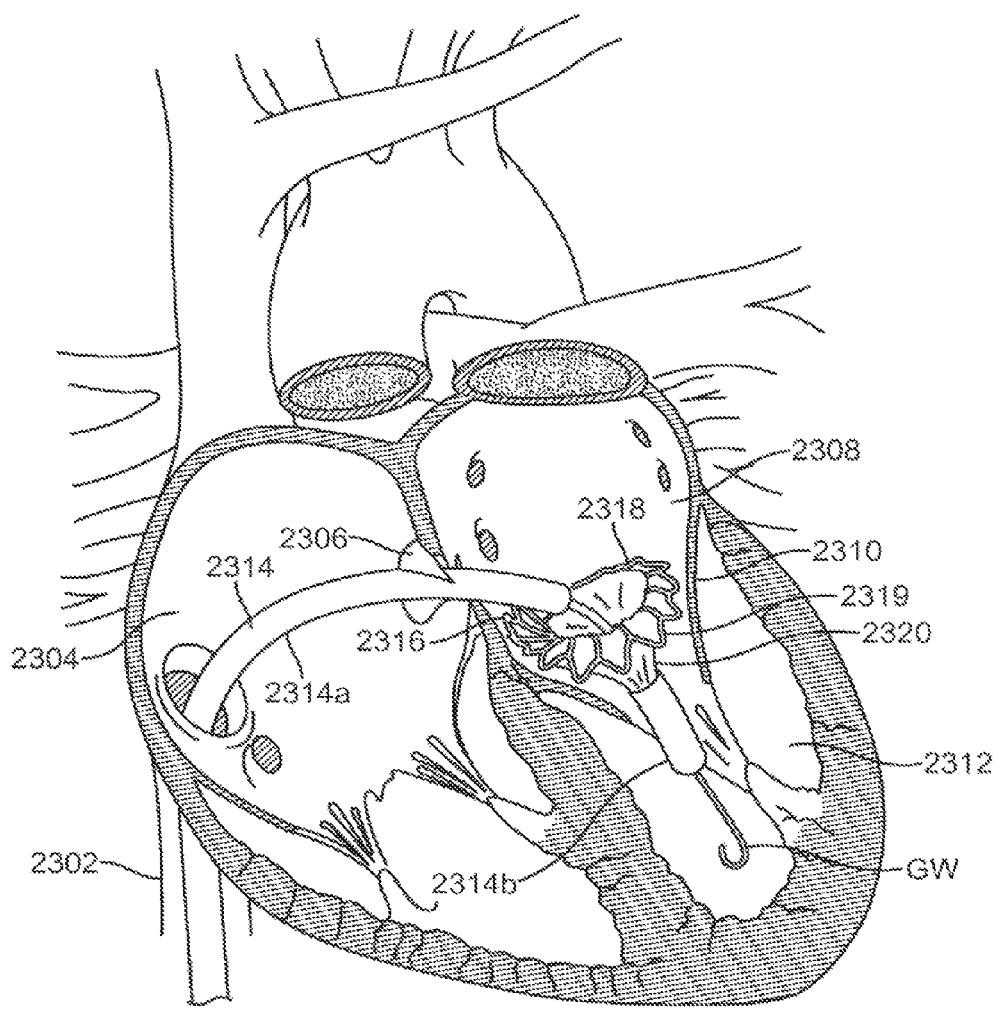

In FIG. 23D once alignment has been obtained, the distal portion 2314b is further advanced distally allowing radial expansion of the atrial skirt 2318 which flares outward to form a flange. Distally advancing the delivery device 2214 and prosthetic valve 2319 seats the atrial skirt 2318 against an atrial surface adjacent the mitral valve 2310 thereby anchoring the prosthetic valve in a first position.

Figure 23E:
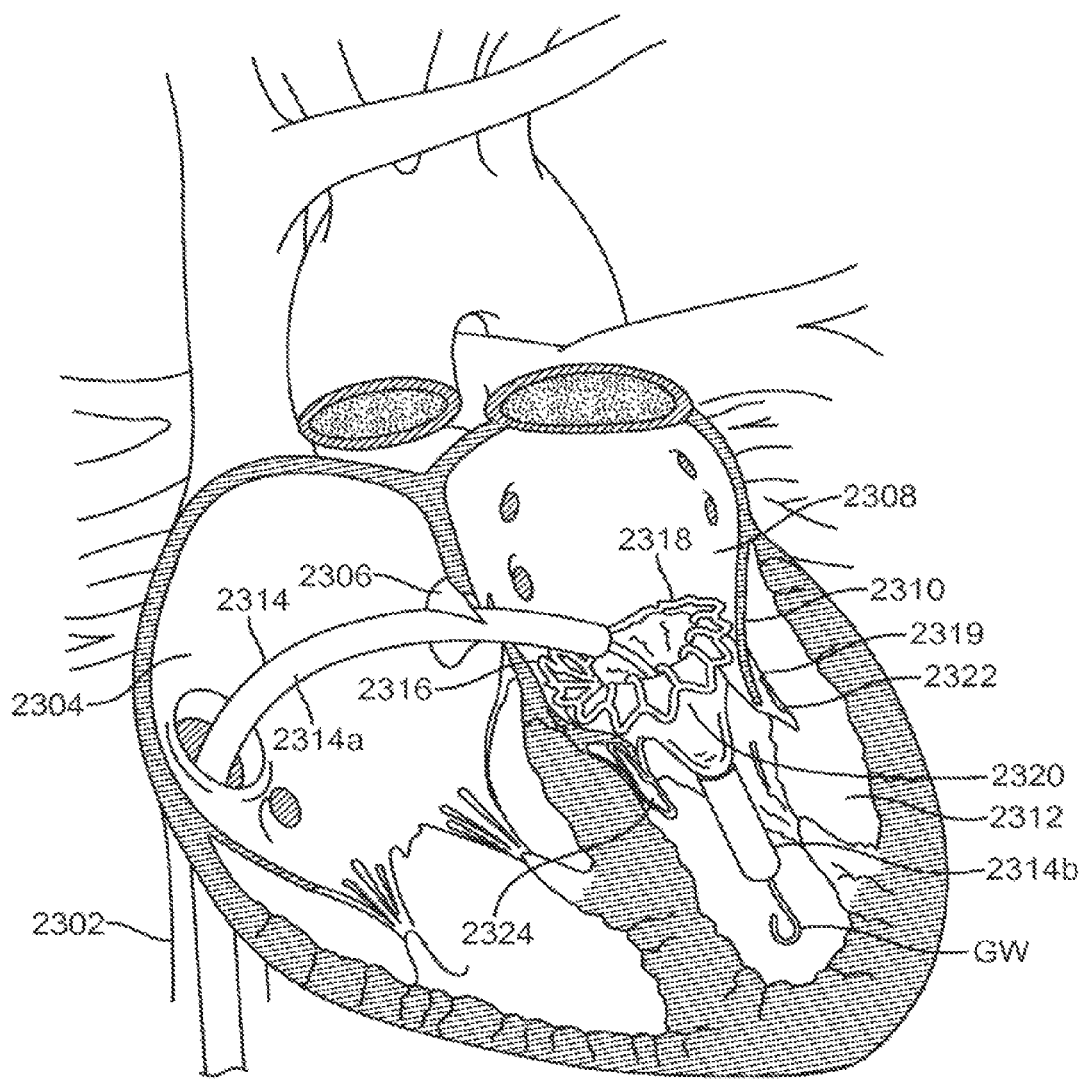

FIG. 23E shows that further distal advancement of distal portion 2314b exposes and axially removes additional constraint from the prosthetic valve 2319, thereby allowing more of the valve to self-expand. The annular region 2320 expands into engagement with the mitral valve annulus and the ventricular trigonal tabs 2324 and the posterior tab 2322 radially expand. Portions of the ventricular skirt serve as deployment control regions since they remain constrained and thus the entire ventricular skirt cannot expand. The tabs are captured between the anterior and posterior mitral valve leaflets and the ventricular wall. The posterior ventricular anchoring tab 2322 is preferably aligned in the middle of the posterior mitral valve leaflet where there is an absence of chordae attachments, and is passed over the posterior leaflet to seat between the posterior leaflet and the ventricular wall. The two ventricular trigonal anchoring tabs 2324 are positioned on either side of the anterior leaflet with their heads positioned at the fibrous trigones. Slight rotation and realignment of the prosthesis can occur at this time. As the prosthesis expands, the anterior trigonal tabs anchor against the fibrous trigones, capturing the native anterior leaflet and chordae between the tabs and the anterior surface of the prosthetic valve, and the posterior ventricular tab anchors between the ventricular wall and the posterior leaflet, capturing the posterior leaflet between the posterior anchoring tab and the posterior surface of the prosthetic valve assembly.

Figure 23F:
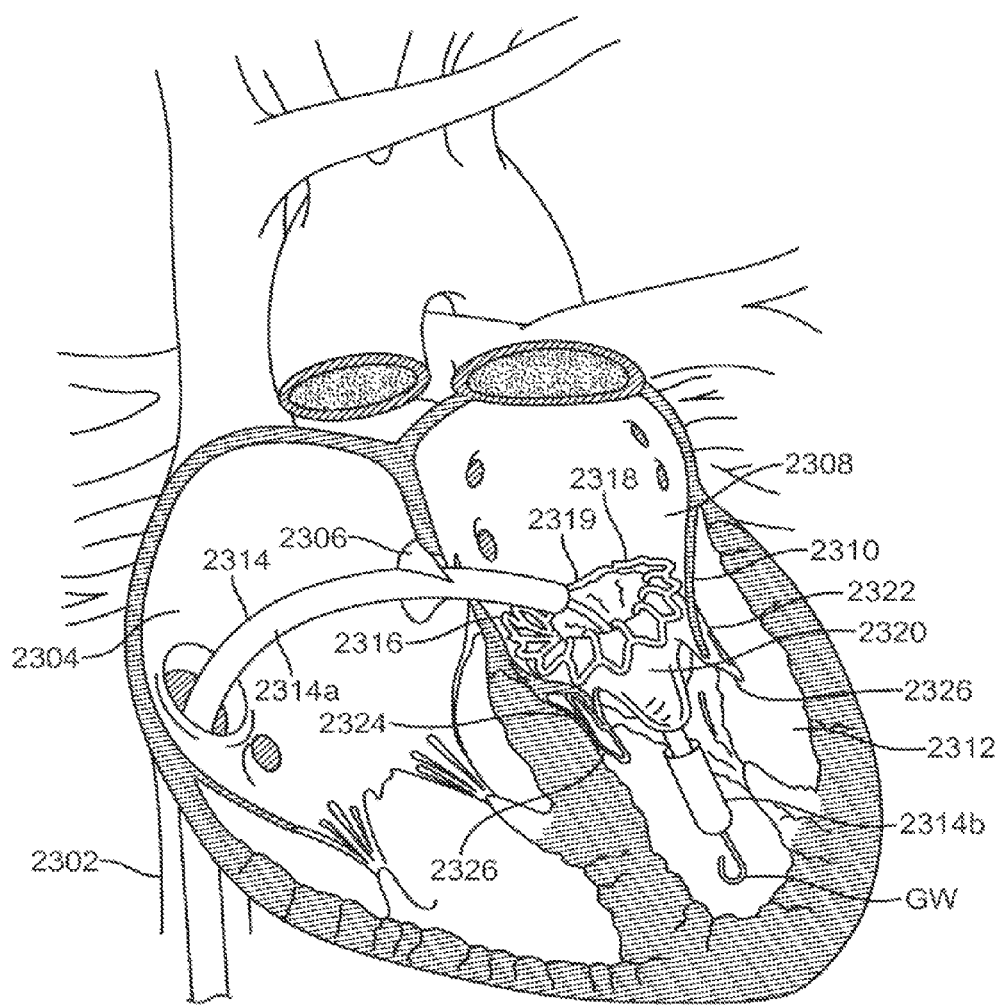
Figure 23G:
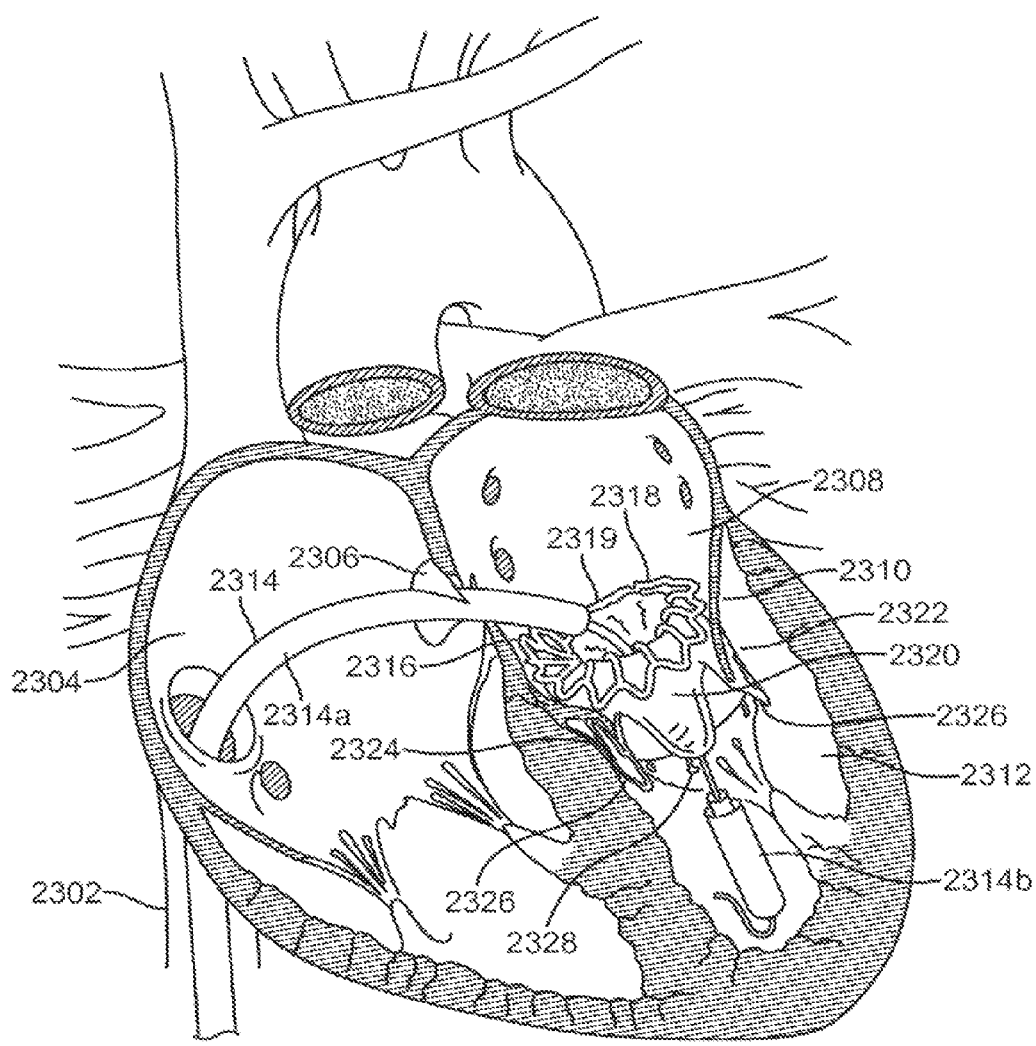

FIG. 23F shows that further distal advancement of distal portion 2314b releases the ventricular trigonal tabs and the posterior tab and the ventricular skirt 2326 is also released and allowed to radially expand outward against the native mitral valve leaflets without engaging the ventricular wall. This creates a sealing funnel within the native leaflets and helps funnel blood flow through the prosthetic valve. With the commissures of the prosthetic valve still captured by the delivery system, very minor adjustments may still be made to ensure accurate positioning, anchoring and sealing. The prosthetic valve is now anchored in four positions. The anchor tabs 2328 are then released from the delivery device by further advancement of an inner shaft, allowing the tabs to self-expand out of slots on the delivery catheter as previously discussed above and shown in FIG. 23G. The prosthetic valve is now implanted in the patient's heart and takes over the native mitral valve. The delivery device 2314 may then be removed from the heart by proximally retracting it back through the atrial septum, and out of the vena cava.

Figure 24:
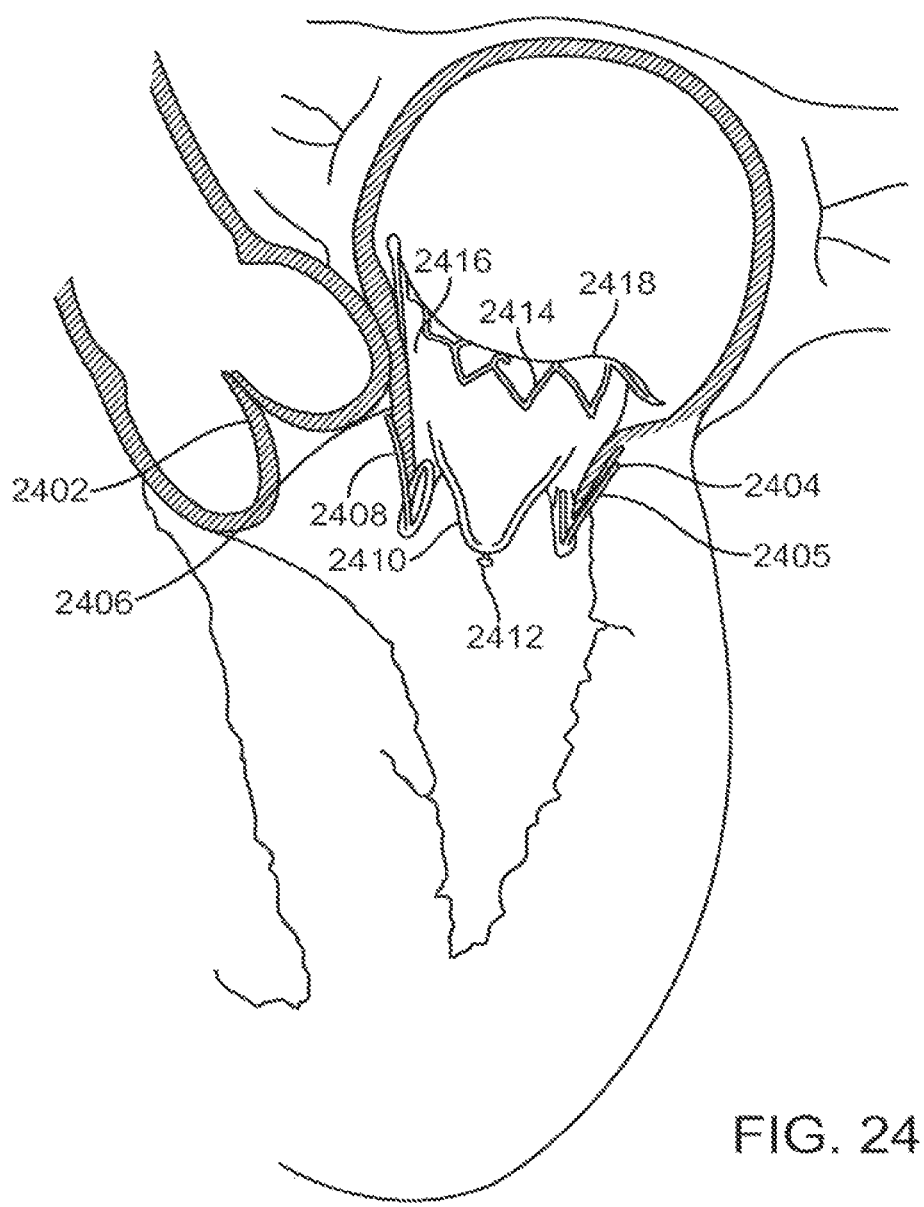
FIG. 24 illustrates a prosthetic mitral valve implanted in the mitral space.

FIG. 24 shows the prosthetic valve 2418 anchored in the mitral space after transapical or trans septal delivery. Prosthetic valve 2418 is preferably the prosthetic mitral valve illustrated in FIG. 8A, and delivered by methods shown in FIGS. 22A-22G or FIGS. 23A-23G. The prosthetic valve 2418 has radially self-expanded into engagement with the mitral valve to anchor it in position without obstructing other portions of the heart including the left ventricular outflow tract such as aortic valve 2402. The anterior trigonal tabs 2408 (only 1 seen in this view) and the posterior ventricular tab 2405 are radially expanded outward from the rest of the ventricular skirt 2410 and the anterior leaflet 2406 and posterior leaflet 2404 are captured between the respective tab and the ventricular skirt 2410 to form an anchor point. The ventricular skirt 2410 is also radially expanded outward to engage and press outwardly at least some of the chordae tendineae and papillary muscles but preferably without pressing against the ventricular wall. The annular region 2416 is expanded radially outward to engage and press against the mitral valve annulus, and the atrial skirt 2414 has also expanded outwardly to form a flange that rests on top of the mitral valve against the atrium. Thus, the prosthetic valve 2418 is anchored in four positions in the mitral space which prevents the prosthetic valve from migrating or dislodging during contraction of the heart. Moreover, using four anchor points lessens the anchoring pressure that is required to be applied in any given anchoring zone as compared to a prosthesis that is anchored in only a single anchoring zone, or in any combination of these four anchoring zones. The consequent reduction in radial force required to be exerted against the native structures in each zone minimizes the risk of obstruction or impingement of the nearby aortic valve or aortic root caused by the displacement of the native mitral valve apparatus. Valve leaflets 2420 form a tricuspid valve which opens with antegrade blood flow and closes with retrograde blood flow. Tab 2412 on a tip of the commissures 2421 (best seen in FIG. 25) remains free after disengagement from the delivery device.

Figure 25:
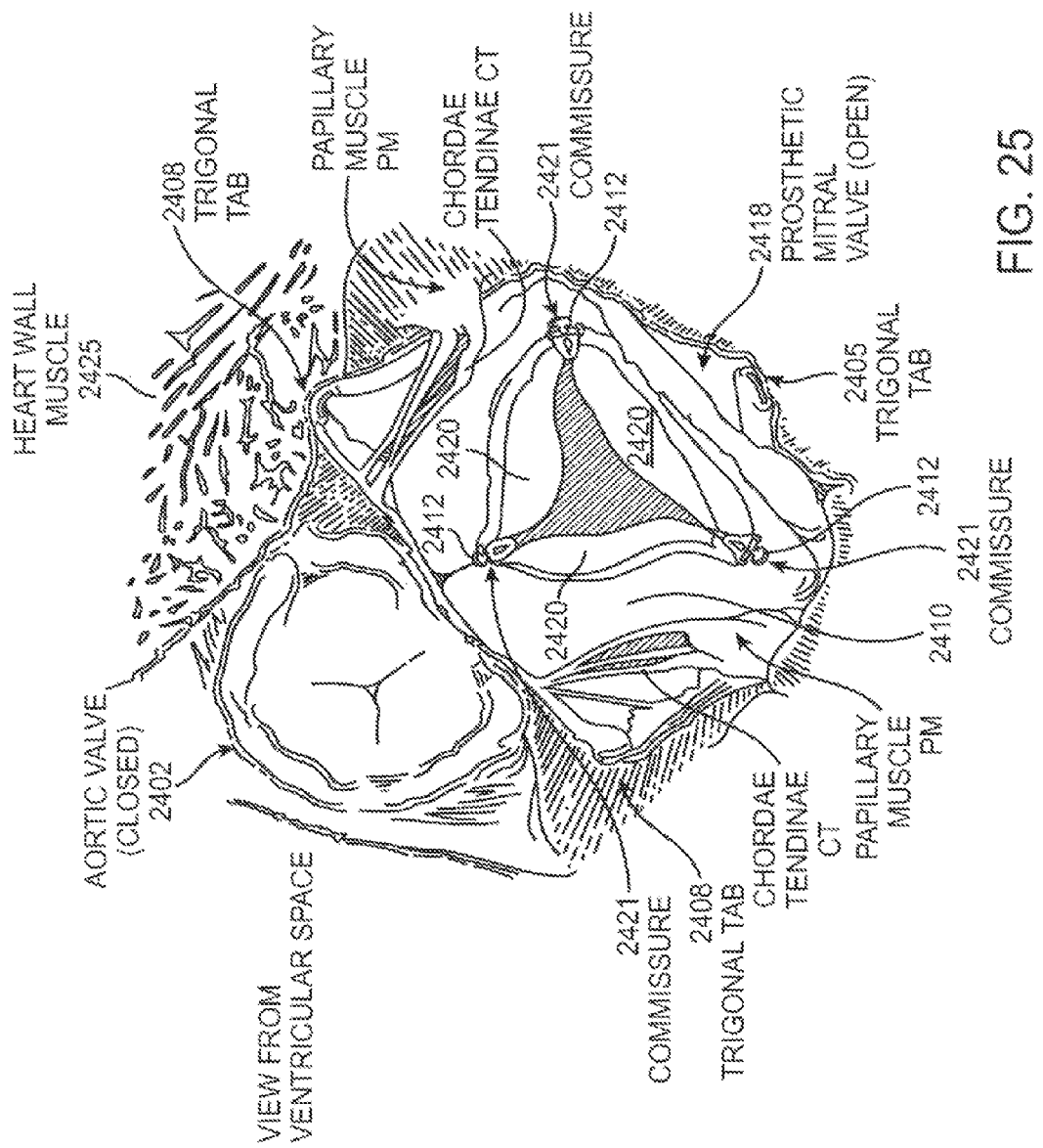
FIG. 25 illustrates a bottom view of a mitral valve implanted in the mitral space looking upward from the left ventricle.

FIG. 25 illustrates the prosthetic valve 2418 of FIG. 24 anchored in the mitral space and viewed from the left ventricle, looking upward toward the atrium. As previously mentioned, the prosthetic valve 2418 may be transapically or transseptally delivered and is preferably the prosthetic mitral valve illustrated in FIG. 8A, delivered by methods shown in FIGS. 22A-22G or FIGS. 23A-23G. This view more clearly illustrates anchoring and engagement of the prosthetic mitral valve 2418 with the adjacent tissue. For example, the three valve leaflets 2420 forming the tricuspid valve are shown in the open position, allowing blood flow therepast. Additionally, the anterior trigonal tabs 2408 and the posterior ventricular tab 2405 are shown radially expanded outward into engagement with the ventricular heart tissue 2425. The anterior portion of the prosthetic valve in between anterior trigonal tabs 2408 is approximately flat to match the corresponding flat anatomy as previously discussed above. The flat shape of the anterior portion of the prosthetic valve prevents the prosthetic valve from impinging on and obstructing adjacent anatomy such as the left ventricular outflow tract including the aortic valve. FIG. 25 also illustrates how the ventricular skirt 2410 expands radially outward against the native mitral valve leaflets.

Drug Delivery. Any of the prosthetic valves may also be used as a drug delivery device for localized drug elution. The therapeutic agent may be a coated on the prosthetic valve, on the tissue covering the anchor, on both, or otherwise carried by the prosthetic valve and controllably eluted therefrom after implantation. Exemplary drugs include anti-calcification drugs, antibiotics, anti-platelet aggregation drugs, anti-inflammatory drugs, drugs which inhibit tissue rejection, anti-restenosis drugs, anti-thrombogenic drugs, thrombolytic drugs, etc. Drugs which have these therapeutic effects are well known to those of skill in the art.

Although the exemplary embodiments have been described in some detail for clarity of understanding and by way of example, a variety of additional modifications, adaptations and changes may be clear to those of skill in the art. One of skill in the art will appreciate that the various features described herein may be combined with one another or substituted with one another. Hence, the scope of the present invention is limited solely by the appended claims.

What is claimed is:

1. A method of anchoring a prosthetic valve in a patient's heart having a native mitral valve, said method comprising:
   delivering a prosthetic cardiac mitral valve in a collapsed configuration to the patient's heart, wherein the prosthetic cardiac mitral valve comprises an anchor having a first anterior trigonal anchoring tab disposed on an anterior portion of the prosthetic cardiac mitral valve;
   radially expanding the anchor from the collapsed configuration to an expanded configuration to engage the native mitral valve;
   anchoring the prosthetic cardiac mitral valve to the native mitral valve, wherein anchoring the prosthetic cardiac mitral valve comprises expanding the first anterior trigonal anchoring tab radially outward and engaging the first anterior trigonal anchoring tab against a first fibrous trigone of the native mitral valve; and
   disposing adjacent chordae tendineae between the first anterior trigonal anchoring tab and an anterior surface of the anchor.

2. The method of claim 1, wherein expanding the first anterior trigonal anchoring tab radially outward and engaging the first anterior trigonal anchoring tab against the first fibrous trigone of the native mitral valve comprises disposing an anterior leaflet of the native mitral valve between the first anterior trigonal anchoring tab and an anterior surface of the anchor.

3. The method of claim 1, wherein the prosthetic cardiac mitral valve further comprises a second anterior trigonal anchoring tab disposed on the anterior portion of the prosthetic cardiac mitral valve, and wherein anchoring the prosthetic cardiac mitral valve further comprises expanding the second anterior trigonal anchoring tab radially outward and engaging the second anterior trigonal anchoring tab against a second fibrous trigone of the native mitral valve.

4. The method of claim 3, wherein expanding the second anterior trigonal anchoring tab radially outward and engaging the second anterior trigonal anchoring tab against the second fibrous trigone of the native mitral valve comprises disposing an anterior leaflet of the native mitral valve between the second anterior trigonal anchoring tab and an anterior surface of the anchor.

5. The method of claim 3, wherein expanding the second anterior trigonal anchoring tab radially outward and engaging the second anterior trigonal anchoring tab against the second fibrous trigone of the native mitral valve comprises disposing adjacent chordae tendineae between the second anterior trigonal anchoring tab and an anterior surface of the anchor.

6. The method of claim 1, wherein the anchor further comprises a posterior anchoring tab disposed on a posterior portion of the prosthetic cardiac mitral valve, and wherein anchoring the prosthetic cardiac mitral valve further comprises expanding the posterior anchoring tab radially outward and engaging the posterior anchoring tab with a posterior portion of the native mitral valve.

7. The method of claim 1, wherein positioning the prosthetic cardiac mitral valve in the patient's heart comprises transseptally delivering the prosthetic cardiac mitral valve from the right atrium to the left atrium of the heart.

8. The method of claim 1, wherein positioning the prosthetic cardiac mitral valve in the patient's heart comprises transapically delivering the prosthetic cardiac mitral valve from a region outside the heart to the left ventricle of the heart.

9. The method of claim 1, wherein the anchor further comprises an atrial skirt, and wherein expanding the anchor from the collapsed configuration to the expanded configuration to engage the native mitral valve comprises expanding the atrial skirt radially outward so as to lie over a superior surface of the patient's native mitral valve and anchoring the atrial skirt against a portion of the atrium.

10. The method of claim 9, wherein expanding the atrial skirt comprises slidably moving a restraining sheath away from the atrial skirt thereby allowing radial expansion thereof.

11. The method of claim 9, further comprising applying a force on the prosthetic cardiac mitral valve to ensure that the atrial skirt engages the superior surface of the native mitral valve.

12. The method of claim 9, wherein expanding the atrial skirt comprises sealing the atrial skirt against the superior surface of the native mitral valve.

13. The method of claim 9, wherein the atrial skirt comprises an alignment element, the method further comprising aligning the alignment element relative to the patient's native mitral valve.

14. The method of claim 13, wherein aligning comprises aligning the alignment element with an aortic root and disposing the alignment element between the first fibrous trigone and a second fibrous trigone of the native mitral valve.

15. The method of claim 1, wherein the anchor further comprises an annular region, and wherein expanding the anchor from the collapsed configuration to the expanded configuration to engage the native mitral valve comprises radially expanding the annular region of the anchor to conform with and to engage the native mitral valve annulus.

16. The method of claim 15, wherein radially expanding the annular region comprises slidably moving a restraining sheath away from the annular region thereby allowing radial expansion thereof.

17. The method of claim 15, wherein radially expanding the annular region comprises asymmetrically expanding the annular region such that an anterior portion of the annular region is substantially flat, and a posterior portion of the annular region is cylindrically shaped.

18. The method of claim 1, wherein the anchor comprises a ventricular skirt, and wherein expanding the anchor from the collapsed configuration to the expanded configuration to engage the native mitral valve comprises radially expanding the ventricular skirt thereby displacing native leaflets of the native mitral valve radially outward.

19. The method of claim 18, wherein radially expanding the ventricular skirt comprises slidably moving a restraining sheath away from the ventricular skirt thereby allowing radial expansion thereof.

20. The method of claim 18, wherein the prosthetic cardiac mitral valve further comprises a plurality of prosthetic valve leaflets, and wherein radially expanding the ventricular skirt comprises displacing the native mitral valve leaflets radially outward thereby preventing interference of the native mitral valve leaflets with the prosthetic valve leaflets.

21. The method of claim 18, wherein radially expanding the ventricular skirt comprises displacing the native mitral valve leaflets radially outward without contacting a ventricular wall of the patient's heart, and without obstructing a left ventricular outflow tract.

22. The method of claim 18, wherein radially expanding the ventricular skirt comprises asymmetrically expanding the ventricular skirt such that an anterior portion of the ventricular skirt is substantially flat, and a posterior portion of the ventricular skirt is cylindrically shaped.

23. The method of claim 1, wherein the prosthetic cardiac mitral valve comprises a plurality of prosthetic valve leaflets coupled to commissures, the method further comprising releasing the commissures from a delivery catheter.

24. The method of claim 23, wherein the the plurality of prosthetic valve leaflets form a tricuspid leaflet configuration.

25. The method of claim 1, wherein the prosthetic cardiac mitral valve further comprises prosthetic valve leaflets, and wherein the prosthetic cardiac mitral valve has an open configuration in which the prosthetic valve leaflets are disposed away from one another, and the prosthetic cardiac mitral valve has a closed configuration in which the prosthetic valve leaflets engage one another, and wherein blood flows freely through the prosthetic cardiac mitral valve in the open configuration, and wherein retrograde blood flow across the prosthetic cardiac mitral valve is substantially prevented in the closed configuration.

26. The method of claim 1, further comprising reducing or eliminating mitral regurgitation in the patient after implantation of the prosthetic cardiac mitral valve in the patient's heart.

27. The method of claim 1, wherein radially expanding the anchor from the collapsed configuration to an expanded configuration comprises slidably moving a restraining sheath away from the anchor, allowing at least a portion of the anchor to self-expand.

28. The method of claim 1, wherein the first anterior trigonal anchoring tab comprises two struts originating from a ventricular skirt disposed on a ventricular portion of the anchor, and joined by a u-shaped connector.

* * * * *